United States Patent
Maeda et al.

(10) Patent No.: US 7,045,595 B2
(45) Date of Patent: May 16, 2006

(54) HEMOPOIETIN RECEPTOR PROTEIN, NR12

(75) Inventors: Masatsugu Maeda, Ibaraki (JP);
Noriko Yaguchi, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 149 days.

(21) Appl. No.: 10/105,930

(22) Filed: Mar. 25, 2002

(65) Prior Publication Data
US 2003/0009018 A1 Jan. 9, 2003

Related U.S. Application Data

(63) Continuation-in-part of application No. PCT/JP00/06654, filed on Sep. 27, 2000.

(30) Foreign Application Priority Data

| Sep. 27, 1999 | (JP) | ................................. 11-273358 |
| Aug. 3, 2000 | (JP) | ............................ 2000-240397 |

(51) Int. Cl.
*C07K 14/00* (2006.01)
*C07K 14/705* (2006.01)
*C07K 14/72* (2006.01)
*C07K 14/71* (2006.01)

(52) U.S. Cl. ...................... 530/350; 530/395; 530/397; 530/399

(58) Field of Classification Search ................ 530/350, 530/395, 397
See application file for complete search history.

(56) References Cited

FOREIGN PATENT DOCUMENTS

| EP | 1 088 831 A1 | 4/2001 |
| EP | 1 188 830 A1 | 3/2002 |
| WO | WO 97/15663 A1 | 1/1997 |
| WO | WO 97/07215 | 2/1997 |
| WO | WO 97/12037 A1 | 3/1997 |
| WO | WO 00/73451 A1 | 12/2000 |
| WO | WO 01/85790 A2 | 11/2001 |
| WO | WO 02/29060 A2 | 4/2002 |

OTHER PUBLICATIONS

Cosman, The Hematopoietin Receptor Superfamily. Cytokine vol. 5/2:95-106 (1993).*
Wells et al., Hematopoietic Receptor Complexes. Annu. Rev. Biochem. 65:609-34 (1996).*
Bork et al. Go hunting in sequence databases but watch out for the traps. Trends in Genetics 12:425-427 (1996).*
Bork, Powers and Pitfalls in Sequence Analysis:The 70% Hurdle. Genome Research 10:398-400 (2000).*
Wells, Additivity of Mutational Effects in Proteins. Biochemistry vol. 29/37 8509-8517 (1990).*
Abbas et al. Cellular and Molecular Immunology, Second Edition. W.B. Saunders Company, Philadelphia (1994).*
Bepler et al., A 1.4-Mb high-resolution physical map and contig of chromosome segment 11p15.5 and genes in the LOH11A metastasis suppressor region, *Genomics*, vol. 55 (2), pp. 164-175, 1999.
Gainsford et al., "Leptin can induce proliferation, differentiation, and functional activation of hemopoietic cells", *Proc. Natl. Acad. Sci. USA*, vol. 93, pp. 14564-14568, Dec. 1996.
Hilton et al., "Cloning and characterization of a binding subunit of the interleukin 13 receptor that is also a component of the interleukin 4 receptor", *Proc. Natl. Acad. Sci. USA*, vol. 93, pp. 497-501, Jan. 1996.
Oppmann et al., "Novel p19 Protein Engages IL-12p40 to Form a Cytokine, IL-23, with biological Activities Similar as Well as Distinct from IL-12", *Immunity*, vol. 13, pp. 715-725, 2000.
Robb et al., "Structural Analysis of the Gene Encoding the Murine Interleukin-11 Receptor α-Chain and a Related Locus", *The Journal of Biological Chemistry*, vol. 271, No. 23, pp. 13754-13761, 1996.
GenBank Accession No. AF102051 Dated 1999.
Saito et al., "Molecular Cloning of a Murine IL-6 Receptor-Associated Signal Transducer, gp130, and its Regulated Expression in Vivo", *The Journal of Immunology*, vol. 148 (12); pp. 4066-4071 (1992).
Alexander, et al. "Suckling defect in mice lacking the soluble haemopoietin receptor NR6", *Current Biology*, vol. 9(11), pp. 605-608 (1999).

* cited by examiner

*Primary Examiner*—Joseph Murphy
*Assistant Examiner*—Regina M. DeBerry
(74) *Attorney, Agent, or Firm*—Fish & Richardson P.C.

(57) ABSTRACT

A novel hemopoietin receptor gene (NR12) was successfully isolated by extracting motifs conserved among the amino acid sequences of known hemopoietin receptors and by using the predicted sequence. The NR12 gene encodes two forms of proteins, a transmembrane type and a soluble type. The expression of the NR12 gene was detected in tissues containing hematopoietic cells. NR12 is a novel hemopoietin receptor molecule involved in the regulation of immune system and hematopoiesis in vivo. Thus, NR12 is useful in the search for novel hematopoietic factors that functionally bind to the NR12 receptor, and in the development of therapeutic drugs for diseases associated with immunity or hematopoiesis.

6 Claims, 14 Drawing Sheets

```
  1  tttatatataaagaacacctttgttttcctagagtctagaagacagcttggaacataatagg 61  tgttccatacatttctgctaaataaatagttgtttaaaagcacaccacattttatat 121  tgttacccatccatttagGTAAAGAGAATTTGACACCAATTTTACATATGTGCAACAGTC
                        ValLysGluPheAspThrAsnPheThrTyrValGlnGlnSer 181  AGAATTCTACTTGGAGCCAAACATTAAGTACGTATTCAAGTGAGATGTCAAGAAACAGG
     GluPheTyrLeuGluProAsnIleLysTyrValPheGlnValArg CysGlnGluThrGly 241  CAAAAGGTACTGGCAGCCTTGGAGTTCACTGTTTTTCATAAAACACCTGAAACAGgtga
     LysArgTyrTrpGlnProTrpSer SerLeuPheHisLysThrProGluThr 301  gtgtacttatatttattctgttggctttcttatatctttctgctgagcaca
```

| | |
|---|---|
| hNR12 | LEPNIKYVFQVRC--QETGKRYWQPWS |
| gp130 | LKPFTEYVFRIRCMKEDGKGYWSDWS |

| | |
|---|---|
| hNR12 | VLEPNIKYVFQVRC--Q-ETGKRYWQPWS |
| hNR 9 | HIDPNVDYQFRV--CARGD--GROEWSPWS |

| | |
|---|---|
| hNR12 | QQSEFY----LEPNIKYVFQVRCQETGKRYWQPWSSLFFHKTP |
| hPRLR | QQMEFKILSIHPGQKYLVQVRC-KPDHGYWSAWSPATFIQIP |

| | |
|---|---|
| hNR12 | INFTYVQSEFYLEPNIKY-VFQVRC-QE-TGKRYWQPWS-SLFFHKTPE |
| hIL7R | IKLTLQR-K---LQPAAMYEI-KVRSIPDHYFKGEWSEWSPS-YYFRTPE |

| | |
|---|---|
| hNR12 | LEPN-IKYVFQVRCQ-ETG-KRYWQPWSSLFFHKTPE |
| hLIFR | LNPYTL-YTFRIRCSTETFWK--WSKWSNKKQHLTTE |

```
   1 ATGACACAGCCAACAAGGGTGGCAGCCTGGCTCTGAAGTGGAATTATGTGCTTCAAACAG
  61 GTTGAAAGAGGGAAACAGTCTTTTCCTGCTTCCAGACATGAATCAGGTCACTATTCAATG
                                          MetAsnGlnValThrIleGlnTrp
 121 GGATGCAGTAATAGCCCTTTACATACTCTTCAGCTGGTGTCATGGAGGAATTACAAATAT
     AspAlaValIleAlaLeuTyrIleLeuPheSerTrpCysHisGlyGlyIleThrAsnIle
 181 AAACTGCTCTGGCCACATCTGGGTAGAACCAGCCACAATTTTTAAGATGGGTGTGAATAT
     AsnCysSerGlyHisIleTrpValGluProAlaThrIlePheLysMetGlyValAsnIle
 241 CTCTATATATTGCCAAGCAGCAATTAAGAACTGCCAACCAAGGAAACTTCATTTTTATAA
     SerIleTyrCysGlnAlaAlaIleLysAsnCysGlnProArgLysLeuHisPheTyrLys
 301 AAATGGCATCAAAGAAAGATTTCAAATCACAAGGATTAATAAAACAACAGCTCGGCTTTG
     AsnGlyIleLysGluArgPheGlnIleThrArgIleAsnLysThrThrAlaArgLeuTrp
 361 GTATAAAAACTTTCTGGAACCACATGCTTCTATGTACTGCACTGCTGAATGTCCCAAACA
     TyrLysAsnPheLeuGluProHisAlaSerMetTyrCysThrAlaGluCysProLysHis
 421 TTTTCAAGAGACACTGATATGTGGAAAGACATTTCTTCTGGATATCCGCCAGATATTCC
     PheGlnGluThrLeuIleCysGlyLysAspIleSerSerGlyTyrProProAspIlePro
 481 TGATGAAGTAACCTGTGTCATTTATGAATATTCAGGCAACATGACTTGCACCTGGAATGC
     AspGluValThrCysValIleTyrGluTyrSerGlyAsnMetThrCysThrTrpAsnAla
 541 TGGGAGGCTCACCTACATAGACACAAAATACGTGGTACATGTGAAGAGTTTAGAGACAGA
     GlyArgLeuThrTyrIleAspThrLysTyrValValHisValLysSerLeuGluThrGlu
 601 AGAAGAGCAACAGTATCTCACCTCAAGCTATATTAACATCTCCACTGATTCATTACAAGG
     GluGluGlnGlnTyrLeuThrSerSerTyrIleAsnIleSerThrAspSerLeuGlnGly
 661 TGGCAAGAAGTACTTGGTTTGGGTCCAAGCAGCAAACGCACTAGGCATGGAAGAGTCAAA
     GlyLysLysTyrLeuValTrpValGlnAlaAlaAsnAlaLeuGlyMetGluGluSerLys
 721 ACAACTGCAAATTCACCTGGATGATATAGTGATACTTTCTGCAGCCGTCATTTCCAGGGC
     GlnLeuGlnIleHisLeuAspAspIleValIleLeuSerAlaAlaValIleSerArgAla
 781 TGAGACTATAAATGCTACAGTGCCCAAGACCATAATTTATTGGGATAGTCAAACAACAAT
     GluThrIleAsnAlaThrValProLysThrIleIleTyrTrpAspSerGlnThrThrIle
 841 TGAAAAGGTTTCCTGTGAAATGAGATACAAGGCTACAACAAACCAAACTTGGAATGTTAA
     GluLysValSerCysGluMetArgTyrLysAlaThrThrAsnGlnThrTrpAsnValLys
 901 AGAATTTGACACCAATTTTACATATGTGCAACAGTCAGAATTCTACTTGGAGCCAAACAT
     GluPheAspThrAsnPheThrTyrValGlnGlnSerGluPheTyrLeuGluProAsnIle
 961 TAAGTACGTATTTCAAGTGAGATGTCAAGAAACAGGCAAAAGGTACTGGCAGCCTTGGAG
     LysTyrValPheGlnValArgCysGlnGluThrGlyLysArgTyrTrpGlnProTrpSer
1021 TTCACTGTTTTTTCATAAAACACCTGAAACAGGTGAGTGTACTTATATATTTTATTCTGT
     SerLeuPhePheHisLysThrProGluThrGlyGluCysThrTyrIlePheTyrSerVal
1081 TGGGCTTTTCTTTATATATCTTTTCTGCTGAGCACAGTGGCTCACGCCTGTAATTCCAGC
     GlyLeuPhePheIleTyrLeuPheCys***
1141 ACTTTGAGAGGCCAAGGCAGGAAGATTGCTTGAGCCTAGGAGTTTGAGACTGGCCTGGGC
1201 AACATGGTGAGACCCTAGTCTGTACAGAAAAATAATAATTATTATTAGCCTGGGTGGTGG
1261 AATGCATTTGTAGTCGCAGCTACTTGGGAGGCTGAGGTAGTAGGATTGCGTGAGCCCGGG
1321 AGTTTGATGCTGCAGTGAGCTATGATCATCCCACTGCTCTCTAGCCTGGAGGAAAGACCA
1381 AGACCCTGTTTCCTAAAAAGTTTAAAACAGCCAGGTGCAGTGGCTTATGTCTGTAATCCC
1441 AGCACTTTGGGAGGCCAAGGTGGGTGGATTACCTTAGGTCAGGACTTCAAGACCTCCTCG
1501 GCCGACATGGTGAAACCCTGTCTCTACTAAAAATACGAAAATTAGCTGGGCATGGTGGCA
1561 GGTGCCTGTAATCTCAGCTACTCGGAAGGCTGAGGCAGGAAAATTGCTTGAACCCAAGAA
1621 GTGGAGGTTGCAGTGAACTGAGATTGTACCACCGCACTCCAGCCTGGCCAAGAGAGAGAG
1681 ACTTGGTCTCAAAAAAAAATAAAAATAAAAATAATAATAATAAATAAGTTAAAAACAAAA
1741 TAAAGCTACAAGATAAAAAAAAAAAAAAAAAAAAAAAAAAAA
```

FIG. 4

```
  1 ATGACACAGCCAACAAGGGTGGCAGCCTGGCTCTGAAGTGGAATTATGTGCTTCAAACAG
 61 GTTGAAAGAGGGAAACAGTCTTTTCCTGCTTCCAGACATGAATCAGGTCACTATTCAATG
                                              MetAsnGlnValThrIleGlnTrp
121 GGATGCAGTAATAGCCCTTTACATACTCTTCAGCTGGTGTCATGGAGGAATTACAAATAT
    AspAlaValIleAlaLeuTyrIleLeuPheSerTrpCysHisGlyGlyIleThrAsnIle
181 AAACTGCTCTGGCCACATCTGGGTAGAACCAGCCACAATTTTTAAGATGGGTGTGAATAT
    AsnCysSerGlyHisIleTrpValGluProAlaThrIlePheLysMetGlyValAsnIle
241 CTCTATATATTGCCAAGCAGCAATTAAGAACTGCCAACCAAGGAAACTTCATTTTTATAA
    SerIleTyrCysGlnAlaAlaIleLysAsnCysGlnProArgLysLeuHisPheTyrLys
301 AAATGGCATCAAAGAAAGATTTCAAATCACAAGGATTAATAAAACAACAGCTCGGCTTTG
    AsnGlyIleLysGluArgPheGlnIleThrArgIleAsnLysThrThrAlaArgLeuTrp
361 GTATAAAAACTTTCTGGAACCACATGCTTCTATGTACTGCACTGCTGAATGTCCCAAACA
    TyrLysAsnPheLeuGluProHisAlaSerMetTyrCysThrAlaGluCysProLysHis
421 TTTTCAAGAGACACTGATATGTGGAAAAGACATTTCTTCTGGATATCCGCCAGATATTCC
    PheGlnGluThrLeuIleCysGlyLysAspIleSerSerGlyTyrProProAspIlePro
481 TGATGAAGTAACCTGTGTCATTTATGAATATTCAGGCAACATGACTTGCACCTGGAATGC
    AspGluValThrCysValIleTyrGluTyrSerGlyAsnMetThrCysThrTrpAsnAla
541 TGGGAGGCTCACCTACATAGACACAAAATACGTGGTACATGTGAAGAGTTTAGAGACAGA
    GlyArgLeuThrTyrIleAspThrLysTyrValValHisValLysSerLeuGluThrGlu
601 AGAAGAGCAACAGTATCTCACCTCAAGCTATATTAACATCTCCACTGATTCATTACAAGG
    GluGluGlnGlnTyrLeuThrSerSerTyrIleAsnIleSerThrAspSerLeuGlnGly
661 TGGCAAGAAGTACTTGGTTTGGGTCCAAGCAGCAAACGCACTAGGCATGGAAGAGTCAAA
    GlyLysLysTyrLeuValTrpValGlnAlaAlaAsnAlaLeuGlyMetGluGluSerLys
721 ACAACTGCAAATTCACCTGGATGATATAGTGATACTTTCTGCAGCCGTCATTTCCAGGGC
    GlnLeuGlnIleHisLeuAspAspIleValIleLeuSerAlaAlaValIleSerArgAla
781 TGAGACTATAAATGCTACAGTGCCCAAGACCATAATTTATTGGGATAGTCAAACAACAAT
    GluThrIleAsnAlaThrValProLysThrIleIleTyrTrpAspSerGlnThrThrIle
841 TGAAAAGGTTTCCTGTGAAATGAGATACAAGGCTACAACAAACCAAACTTGGAATGTTAA
    GluLysValSerCysGluMetArgTyrLysAlaThrThrAsnGlnThrTrpAsnValLys
901 AGAATTTGACACCAATTTTACATATGTGCAACAGTCAGAATTCTACTTGGAGCCAAACAT
    GluPheAspThrAsnPheThrTyrValGlnGlnSerGluPheTyrLeuGluProAsnIle
961 TAAGTACGTATTTCAAGTGAGATGTCAAGAAACAGGCAAAAGGTACTGGCAGCCTTGGAG
    LysTyrValPheGlnValArgCysGlnGluThrGlyLysArgTyrTrpGlnProTrpSer
1021 TTCACTGTTTTTTCATAAAACACCTGAAACAGTTCCCCAGGTCACATCAAAAGCATTCCA
     SerLeuPhePheHisLysThrProGluThrValProGlnValThrSerLysAlaPheGln
1081 ACATGACACATGGAATTCTGGGCTAACAGTTGCTTCCATCTCTACAGGGCACCTTACTTC
     HisAspThrTrpAsnSerGlyLeuThrValAlaSerIleSerThrGlyHisLeuThrSer
1141 TGACAACAGAGGAGACATTGGACTTTTATTGGGAATGATCGTCTTTGCTGTTATGTTGTC
     AspAsnArgGlyAspIleGlyLeuLeuLeuGlyMetIleValPheAlaValMetLeuSer
1201 AATTCTTTCTTTGATTGGGATATTTAACAGATCATTCCGAACTGGGATTAAAAGAAGGAT
     IleLeuSerLeuIleGlyIlePheAsnArgSerPheArgThrGlyIleLysArgArgIle
1261 CTTATTGTTAATACCAAAGTGGCTTTATGAAGATATTCCTAATATGAAAAACAGCAATGT
     LeuLeuLeuIleProLysTrpLeuTyrGluAspIleProAsnMetLysAsnSerAsnVal
1321 TGTGAAAATGCTACAGCCAGGTGTGGTGGTGTGCTCCTGTGATCCAGCTACTTGGGAAG
     ValLysMetLeuGlnProGlyValValValCysSerCysAspProSerTyrLeuGlySer
1381 CTGAAGTAGGAGGACTGCTTGAGCCCAGGAGTCCAACACCAGCTTCACAACATACCAAGA
     ***
1441 CCCTGTCTCAAAAAAAAAAAAAAAAAAAAAAAAAAAAAAA
```

FIG. 5

```
   1 ATGACACAGCCAACAAGGGTGGCAGCCTGGCTCTGAAGTGGAATTATGTGCTTCAAACAG
  61 GTTGAAAGAGGGAAACAGTCTTTTCCTGCTTCCAGACATGAATCAGGTCACTATTCAATG
                                        MetAsnGlnValThrIleGlnTrp
 121 GGATGCAGTAATAGCCCTTTACATACTCTTCAGCTGGTGTCATGGAGGAATTACAAATAT
     AspAlaValIleAlaLeuTyrIleLeuPheSerTrpCysHisGlyGlyIleThrAsnIle
 181 AAACTGCTCTGGCCACATCTGGGTAGAACCAGCCACAATTTTTAAGATGGGTGTGAATAT
     AsnCysSerGlyHisIleTrpValGluProAlaThrIlePheLysMetGlyValAsnIle
 241 CTCTATATATTGCCAAGCAGCAATTAAGAACTGCCAACCAAGGAAACTTCATTTTTATAA
     SerIleTyrCysGlnAlaAlaIleLysAsnCysGlnProArgLysLeuHisPheTyrLys
 301 AAATGGCATCAAAGAAAGATTTCAAATCACAAGGATTAATAAAACAACAGCTCGGCTTTG
     AsnGlyIleLysGluArgPheGlnIleThrArgIleAsnLysThrThrAlaArgLeuTrp
 361 GTATAAAAACTTTCTGGAACCACATGCTTCTATGTACTGCACTGCTGAATGTCCAAACA
     TyrLysAsnPheLeuGluProHisAlaSerMetTyrCysThrAlaGluCysProLysHis
 421 TTTTCAAGAGACACTGATATGTGGAAAAGACATTTCTTCTGGATATCCGCCAGATATTCC
     PheGlnGluThrLeuIleCysGlyLysAspIleSerSerGlyTyrProProAspIlePro
 481 TGATGAAGTAACCTGTGTCATTTATGAATATTCAGGCAACATGACTTGCACCTGGAATGC
     AspGluValThrCysValIleTyrGluTyrSerGlyAsnMetThrCysThrTrpAsnAla
 541 TGGGAGGCTCACCTACATAGACACAAAATACGTGGTACATGTGAAGAGTTTAGAGACAGA
     GlyArgLeuThrTyrIleAspThrLysTyrValValHisValLysSerLeuGluThrGlu
 601 AGAAGAGCAACAGTATCTCACCTCAAGCTATATTAACATCTCCACTGATTCATTACAAGG
     GluGluGlnGlnTyrLeuThrSerSerTyrIleAsnIleSerThrAspSerLeuGlnGly
 661 TGGCAAGAAGTACTTGGTTTGGGTCCAAGCAGCAAACGCACTAGGCATGGAAGAGTCAAA
     GlyLysLysTyrLeuValTrpValGlnAlaAlaAsnAlaLeuGlyMetGluGluSerLys
 721 ACAACTGCAAATTCACCTGGATGATATAGTGATACTTTCTGCAGCCGTCATTTCCAGGGC
     GlnLeuGlnIleHisLeuAspAspIleValIleLeuSerAlaAlaValIleSerArgAla
 781 TGAGACTATAAATGCTACAGTGCCCAAGACCATAATTTATTGGGATAGTCAAACAACAAT
     GluThrIleAsnAlaThrValProLysThrIleIleTyrTrpAspSerGlnThrThrIle
 841 TGAAAAGGTTTCCTGTGAAATGAGATACAAGGCTACAACAAACCAAACTTGGAATGTTAA
     GluLysValSerCysGluMetArgTyrLysAlaThrThrAsnGlnThrTrpAsnValLys
 901 AGAATTTGACACCAATTTTACATATGTGCAACAGTCAGAATTCTACTTGGAGCCAAACAT
     GluPheAspThrAsnPheThrTyrValGlnGlnSerGluPheTyrLeuGluProAsnIle
 961 TAAGTACGTATTTCAAGTGAGATGTCAAGAAACAGGCAAAAGGTACTGGCAGCCTTGGAG
     LysTyrValPheGlnValArgCysGlnGluThrGlyLysArgTyrTrpGlnProTrpSer
1021 TTCACTGTTTTTTCATAAAACACCTGAAACAGTTCCCCAGGTCACATCAAAAGCATTCCA
     SerLeuPhePheHisLysThrProGluThrValProGlnValThrSerLysAlaPheGln
1081 ACATGACACATGGAATTCTGGGCTAACAGTTGCTTCCATCTCTACAGGGCACCTTACTTC
     HisAspThrTrpAsnSerGlyLeuThrValAlaSerIleSerThrGlyHisLeuThrSer
```

FIG. 6

```
1141  TGACAACAGAGGAGACATTGGACTTTTATTGGGAATGATCGTCTTTGCTGTTATGTTGTC
      AspAsnArgGlyAspIleGlyLeuLeuLeuGlyMetIleValPheAlaValMetLeuSer
1201  AATTCTTTCTTTGATTGGGACATTTAACAGATCATTCCGAACTGGGATTAAAAGAAGGAT
      IleLeuSerLeuIleGlyThrPheAsnArgSerPheArgThrGlyIleLysArgArgIle
1261  CTTATTGTTAATACCAAAGTGGCTTTATGAAGATATTCCTAATATGAAAAACAGCAATGT
      LeuLeuLeuIleProLysTrpLeuTyrGluAspIleProAsnMetLysAsnSerAsnVal
1321  TGTGAAAATGCTACAGGAAAATAGTGAACTTATGAATAATAATTCCAGTGAGCAGGTCCT
      ValLysMetLeuGlnGluAsnSerGluLeuMetAsnAsnAsnSerSerGluGlnValLeu
1381  ATATGTTGATCCCATGATTACAGAGATAAAAGAAATCTTCATCCCAGAACACAAGCCTAC
      TyrValAspProMetIleThrGluIleLysGluIlePheIleProGluHisLysProThr
1441  AGACTACAAGAAGGAGAATACAGGACCCCTGGAGACAAGAGACTACCCGCAAAACTCGCT
      AspTyrLysLysGluAsnThrGlyProLeuGluThrArgAspTyrProGlnAsnSerLeu
1501  ATTCGACAATACTACAGTTGTATATATTCCTGATCTCAACACTGGATATAAACCCCAAAT
      PheAspAsnThrThrValValTyrIleProAspLeuAsnThrGlyTyrLysProGlnIle
1561  TTCAAATTTTCTGCCTGAGGGAAGCCATCTCAGTAATAATAATGAAATTACTTCCTTAAC
      SerAsnPheLeuProGluGlySerHisLeuSerAsnAsnAsnGluIleThrSerLeuThr
1621  ACTTAAACCACCAGTTGATTCCTTAGACTCAGGAAATAATCCCAGGTTACAAAAGCATCC
      LeuLysProProValAspSerLeuAspSerGlyAsnAsnProArgLeuGlnLysHisPro
1681  TAATTTTGCTTTTTCTGTTTCAAGTGTGAATTCACTAAGCAACACAATATTTCTTGGAGA
      AsnPheAlaPheSerValSerSerValAsnSerLeuSerAsnThrIlePheLeuGlyGlu
1741  ATTAAGCCTCATATTAAATCAAGGAGAATGCAGTTCTCCTGACATACAAAACTCAGTAGA
      LeuSerLeuIleLeuAsnGlnGlyGluCysSerSerProAspIleGlnAsnSerValGlu
1801  GGAGGAAACCACCATGCTTTTGGAAAATGATTCACCCAGTGAAACTATTCCAGAACAGAC
      GluGluThrThrMetLeuLeuGluAsnAspSerProSerGluThrIleProGluGlnThr
1861  CCTGCTTCCTGATGAATTTGTCTCCTGTTTGGGGATCGTGAATGAGGAGTTGCCATCTAT
      LeuLeuProAspGluPheValSerCysLeuGlyIleValAsnGluGluLeuProSerIle
1921  TAATACTTATTTTCCACAAAATATTTTGGAAAGCCACTTCAATAGGATTTCACTCTTGGA
      AsnThrTyrPheProGlnAsnIleLeuGluSerHisPheAsnArgIleSerLeuLeuGlu
1981  AAAGTAGAGCTGTGTGGTCAAAATCAATATGAGAAAGCTGCCTTGCAATCTGAACTTGGG
      Lys***
2041  TTTTCCCTGCAATAGAAATTGAATTCTGCCTCTTTTTGAAAAAAATGTATTCACATCCCA
2101  AAAAAAAAAAAAAAAAAAAAAAA
```

FIG. 7

FETAL THYMUS
FETAL SPLEEN
FETAL SKELETAL MUSCLE
FETAL LUNG
FETAL LIVER
FETAL KIDNEY
FETAL HEART
FETAL BRAIN
COLON
SMALL INTESTINE
OVARY
TESTIS
PROSTATE
PANCREAS
KIDNEY
SKELETAL MUSCLE
LIVER
LUNG
PLACENTA
BRAIN
HEART
TONSIL
FETAL LIVER
BONE MARROW
PBL
THYMUS
LYMPH NODE
SPLEEN

↑
NR12 pME18S/NR12-TPOR
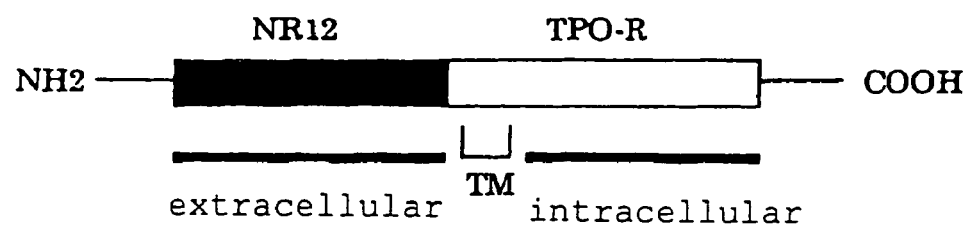
pCHO/NR12-FLAG
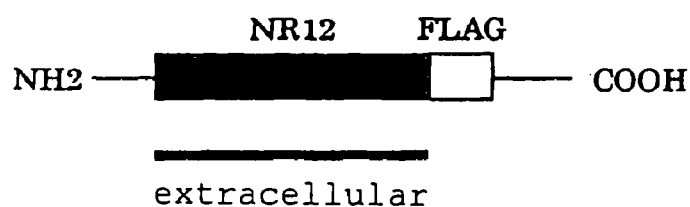
FIG. 10

```
  1  ATGAATCAGGTCACTATTCAATGGGATGCAGTAATAGCCCTTTACATACTCTTCAGCTGG
     METAsnGlnValThrIleGlnTrpAspAlaValIleAlaLeuTyrIleLeuPheSerTrp
 61  TGTCATGGAGGAATTACAAATATAAACTGCTCTGGCCACATCTGGGTAGAACCAGCCACA
     CysHisGlyGlyIleThrAsnIleAsnCysSerGlyHisIleTrpValGluProAlaThr
121  ATTTTTAAGATGGGTATGAATATCTCTATATATTGCCAAGCAGCAATTAAGAACTGCCAA
     IlePheLysMETGlyMETAsnIleSerIleTyrCysGlnAlaAlaIleLysAsnCysGln
181  CCAAGGAAACTTCATTTTTATAAAAATGGCATCAAAGAAAGATTTCAAATCACAAGGATT
     ProArgLysLeuHisPheTyrLysAsnGlyIleLysGluArgPheGlnIleThrArgIle
241  AATAAAACAACAGCTCGGCTTTGGTATAAAAACTTTCTGGAACCACATGCTTCTATGTAC
     AsnLysThrThrAlaArgLeuTrpTyrLysAsnPheLeuGluProHisAlaSerMETTyr
301  TGCACTGCTGAATGTCCCAAACATTTTCAAGAGACACTGATATGTGGAAAAGACATTTCT
     CysThrAlaGluCysProLysHisPheGlnGluThrLeuIleCysGlyLysAspIleSer
361  TCTGGATATCCGCCAGATATTCCTGATGAAGTAACCTGTGTCATTTATGAATATTCAGGC
     SerGlyTyrProProAspIleProAspGluValThrCysValIleTyrGluTyrSerGly
421  AACATGACTTGCACCTGGAATGCTGGGAAGCTCACCTACATAGACACAAAATACGTGGTA
     AsnMETThrCysThrTrpAsnAlaGlyLysLeuThrTyrIleAspThrLysTyrValVal
481  CATGTGAAGAGTTTAGAGACAGAAGAAGAGCAACAGTATCTCACCTCAAGCTATATTAAC
     HisValLysSerLeuGluThrGluGluGluGlnGlnTyrLeuThrSerSerTyrIleAsn
541  ATCTCCACTGATTCATTACAAGGTGGCAAGAAGTACTTGGTTTGGGTCCAAGCAGCAAAC
     IleSerThrAspSerLeuGlnGlyGlyLysLysTyrLeuValTrpValGlnAlaAlaAsn
601  GCACTAGGCATGGAAGAGTCAAAACAACTGCAAATTCACCTGGATGATATAGTGATACCT
     AlaLeuGlyMETGluGluSerLysGlnLeuGlnIleHisLeuAspAspIleValIlePro
661  TCTGCAGCCGTCATTTCCAGGGCTGAGACTATAAATGCTACAGTGCCCAAGACCATAATT
     SerAlaAlaValIleSerArgAlaGluThrIleAsnAlaThrValProLysThrIleIle
721  TATTGGGATAGTCAAACAACAATTGAAAAGGTTTCCTGTGAAATGAGATACAAGGCTACA
     TyrTrpAspSerGlnThrThrIleGluLysValSerCysGluMETArgTyrLysAlaThr
781  ACAAACCAAACTTGGAATGTTAAAGAATTTGACACCAATTTTACATATGTGCAACAGTCA
     ThrAsnGlnThrTrpAsnValLysGluPheAspThrAsnPheThrTyrValGlnGlnSer
841  GAATTCTACTTGGAGCCAAACATTAAGTACGTATTTCAAGTGAGATGTCAAGAAACAGGC
     GluPheTyrLeuGluProAsnIleLysTyrValPheGlnValArgCysGlnGluThrGly
901  AAAAGGTACTGGCAGCCTTGGAGTTCACTGTTTTTTCATAAAACACCTGAAACAGTTCCC
     LysArgTyrTrpGlnProTrpSerSerLeuPhePheHisLysThrProGluThrValPro
961  CAGGTCACATCAAAAGCATTCCAACATGACACATGGAATTCTGGGCTAACAGTTGCTTCC
     GlnValThrSerLysAlaPheGlnHisAspThrTrpAsnSerGlyLeuThrValAlaSer
1021 ATCTCTACAGGGCACCTTACTTCTGACAACAGAGGAGACATTGGACTTTTATTGGGAATG
     IleSerThrGlyHisLeuThrSerAspAsnArgGlyAspIleGlyLeuLeuLeuGlyMET
```

FIG. 11

1081 ATCGTCTTTGCTGTTATGTTGTCAATTCTTTCTTTGATTGGGATATTTAACAGATCATTC
     IleValPheAlaValMETLeuSerIleLeuSerLeuIleGlyIlePheAsnArgSerPhe

1141 CGAACTGGGATTAAAAGAAGGATCTTATTGTTAATACCAAAGTGGCTTTATGAAGATATT
     ArgThrGlyIleLysArgArgIleLeuLeuLeuIleProLysTrpLeuTyrGluAspIle

1201 CCTAATATGAAAAACAGCAATGTTGTGAAAATGCTACAGCCAGGTGTGGTGGTGTGCTCC
     ProAsnMETLysAsnSerAsnValValLysMETLeuGlnProGlyValValValCysSer

1261 TGTGATCCCAGCTACTTGGGAAGCTGAAGTAGGAGGACTGC
     CysAspProSerTyrLeuGlySer***

FIG. 12

```
  1   ATGAATCAGGTCACTATTCAATGGGATGCAGTAATAGCCCTTTACATACTCTTCAGCTGG
      METAsnGlnValThrIleGlnTrpAspAlaValIleAlaLeuTyrIleLeuPheSerTrp
 61   TGTCATGGAGGAATTACAAATATAAACTGCTCTGGCCACATCTGGGTAGAACCAGCCACA
      CysHisGlyGlyIleThrAsnIleAsnCysSerGlyHisIleTrpValGluProAlaThr
121   ATTTTTAAGATGGGTATGAATATCTCTATATATTGCCAAGCAGCAATTAAGAACTGCCAA
      IlePheLysMETGlyMETAsnIleSerIleTyrCysGlnAlaAlaIleLysAsnCysGln
181   CCAAGGAAACTTCATTTTTATAAAAATGGCATCAAAGAAAGATTTCAAATCACAAGGATT
      ProArgLysLeuHisPheTyrLysAsnGlyIleLysGluArgPheGlnIleThrArgIle
241   AATAAAACAACAGCTCGGCTTTGGTATAAAAACTTTCTGGAACCACATGCTTCTATGTAC
      AsnLysThrThrAlaArgLeuTrpTyrLysAsnPheLeuGluProHisAlaSerMETTyr
301   TGCACTGCTGAATGTCCCAAACATTTTCAAGAGACACTGATATGTGGAAAAGACATTTCT
      CysThrAlaGluCysProLysHisPheGlnGluThrLeuIleCysGlyLysAspIleSer
361   TCTGGATATCCGCCAGATATTCCTGATGAAGTAACCTGTGTCATTTATGAATATTCAGGC
      SerGlyTyrProProAspIleProAspGluValThrCysValIleTyrGluTyrSerGly
421   AACATGACTTGCACCTGGAATGCTGGGAAGCTCACCTACATAGACACAAAATACGTGGTA
      AsnMETThrCysThrTrpAsnAlaGlyLysLeuThrTyrIleAspThrLysTyrValVal
481   CATGTGAAGAGTTTAGAGACAGAAGAAGAGCAACAGTATCTCACCTCAAGCTATATTAAC
      HisValLysSerLeuGluThrGluGluGluGlnGlnTyrLeuThrSerSerTyrIleAsn
541   ATCTCCACTGATTCATTACAAGGTGGCAAGAAGTACTTGGTTTGGGTCCAAGCAGCAAAC
      IleSerThrAspSerLeuGlnGlyGlyLysLysTyrLeuValTrpValGlnAlaAlaAsn
601   GCACTAGGCATGGAAGAGTCAAAACAACTGCAAATTCACCTGGATGATATAGTGATACCT
      AlaLeuGlyMETGluGluSerLysGlnLeuGlnIleHisLeuAspAspIleValIlePro
661   TCTGCAGCCGTCATTTCCAGGGCTGAGACTATAAATGCTACAGTGCCCAAGACCATAATT
      SerAlaAlaValIleSerArgAlaGluThrIleAsnAlaThrValProLysThrIleIle
721   TATTGGGATAGTCAAACAACAATTGAAAAGGTTTCCTGTGAAATGAGATACAAGGCTACA
      TyrTrpAspSerGlnThrThrIleGluLysValSerCysGluMETArgTyrLysAlaThr
781   ACAAACCAAACTTGGAATGTTAAAGAATTTGACACCAATTTTACATATGTGCAACAGTCA
      ThrAsnGlnThrTrpAsnValLysGluPheAspThrAsnPheThrTyrValGlnGlnSer
841   GAATTCTACTTGGAGCCAAACATTAAGTACGTATTTCAAGTGAGATGTCAAGAAACAGGC
      GluPheTyrLeuGluProAsnIleLysTyrValPheGlnValArgCysGlnGluThrGly
901   AAAAGGTACTGGCAGCCTTGGAGTTCACTGTTTTTTCATAAAACACCTGAAACAGTTCCC
      LysArgTyrTrpGlnProTrpSerSerLeuPhePheHisLysThrProGluThrValPro
961   CAGGTCACATCAAAAGCATTCCAACATGACACATGGAATTCTGGGCTAACAGTTGCTTCC
      GlnValThrSerLysAlaPheGlnHisAspThrTrpAsnSerGlyLeuThrValAlaSer
1021  ATCTCTACAGGGCACCTTACTTCTGACAACAGAGGAGACATTGGACTTTTATTGGGAATG
      IleSerThrGlyHisLeuThrSerAspAsnArgGlyAspIleGlyLeuLeuLeuGlyMET
```

FIG. 13

1081 ATCGTCTTTGCTGTTATGTTGTCAATTCTTTCTTTGATTGGGATATTTAACAGATCATTC
     IleValPheAlaValMETLeuSerIleLeuSerLeuIleGlyIlePheAsnArgSerPhe

1141 CGAACTGGGATTAAAAGAAGGATCTTATTGTTAATACCAAAGTGGCTTTATGAAGATATT
     ArgThrGlyIleLysArgArgIleLeuLeuLeuIleProLysTrpLeuTyrGluAspIle

1201 CCTAATATGAAAAACAGCAATGTTGTGAAAATGCTACAGGAAAATAGTGAACTTATGAAT
     ProAsnMETLysAsnSerAsnValValLysMETLeuGlnGluAsnSerGluLeuMETAsn

1261 AATAATTCCAGTGAGCAGGTCCTATATGTTGATCCCATGATTACAGAGATAAAAGAAATC
     AsnAsnSerSerGluGlnValLeuTyrValAspProMETIleThrGluIleLysGluIle

1321 TTCATCCCAGAACACAAGCCTACAGACTACAAGAAGGAGAATACAGGACCCCTGGAGACA
     PheIleProGluHisLysProThrAspTyrLysLysGluAsnThrGlyProLeuGluThr

1381 AGAGACTACCCGCAAAACTCGCTATTCGACAATACTACAGTTGTATATATTCCTGATCTC
     ArgAspTyrProGlnAsnSerLeuPheAspAsnThrThrValValTyrIleProAspLeu

1441 AACACTGGATATAAACCCCAAATTTCAAATTTTCTGCCTGAGGGAAGCCATCTCAGTAAT
     AsnThrGlyTyrLysProGlnIleSerAsnPheLeuProGluGlySerHisLeuSerAsn

1501 AATAATGAAATTACTTCCTTAACACTTAAACCACCAGTTGATTCCTTAGACTCAGGAAAT
     AsnAsnGluIleThrSerLeuThrLeuLysProProValAspSerLeuAspSerGlyAsn

1561 AATCCCAGGTTACAAAAGCATCCTAATTTTGCTTTTTCTGTTTCAAGTGTGAATTCACTA
     AsnProArgLeuGlnLysHisProAsnPheAlaPheSerValSerSerValAsnSerLeu

1621 AGCAACACAATATTTCTTGGAGAATTAAGCCTCATATTAAATCAAGGAGAATGCAGTTCT
     SerAsnThrIlePheLeuGlyGluLeuSerLeuIleLeuAsnGlnGlyGluCysSerSer

1681 CCTGACATACAAAACTCAGTAGAGGAGGAAACCACCATGCTTTTGGAAAATGATTCACCC
     ProAspIleGlnAsnSerValGluGluGluThrThrMETLeuLeuGluAsnAspSerPro

1741 AGTGAAACTATTCCAGAACAGACCCTGCTTCCTGATGAATTTGTCTCCTGTTTGGGGATC
     SerGluThrIleProGluGlnThrLeuLeuProAspGluPheValSerCysLeuGlyIle

1801 GTGAATGAGGAGTTGCCATCTATTAATACTTATTTTCCACAAAATATTTTGGAAAGCCAC
     ValAsnGluGluLeuProSerIleAsnThrTyrPheProGlnAsnIleLeuGluSerHis

1861 TTCAATAGGATTTCACTCTTGGAAAAGTAGAGCTGTGTGGTCAAAATCAA
     PheAsnArgIleSerLeuLeuGluLys***

FIG. 14

SEQUENCE LISTING

```
<160> NUMBER OF SEQ ID NOS: 77

<210> SEQ ID NO 1
<211> LENGTH: 1784
<212> TYPE: DNA
<213> ORGANISM: Homo sapiens
<220> FEATURE:
<221> NAME/KEY: CDS
<222> LOCATION: (98)...(1108)

<400> SEQUENCE: 1
atgacacagc caacaagggt ggcagcctgg ctctgaagtg gaattatgtg cttcaaacag        60
gttgaaagag ggaaacagtc ttttcctgct tccagac atg aat cag gtc act att       115
                                        Met Asn Gln Val Thr Ile
                                          1               5 caa tgg gat gca gta ata gcc ctt tac ata ctc ttc agc tgg tgt cat       163
Gln Trp Asp Ala Val Ile Ala Leu Tyr Ile Leu Phe Ser Trp Cys His
                10                  15                  20 gga gga att aca aat ata aac tgc tct ggc cac atc tgg gta gaa cca       211
Gly Gly Ile Thr Asn Ile Asn Cys Ser Gly His Ile Trp Val Glu Pro
         25                  30                  35 gcc aca att ttt aag atg ggt gtg aat atc tct ata tat tgc caa gca       259
Ala Thr Ile Phe Lys Met Gly Val Asn Ile Ser Ile Tyr Cys Gln Ala
     40                  45                  50 gca att aag aac tgc caa cca agg aaa ctt cat ttt tat aaa aat ggc       307
Ala Ile Lys Asn Cys Gln Pro Arg Lys Leu His Phe Tyr Lys Asn Gly
 55                  60                  65                  70 atc aaa gaa aga ttt caa atc aca agg att aat aaa aca aca gct cgg       355
Ile Lys Glu Arg Phe Gln Ile Thr Arg Ile Asn Lys Thr Thr Ala Arg
                 75                  80                  85 ctt tgg tat aaa aac ttt ctg gaa cca cat gct tct atg tac tgc act       403
Leu Trp Tyr Lys Asn Phe Leu Glu Pro His Ala Ser Met Tyr Cys Thr
             90                  95                 100 gct gaa tgt ccc aaa cat ttt caa gag aca ctg ata tgt gga aaa gac       451
Ala Glu Cys Pro Lys His Phe Gln Glu Thr Leu Ile Cys Gly Lys Asp
        105                 110                 115 att tct tct gga tat ccg cca gat att cct gat gaa gta acc tgt gtc       499
Ile Ser Ser Gly Tyr Pro Pro Asp Ile Pro Asp Glu Val Thr Cys Val
    120                 125                 130 att tat gaa tat tca ggc aac atg act tgc acc tgg aat gct ggg agg       547
Ile Tyr Glu Tyr Ser Gly Asn Met Thr Cys Thr Trp Asn Ala Gly Arg
135                 140                 145                 150 ctc acc tac ata gac aca aaa tac gtg gta cat gtg aag agt tta gag       595
Leu Thr Tyr Ile Asp Thr Lys Tyr Val Val His Val Lys Ser Leu Glu
                155                 160                 165 aca gaa gag cag cag tat ctc acc tca agc tat att aac atc tcc       643
Thr Glu Glu Glu Gln Gln Tyr Leu Thr Ser Ser Tyr Ile Asn Ile Ser
            170                 175                 180 act gat tca tta caa ggt ggc aag aag tac ttg gtt tgg gtc caa gca       691
Thr Asp Ser Leu Gln Gly Gly Lys Lys Tyr Leu Val Trp Val Gln Ala
```

```
                185                 190                 195
gca aac gca cta ggc atg gaa gag tca aaa caa ctg caa att cac ctg      739
Ala Asn Ala Leu Gly Met Glu Glu Ser Lys Gln Leu Gln Ile His Leu
        200                 205                 210 gat gat ata gtg ata ctt tct gca gcc gtc att tcc agg gct gag act      787
Asp Asp Ile Val Ile Leu Ser Ala Ala Val Ile Ser Arg Ala Glu Thr
215                 220                 225                 230 ata aat gct aca gtg ccc aag acc ata att tat tgg gat agt caa aca      835
Ile Asn Ala Thr Val Pro Lys Thr Ile Ile Tyr Trp Asp Ser Gln Thr
                235                 240                 245 aca att gaa aag gtt tcc tgt gaa atg aga tac aag gct aca aca aac      883
Thr Ile Glu Lys Val Ser Cys Glu Met Arg Tyr Lys Ala Thr Thr Asn
            250                 255                 260 caa act tgg aat gtt aaa gaa ttt gac acc aat ttt aca tat gtg caa      931
Gln Thr Trp Asn Val Lys Glu Phe Asp Thr Asn Phe Thr Tyr Val Gln
            265                 270                 275 cag tca gaa ttc tac ttg gag cca aac att aag tac gta ttt caa gtg      979
Gln Ser Glu Phe Tyr Leu Glu Pro Asn Ile Lys Tyr Val Phe Gln Val
        280                 285                 290 aga tgt caa gaa aca ggc aaa agg tac tgg cag cct tgg agt tca ctg     1027
Arg Cys Gln Glu Thr Gly Lys Arg Tyr Trp Gln Pro Trp Ser Ser Leu
295                 300                 305                 310 ttt ttt cat aaa aca cct gaa aca ggt gag tgt act tat ata ttt tat     1075
Phe Phe His Lys Thr Pro Glu Thr Gly Glu Cys Thr Tyr Ile Phe Tyr
                315                 320                 325 tct gtt ggg ctt ttc ttt ata tat ctt ttc tgc tgagcacagt ggctcacgcc   1128
Ser Val Gly Leu Phe Phe Ile Tyr Leu Phe Cys
            330                 335 tgtaattcca gcactttgag aggccaaggc aggaagattg cttgagccta ggagtttgag   1188
actggcctgg gcaacatggt gagaccctag tctgtacaga aaataataa ttattattag    1248 cctgggtggt ggaatgcatt tgtagtcgca gctacttggg aggctgaggt agtaggattg   1308
cgtgagcccg ggagtttgat gctgcagtga gctatgatca tcccactgct ctctagcctg   1368
gaggaaagac caagaccctg tttcctaaaa agtttaaaac agccaggtgc agtggcttat   1428
gtctgtaatc ccagcacttt gggaggccaa ggtgggtgga ttaccttagg tcaggacttc   1488
aagacctcct cggccgacat ggtgaaaccc tgtctctact aaaaatacga aaattagctg   1548
ggcatggtgg caggtgcctg taatctcagc tactcggaag gctgaggcag gaaaattgct   1608
tgaacccaag aagtggaggt tgcagtgaac tgagattgta ccaccgcact ccagcctggc   1668
caagagagag agacttggtc tcaaaaaaaa ataaaaataa aaataataat aataaataag   1728
ttaaaaacaa ataaagcta caagataaaa aaaaaaaaa aaaaaaaaaa aaaaaa         1784

<210> SEQ ID NO 2
<211> LENGTH: 337
<212> TYPE: PRT
<213> ORGANISM: Homo sapiens

<400> SEQUENCE: 2

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Val Asn Ile
        35                  40                  45

Ser Ile Tyr Cys Gln Ala Ala Ile Lys Asn Cys Gln Pro Arg Lys Leu
    50                  55                  60
```

-continued

```
His Phe Tyr Lys Asn Gly Ile Lys Glu Arg Phe Gln Ile Thr Arg Ile
 65                  70                  75                  80

Asn Lys Thr Thr Ala Arg Leu Trp Tyr Lys Asn Phe Leu Glu Pro His
                 85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Arg Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Leu Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Gly Glu
305                 310                 315                 320

Cys Thr Tyr Ile Phe Tyr Ser Val Gly Leu Phe Phe Ile Tyr Leu Phe
                325                 330                 335

Cys
```

<210> SEQ ID NO 3
<211> LENGTH: 1479
<212> TYPE: DNA
<213> ORGANISM: Homo sapiens
<220> FEATURE:
<221> NAME/KEY: CDS
<222> LOCATION: (98)...(1381)

<400> SEQUENCE: 3

```
atgacacagc caacaagggt ggcagcctgg ctctgaagtg gaattatgtg cttcaaacag      60
gttgaaagag ggaaacagtc ttttcctgct tccagac atg aat cag gtc act att     115
                                      Met Asn Gln Val Thr Ile
                                        1               5 caa tgg gat gca gta ata gcc ctt tac ata ctc ttc agc tgg tgt cat      163
Gln Trp Asp Ala Val Ile Ala Leu Tyr Ile Leu Phe Ser Trp Cys His
         10                  15                  20 gga gga att aca aat ata aac tgc tct ggc cac atc tgg gta gaa cca      211
Gly Gly Ile Thr Asn Ile Asn Cys Ser Gly His Ile Trp Val Glu Pro
     25                  30                  35
```

```
gcc aca att ttt aag atg ggt gtg aat atc tct ata tat tgc caa gca      259
Ala Thr Ile Phe Lys Met Gly Val Asn Ile Ser Ile Tyr Cys Gln Ala
    40                  45                  50 gca att aag aac tgc caa cca agg aaa ctt cat ttt tat aaa aat ggc      307
Ala Ile Lys Asn Cys Gln Pro Arg Lys Leu His Phe Tyr Lys Asn Gly
55                  60                  65                  70 atc aaa gaa aga ttt caa atc aca agg att aat aaa aca aca gct cgg      355
Ile Lys Glu Arg Phe Gln Ile Thr Arg Ile Asn Lys Thr Thr Ala Arg
                75                  80                  85 ctt tgg tat aaa aac ttt ctg gaa cca cat gct tct atg tac tgc act      403
Leu Trp Tyr Lys Asn Phe Leu Glu Pro His Ala Ser Met Tyr Cys Thr
            90                  95                  100 gct gaa tgt ccc aaa cat ttt caa gag aca ctg ata tgt gga aaa gac      451
Ala Glu Cys Pro Lys His Phe Gln Glu Thr Leu Ile Cys Gly Lys Asp
        105                 110                 115 att tct tct gga tat ccg cca gat att cct gat gaa gta acc tgt gtc      499
Ile Ser Ser Gly Tyr Pro Pro Asp Ile Pro Asp Glu Val Thr Cys Val
120                 125                 130 att tat gaa tat tca ggc aac atg act tgc acc tgg aat gct ggg agg      547
Ile Tyr Glu Tyr Ser Gly Asn Met Thr Cys Thr Trp Asn Ala Gly Arg
135                 140                 145                 150 ctc acc tac ata gac aca aaa tac gtg gta cat gtg aag agt tta gag      595
Leu Thr Tyr Ile Asp Thr Lys Tyr Val Val His Val Lys Ser Leu Glu
                155                 160                 165 aca gaa gaa gag caa cag tat ctc acc tca agc tat att aac atc tcc      643
Thr Glu Glu Glu Gln Gln Tyr Leu Thr Ser Ser Tyr Ile Asn Ile Ser
            170                 175                 180 act gat tca tta caa ggt ggc aag aag tac ttg gtt tgg gtc caa gca      691
Thr Asp Ser Leu Gln Gly Gly Lys Lys Tyr Leu Val Trp Val Gln Ala
        185                 190                 195 gca aac gca cta ggc atg gaa gag tca aaa caa ctg caa att cac ctg      739
Ala Asn Ala Leu Gly Met Glu Glu Ser Lys Gln Leu Gln Ile His Leu
200                 205                 210 gat gat ata gtg ata ctt tct gca gcc gtc att tcc agg gct gag act      787
Asp Asp Ile Val Ile Leu Ser Ala Ala Val Ile Ser Arg Ala Glu Thr
215                 220                 225                 230 ata aat gct aca gtg ccc aag acc ata att tat tgg gat agt caa aca      835
Ile Asn Ala Thr Val Pro Lys Thr Ile Ile Tyr Trp Asp Ser Gln Thr
                235                 240                 245 aca att gaa aag gtt tcc tgt gaa atg aga tac aag gct aca aca aac      883
Thr Ile Glu Lys Val Ser Cys Glu Met Arg Tyr Lys Ala Thr Thr Asn
            250                 255                 260 caa act tgg aat gtt aaa gaa ttt gac acc aat ttt aca tat gtg caa      931
Gln Thr Trp Asn Val Lys Glu Phe Asp Thr Asn Phe Thr Tyr Val Gln
        265                 270                 275 cag tca gaa ttc tac ttg gag cca aac att aag tac gta ttt caa gtg      979
Gln Ser Glu Phe Tyr Leu Glu Pro Asn Ile Lys Tyr Val Phe Gln Val
280                 285                 290 aga tgt caa gaa aca ggc aaa agg tac tgg cag cct tgg agt tca ctg     1027
Arg Cys Gln Glu Thr Gly Lys Arg Tyr Trp Gln Pro Trp Ser Ser Leu
295                 300                 305                 310 ttt ttt cat aaa aca cct gaa aca gtt ccc cag gtc aca tca aaa gca     1075
Phe Phe His Lys Thr Pro Glu Thr Val Pro Gln Val Thr Ser Lys Ala
                315                 320                 325 ttc caa cat gac aca tgg aat tct ggg cta aca gtt gct tcc atc tct     1123
Phe Gln His Asp Thr Trp Asn Ser Gly Leu Thr Val Ala Ser Ile Ser
            330                 335                 340 aca ggg cac ctt act tct gac aac aga gga gac att gga ctt tta ttg     1171
Thr Gly His Leu Thr Ser Asp Asn Arg Gly Asp Ile Gly Leu Leu Leu
        345                 350                 355
```

-continued

```
gga atg atc gtc ttt gct gtt atg ttg tca att ctt tct ttg att ggg   1219
Gly Met Ile Val Phe Ala Val Met Leu Ser Ile Leu Ser Leu Ile Gly
    360                 365                 370 ata ttt aac aga tca ttc cga act ggg att aaa aga agg atc tta ttg   1267
Ile Phe Asn Arg Ser Phe Arg Thr Gly Ile Lys Arg Arg Ile Leu Leu
375                 380                 385                 390 tta ata cca aag tgg ctt tat gaa gat att cct aat atg aaa aac agc   1315
Leu Ile Pro Lys Trp Leu Tyr Glu Asp Ile Pro Asn Met Lys Asn Ser
            395                 400                 405 aat gtt gtg aaa atg cta cag cca ggt gtg gtg gtg tgc tcc tgt gat   1363
Asn Val Val Lys Met Leu Gln Pro Gly Val Val Val Cys Ser Cys Asp
        410                 415                 420 ccc agc tac ttg gga agc tgaagtagga ggactgcttg agcccaggag          1411
Pro Ser Tyr Leu Gly Ser
                425 tccaacacca gcttcacaac ataccaagac cctgtctcaa aaaaaaaaaa aaaaaaaaaa  1471 aaaaaaaa                                                           1479

<210> SEQ ID NO 4
<211> LENGTH: 428
<212> TYPE: PRT
<213> ORGANISM: Homo sapiens

<400> SEQUENCE: 4

Met Asn Gln Val Thr Ile Gln Trp Asp Ala Val Ile Ala Leu Tyr Ile
 1               5                  10                  15

Leu Phe Ser Trp Cys His Gly Gly Ile Thr Asn Ile Asn Cys Ser Gly
                20                  25                  30

His Ile Trp Val Glu Pro Ala Thr Ile Phe Lys Met Gly Val Asn Ile
            35                  40                  45

Ser Ile Tyr Cys Gln Ala Ala Ile Lys Asn Cys Gln Pro Arg Lys Leu
        50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
130                 135                 140

Thr Trp Asn Ala Gly Arg Leu Thr Tyr Ile Asp Thr Lys Tyr Val Val
145                 150                 155                 160

His Val Lys Ser Leu Glu Thr Glu Glu Gln Gln Tyr Leu Thr Ser Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Leu Ser Ala Ala Val
210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
```

-continued

```
                245                 250                 255
Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
    370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Pro Gly Val
                405                 410                 415

Val Val Cys Ser Cys Asp Pro Ser Tyr Leu Gly Ser
            420                 425
```

```
<210> SEQ ID NO 5
<211> LENGTH: 2123
<212> TYPE: DNA
<213> ORGANISM: Homo sapiens
<220> FEATURE:
<221> NAME/KEY: CDS
<222> LOCATION: (98)...(1984)

<400> SEQUENCE: 5
atgacacagc caacaagggt ggcagcctgg ctctgaagtg gaattatgtg cttcaaacag      60
gttgaaagag ggaaacagtc ttttcctgct tccagac atg aat cag gtc act att     115
                                        Met Asn Gln Val Thr Ile
                                        1               5 caa tgg gat gca gta ata gcc ctt tac ata ctc ttc agc tgg tgt cat      163
Gln Trp Asp Ala Val Ile Ala Leu Tyr Ile Leu Phe Ser Trp Cys His
        10                  15                  20 gga gga att aca aat ata aac tgc tct ggc cac atc tgg gta gaa cca      211
Gly Gly Ile Thr Asn Ile Asn Cys Ser Gly His Ile Trp Val Glu Pro
    25                  30                  35 gcc aca att ttt aag atg ggt gtg aat atc tct ata tat tgc caa gca      259
Ala Thr Ile Phe Lys Met Gly Val Asn Ile Ser Ile Tyr Cys Gln Ala
40                  45                  50 gca att aag aac tgc caa cca agg aaa ctt cat ttt tat aaa aat ggc      307
Ala Ile Lys Asn Cys Gln Pro Arg Lys Leu His Phe Tyr Lys Asn Gly
55                  60                  65                  70 atc aaa gaa aga ttt caa atc aca agg att aat aaa aca aca gct cgg      355
Ile Lys Glu Arg Phe Gln Ile Thr Arg Ile Asn Lys Thr Thr Ala Arg
            75                  80                  85 ctt tgg tat aaa aac ttt ctg gaa cca cat gct tct atg tac tgc act      403
Leu Trp Tyr Lys Asn Phe Leu Glu Pro His Ala Ser Met Tyr Cys Thr
        90                  95                 100 gct gaa tgt ccc aaa cat ttt caa gag aca ctg ata tgt gga aaa gac      451
Ala Glu Cys Pro Lys His Phe Gln Glu Thr Leu Ile Cys Gly Lys Asp
    105                 110                 115
```

-continued

| | |
|---|---|
| att tct tct gga tat ccg cca gat att cct gat gaa gta acc tgt gtc<br>Ile Ser Ser Gly Tyr Pro Pro Asp Ile Pro Asp Glu Val Thr Cys Val<br>120                        125                    130 | 499 |
| att tat gaa tat tca ggc aac atg act tgc acc tgg aat gct ggg agg<br>Ile Tyr Glu Tyr Ser Gly Asn Met Thr Cys Thr Trp Asn Ala Gly Arg<br>135                    140                    145                    150 | 547 |
| ctc acc tac ata gac aca aaa tac gtg gta cat gtg aag agt tta gag<br>Leu Thr Tyr Ile Asp Thr Lys Tyr Val Val His Val Lys Ser Leu Glu<br>                    155                    160                    165 | 595 |
| aca gaa gaa gag caa cag tat ctc acc tca agc tat att aac atc tcc<br>Thr Glu Glu Glu Gln Gln Tyr Leu Thr Ser Ser Tyr Ile Asn Ile Ser<br>170                        175                    180 | 643 |
| act gat tca tta caa ggt ggc aag aag tac ttg gtt tgg gtc caa gca<br>Thr Asp Ser Leu Gln Gly Gly Lys Lys Tyr Leu Val Trp Val Gln Ala<br>                    185                    190                    195 | 691 |
| gca aac gca cta ggc atg gaa gag tca aaa caa ctg caa att cac ctg<br>Ala Asn Ala Leu Gly Met Glu Glu Ser Lys Gln Leu Gln Ile His Leu<br>200                        205                    210 | 739 |
| gat gat ata gtg ata ctt tct gca gcc gtc att tcc agg gct gag act<br>Asp Asp Ile Val Ile Leu Ser Ala Ala Val Ile Ser Arg Ala Glu Thr<br>215                        220                    225                    230 | 787 |
| ata aat gct aca gtg ccc aag acc ata att tat tgg gat agt caa aca<br>Ile Asn Ala Thr Val Pro Lys Thr Ile Ile Tyr Trp Asp Ser Gln Thr<br>                    235                    240                    245 | 835 |
| aca att gaa aag gtt tcc tgt gaa atg aga tac aag gct aca aca aac<br>Thr Ile Glu Lys Val Ser Cys Glu Met Arg Tyr Lys Ala Thr Thr Asn<br>250                        255                    260 | 883 |
| caa act tgg aat gtt aaa gaa ttt gac acc aat ttt aca tat gtg caa<br>Gln Thr Trp Asn Val Lys Glu Phe Asp Thr Asn Phe Thr Tyr Val Gln<br>                    265                    270                    275 | 931 |
| cag tca gaa ttc tac ttg gag cca aac att aag tac gta ttt caa gtg<br>Gln Ser Glu Phe Tyr Leu Glu Pro Asn Ile Lys Tyr Val Phe Gln Val<br>280                        285                    290 | 979 |
| aga tgt caa gaa aca ggc aaa agg tac tgg cag cct tgg agt tca ctg<br>Arg Cys Gln Glu Thr Gly Lys Arg Tyr Trp Gln Pro Trp Ser Ser Leu<br>295                        300                    305                    310 | 1027 |
| ttt ttt cat aaa aca cct gaa aca gtt ccc cag gtc aca tca aaa gca<br>Phe Phe His Lys Thr Pro Glu Thr Val Pro Gln Val Thr Ser Lys Ala<br>                    315                    320                    325 | 1075 |
| ttc caa cat gac aca tgg aat tct ggg cta aca gtt gct tcc atc tct<br>Phe Gln His Asp Thr Trp Asn Ser Gly Leu Thr Val Ala Ser Ile Ser<br>                    330                    335                    340 | 1123 |
| aca ggg cac ctt act tct gac aac aga gga gac att gga ctt tta ttg<br>Thr Gly His Leu Thr Ser Asp Asn Arg Gly Asp Ile Gly Leu Leu Leu<br>                    345                    350                    355 | 1171 |
| gga atg atc gtc ttt gct gtt atg ttg tca att ctt tct ttg att ggg<br>Gly Met Ile Val Phe Ala Val Met Leu Ser Ile Leu Ser Leu Ile Gly<br>360                        365                    370 | 1219 |
| aca ttt aac aga tca ttc cga act ggg att aaa aga agg atc tta ttg<br>Thr Phe Asn Arg Ser Phe Arg Thr Gly Ile Lys Arg Arg Ile Leu Leu<br>375                        380                    385                    390 | 1267 |
| tta ata cca aag tgg ctt tat gaa gat att cct aat atg aaa aac agc<br>Leu Ile Pro Lys Trp Leu Tyr Glu Asp Ile Pro Asn Met Lys Asn Ser<br>                    395                    400                    405 | 1315 |
| aat gtt gtg aaa atg cta cag gaa aat agt gaa ctt atg aat aat aat<br>Asn Val Val Lys Met Leu Gln Glu Asn Ser Glu Leu Met Asn Asn Asn<br>                    410                    415                    420 | 1363 |
| tcc agt gag cag gtc cta tat gtt gat ccc atg att aca gag ata aaa<br>Ser Ser Glu Gln Val Leu Tyr Val Asp Pro Met Ile Thr Glu Ile Lys | 1411 |

```
                    425                 430                 435
gaa atc ttc atc cca gaa cac aag cct aca gac tac aag aag gag aat    1459
Glu Ile Phe Ile Pro Glu His Lys Pro Thr Asp Tyr Lys Lys Glu Asn
        440                 445                 450 aca gga ccc ctg gag aca aga gac tac ccg caa aac tcg cta ttc gac    1507
Thr Gly Pro Leu Glu Thr Arg Asp Tyr Pro Gln Asn Ser Leu Phe Asp
455                 460                 465                 470 aat act aca gtt gta tat att cct gat ctc aac act gga tat aaa ccc    1555
Asn Thr Thr Val Val Tyr Ile Pro Asp Leu Asn Thr Gly Tyr Lys Pro
                475                 480                 485 caa att tca aat ttt ctg cct gag gga agc cat ctc agt aat aat aat    1603
Gln Ile Ser Asn Phe Leu Pro Glu Gly Ser His Leu Ser Asn Asn Asn
            490                 495                 500 gaa att act tcc tta aca ctt aaa cca cca gtt gat tcc tta gac tca    1651
Glu Ile Thr Ser Leu Thr Leu Lys Pro Pro Val Asp Ser Leu Asp Ser
        505                 510                 515 gga aat aat ccc agg tta caa aag cat cct aat ttt gct ttt tct gtt    1699
Gly Asn Asn Pro Arg Leu Gln Lys His Pro Asn Phe Ala Phe Ser Val
    520                 525                 530 tca agt gtg aat tca cta agc aac aca ata ttt ctt gga gaa tta agc    1747
Ser Ser Val Asn Ser Leu Ser Asn Thr Ile Phe Leu Gly Glu Leu Ser
535                 540                 545                 550 ctc ata tta aat caa gga gaa tgc agt tct cct gac ata caa aac tca    1795
Leu Ile Leu Asn Gln Gly Glu Cys Ser Ser Pro Asp Ile Gln Asn Ser
                555                 560                 565 gta gag gag gaa acc acc atg ctt ttg gaa aat gat tca ccc agt gaa    1843
Val Glu Glu Glu Thr Thr Met Leu Leu Glu Asn Asp Ser Pro Ser Glu
            570                 575                 580 act att cca gaa cag acc ctg ctt cct gat gaa ttt gtc tcc tgt ttg    1891
Thr Ile Pro Glu Gln Thr Leu Leu Pro Asp Glu Phe Val Ser Cys Leu
        585                 590                 595 ggg atc gtg aat gag gag ttg cca tct att aat act tat ttt cca caa    1939
Gly Ile Val Asn Glu Glu Leu Pro Ser Ile Asn Thr Tyr Phe Pro Gln
    600                 605                 610 aat att ttg gaa agc cac ttc aat agg att tca ctc ttg gaa aag          1984
Asn Ile Leu Glu Ser His Phe Asn Arg Ile Ser Leu Leu Glu Lys
615                 620                 625 tagagctgtg tggtcaaaat caatatgaga aagctgcctt gcaatctgaa cttgggtttt    2044
ccctgcaata gaaattgaat tctgcctctt tttgaaaaaa atgtattcac atcccaaaaa    2104
aaaaaaaaaa aaaaaaaaa                                                 2123

<210> SEQ ID NO 6
<211> LENGTH: 629
<212> TYPE: PRT
<213> ORGANISM: Homo sapiens

<400> SEQUENCE: 6

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Val Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80
```

```
Asn Lys Thr Thr Ala Arg Leu Trp Tyr Lys Asn Phe Leu Glu Pro His
                85                  90                  95
Ala Ser Met Tyr Cys Thr Ala Glu Cys Pro Lys His Phe Gln Glu Thr
            100                 105                 110
Leu Ile Cys Gly Lys Asp Ile Ser Ser Gly Tyr Pro Pro Asp Ile Pro
        115                 120                 125
Asp Glu Val Thr Cys Val Ile Tyr Glu Tyr Ser Gly Asn Met Thr Cys
    130                 135                 140
Thr Trp Asn Ala Gly Arg Leu Thr Tyr Ile Asp Thr Lys Tyr Val Val
145                 150                 155                 160
His Val Lys Ser Leu Glu Thr Glu Glu Gln Gln Tyr Leu Thr Ser
                165                 170                 175
Ser Tyr Ile Asn Ile Ser Thr Asp Ser Leu Gln Gly Gly Lys Lys Tyr
            180                 185                 190
Leu Val Trp Val Gln Ala Ala Asn Ala Leu Gly Met Glu Glu Ser Lys
        195                 200                 205
Gln Leu Gln Ile His Leu Asp Asp Ile Val Ile Leu Ser Ala Ala Val
    210                 215                 220
Ile Ser Arg Ala Glu Thr Ile Asn Ala Thr Val Pro Lys Thr Ile Ile
225                 230                 235                 240
Tyr Trp Asp Ser Gln Thr Thr Ile Glu Lys Val Ser Cys Glu Met Arg
                245                 250                 255
Tyr Lys Ala Thr Thr Asn Gln Thr Trp Asn Val Lys Glu Phe Asp Thr
            260                 265                 270
Asn Phe Thr Tyr Val Gln Gln Ser Glu Phe Tyr Leu Glu Pro Asn Ile
        275                 280                 285
Lys Tyr Val Phe Gln Val Arg Cys Gln Glu Thr Gly Lys Arg Tyr Trp
    290                 295                 300
Gln Pro Trp Ser Ser Leu Phe Phe His Lys Thr Pro Glu Thr Val Pro
305                 310                 315                 320
Gln Val Thr Ser Lys Ala Phe Gln His Asp Thr Trp Asn Ser Gly Leu
                325                 330                 335
Thr Val Ala Ser Ile Ser Thr Gly His Leu Thr Ser Asp Asn Arg Gly
            340                 345                 350
Asp Ile Gly Leu Leu Leu Gly Met Ile Val Phe Ala Val Met Leu Ser
        355                 360                 365
Ile Leu Ser Leu Ile Gly Thr Phe Asn Arg Ser Phe Arg Thr Gly Ile
    370                 375                 380
Lys Arg Arg Ile Leu Leu Leu Ile Pro Lys Trp Leu Tyr Glu Asp Ile
385                 390                 395                 400
Pro Asn Met Lys Asn Ser Asn Val Val Lys Met Leu Gln Glu Asn Ser
                405                 410                 415
Glu Leu Met Asn Asn Asn Ser Ser Glu Gln Val Leu Tyr Val Asp Pro
            420                 425                 430
Met Ile Thr Glu Ile Lys Glu Ile Phe Ile Pro Glu His Lys Pro Thr
        435                 440                 445
Asp Tyr Lys Lys Glu Asn Thr Gly Pro Leu Glu Thr Arg Asp Tyr Pro
    450                 455                 460
Gln Asn Ser Leu Phe Asp Asn Thr Thr Val Val Tyr Ile Pro Asp Leu
465                 470                 475                 480
Asn Thr Gly Tyr Lys Pro Gln Ile Ser Asn Phe Leu Pro Glu Gly Ser
                485                 490                 495
His Leu Ser Asn Asn Asn Glu Ile Thr Ser Leu Thr Leu Lys Pro Pro
```

```
                    500                 505                 510
Val Asp Ser Leu Asp Ser Gly Asn Asn Pro Arg Leu Gln Lys His Pro
            515                 520                 525

Asn Phe Ala Phe Ser Val Ser Val Asn Ser Leu Ser Asn Thr Ile
        530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
            565                 570                 575

Asn Asp Ser Pro Ser Glu Thr Ile Pro Glu Gln Thr Leu Leu Pro Asp
        580                 585                 590

Glu Phe Val Ser Cys Leu Gly Ile Val Asn Glu Glu Leu Pro Ser Ile
            595                 600                 605

Asn Thr Tyr Phe Pro Gln Asn Ile Leu Glu Ser His Phe Asn Arg Ile
        610                 615                 620

Ser Leu Leu Glu Lys
625

<210> SEQ ID NO 7
<211> LENGTH: 1301
<212> TYPE: DNA
<213> ORGANISM: Homo sapiens
<220> FEATURE:
<221> NAME/KEY: CDS
<222> LOCATION: (1)...(1284)

<400> SEQUENCE: 7 atg aat cag gtc act att caa tgg gat gca gta ata gcc ctt tac ata        48
Met Asn Gln Val Thr Ile Gln Trp Asp Ala Val Ile Ala Leu Tyr Ile
1               5                   10                  15 ctc ttc agc tgg tgt cat gga gga att aca aat ata aac tgc tct ggc        96
Leu Phe Ser Trp Cys His Gly Gly Ile Thr Asn Ile Asn Cys Ser Gly
                20                  25                  30 cac atc tgg gta gaa cca gcc aca att ttt aag atg ggt atg aat atc       144
His Ile Trp Val Glu Pro Ala Thr Ile Phe Lys Met Gly Met Asn Ile
            35                  40                  45 tct ata tat tgc caa gca gca att aag aac tgc caa cca agg aaa ctt       192
Ser Ile Tyr Cys Gln Ala Ala Ile Lys Asn Cys Gln Pro Arg Lys Leu
        50                  55                  60 cat ttt tat aaa aat ggc atc aaa gaa aga ttt caa atc aca agg att       240
His Phe Tyr Lys Asn Gly Ile Lys Glu Arg Phe Gln Ile Thr Arg Ile
65                  70                  75                  80 aat aaa aca aca gct cgg ctt tgg tat aaa aac ttt ctg gaa cca cat       288
Asn Lys Thr Thr Ala Arg Leu Trp Tyr Lys Asn Phe Leu Glu Pro His
                85                  90                  95 gct tct atg tac tgc act gct gaa tgt ccc aaa cat ttt caa gag aca       336
Ala Ser Met Tyr Cys Thr Ala Glu Cys Pro Lys His Phe Gln Glu Thr
                100                 105                 110 ctg ata tgt gga aaa gac att tct tct gga tat ccg cca gat att cct       384
Leu Ile Cys Gly Lys Asp Ile Ser Ser Gly Tyr Pro Pro Asp Ile Pro
            115                 120                 125 gat gaa gta acc tgt gtc att tat gaa tat tca ggc aac atg act tgc       432
Asp Glu Val Thr Cys Val Ile Tyr Glu Tyr Ser Gly Asn Met Thr Cys
        130                 135                 140 acc tgg aat gct ggg aag ctc acc tac ata gac aca aaa tac gtg gta       480
Thr Trp Asn Ala Gly Lys Leu Thr Tyr Ile Asp Thr Lys Tyr Val Val
145                 150                 155                 160 cat gtg aag agt tta gag aca gaa gaa gag caa cag tat ctc acc tca       528
His Val Lys Ser Leu Glu Thr Glu Glu Glu Gln Gln Tyr Leu Thr Ser
```

```
                    165                 170                 175
agc tat att aac atc tcc act gat tca tta caa ggt ggc aag aag tac       576
Ser Tyr Ile Asn Ile Ser Thr Asp Ser Leu Gln Gly Gly Lys Lys Tyr
            180                 185                 190 ttg gtt tgg gtc caa gca gca aac gca cta ggc atg gaa gag tca aaa       624
Leu Val Trp Val Gln Ala Ala Asn Ala Leu Gly Met Glu Glu Ser Lys
        195                 200                 205 caa ctg caa att cac ctg gat gat ata gtg ata cct tct gca gcc gtc       672
Gln Leu Gln Ile His Leu Asp Asp Ile Val Ile Pro Ser Ala Ala Val
    210                 215                 220 att tcc agg gct gag act ata aat gct aca gtg ccc aag acc ata att       720
Ile Ser Arg Ala Glu Thr Ile Asn Ala Thr Val Pro Lys Thr Ile Ile
225                 230                 235                 240 tat tgg gat agt caa aca aca att gaa aag gtt tcc tgt gaa atg aga       768
Tyr Trp Asp Ser Gln Thr Thr Ile Glu Lys Val Ser Cys Glu Met Arg
                245                 250                 255 tac aag gct aca aca aac caa act tgg aat gtt aaa gaa ttt gac acc       816
Tyr Lys Ala Thr Thr Asn Gln Thr Trp Asn Val Lys Glu Phe Asp Thr
            260                 265                 270 aat ttt aca tat gtg caa cag tca gaa ttc tac ttg gag cca aac att       864
Asn Phe Thr Tyr Val Gln Gln Ser Glu Phe Tyr Leu Glu Pro Asn Ile
        275                 280                 285 aag tac gta ttt caa gtg aga tgt caa gaa aca ggc aaa agg tac tgg       912
Lys Tyr Val Phe Gln Val Arg Cys Gln Glu Thr Gly Lys Arg Tyr Trp
    290                 295                 300 cag cct tgg agt tca ctg ttt ttt cat aaa aca cct gaa aca gtt ccc       960
Gln Pro Trp Ser Ser Leu Phe Phe His Lys Thr Pro Glu Thr Val Pro
305                 310                 315                 320 cag gtc aca tca aaa gca ttc caa cat gac aca tgg aat tct ggg cta      1008
Gln Val Thr Ser Lys Ala Phe Gln His Asp Thr Trp Asn Ser Gly Leu
                325                 330                 335 aca gtt gct tcc atc tct aca ggg cac ctt act tct gac aac aga gga      1056
Thr Val Ala Ser Ile Ser Thr Gly His Leu Thr Ser Asp Asn Arg Gly
            340                 345                 350 gac att gga ctt tta ttg gga atg atc gtc ttt gct gtt atg ttg tca      1104
Asp Ile Gly Leu Leu Leu Gly Met Ile Val Phe Ala Val Met Leu Ser
        355                 360                 365 att ctt tct ttg att ggg ata ttt aac aga tca ttc cga act ggg att      1152
Ile Leu Ser Leu Ile Gly Ile Phe Asn Arg Ser Phe Arg Thr Gly Ile
    370                 375                 380 aaa aga agg atc tta ttg tta ata cca aag tgg ctt tat gaa gat att      1200
Lys Arg Arg Ile Leu Leu Leu Ile Pro Lys Trp Leu Tyr Glu Asp Ile
385                 390                 395                 400 cct aat atg aaa aac agc aat gtt gtg aaa atg cta cag cca ggt gtg      1248
Pro Asn Met Lys Asn Ser Asn Val Val Lys Met Leu Gln Pro Gly Val
                405                 410                 415 gtg gtg tgc tcc tgt gat ccc agc tac ttg gga agc tgaagtagga           1294
Val Val Cys Ser Cys Asp Pro Ser Tyr Leu Gly Ser
            420                 425 ggactgc                                                               1301

<210> SEQ ID NO 8
<211> LENGTH: 428
<212> TYPE: PRT
<213> ORGANISM: Homo sapiens

<400> SEQUENCE: 8

Met Asn Gln Val Thr Ile Gln Trp Asp Ala Val Ile Ala Leu Tyr Ile
 1               5                  10                  15
```

-continued

```
Leu Phe Ser Trp Cys His Gly Gly Ile Thr Asn Ile Asn Cys Ser Gly
         20                  25                  30

His Ile Trp Val Glu Pro Ala Thr Ile Phe Lys Met Gly Met Asn Ile
             35                  40                  45

Ser Ile Tyr Cys Gln Ala Ala Ile Lys Asn Cys Gln Pro Arg Lys Leu
 50                  55                  60

His Phe Tyr Lys Asn Gly Ile Lys Glu Arg Phe Gln Ile Thr Arg Ile
 65                  70                  75                  80

Asn Lys Thr Thr Ala Arg Leu Trp Tyr Lys Asn Phe Leu Glu Pro His
                 85                  90                  95

Ala Ser Met Tyr Cys Thr Ala Glu Cys Pro Lys His Phe Gln Glu Thr
                100                 105                 110

Leu Ile Cys Gly Lys Asp Ile Ser Ser Gly Tyr Pro Pro Asp Ile Pro
            115                 120                 125

Asp Glu Val Thr Cys Val Ile Tyr Glu Tyr Ser Gly Asn Met Thr Cys
        130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
                180                 185                 190

Leu Val Trp Val Gln Ala Ala Asn Ala Leu Gly Met Glu Glu Ser Lys
            195                 200                 205

Gln Leu Gln Ile His Leu Asp Asp Ile Val Ile Pro Ser Ala Ala Val
        210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
                260                 265                 270

Asn Phe Thr Tyr Val Gln Gln Ser Glu Phe Tyr Leu Glu Pro Asn Ile
            275                 280                 285

Lys Tyr Val Phe Gln Val Arg Cys Gln Glu Thr Gly Lys Arg Tyr Trp
        290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
                340                 345                 350

Asp Ile Gly Leu Leu Leu Gly Met Ile Val Phe Ala Val Met Leu Ser
            355                 360                 365

Ile Leu Ser Leu Ile Gly Ile Phe Asn Arg Ser Phe Arg Thr Gly Ile
        370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Pro Gly Val
                405                 410                 415

Val Val Cys Ser Cys Asp Pro Ser Tyr Leu Gly Ser
            420                 425
```

-continued

<210> SEQ ID NO 9
<211> LENGTH: 1910
<212> TYPE: DNA
<213> ORGANISM: Homo sapiens
<220> FEATURE:
<221> NAME/KEY: CDS
<222> LOCATION: (1)...(1887)

<400> SEQUENCE: 9

```
atg aat cag gtc act att caa tgg gat gca gta ata gcc ctt tac ata      48
Met Asn Gln Val Thr Ile Gln Trp Asp Ala Val Ile Ala Leu Tyr Ile
 1               5                  10                  15 ctc ttc agc tgg tgt cat gga gga att aca aat ata aac tgc tct ggc      96
Leu Phe Ser Trp Cys His Gly Gly Ile Thr Asn Ile Asn Cys Ser Gly
             20                  25                  30 cac atc tgg gta gaa cca gcc aca att ttt aag atg ggt atg aat atc     144
His Ile Trp Val Glu Pro Ala Thr Ile Phe Lys Met Gly Met Asn Ile
         35                  40                  45 tct ata tat tgc caa gca gca att aag aac tgc caa cca agg aaa ctt     192
Ser Ile Tyr Cys Gln Ala Ala Ile Lys Asn Cys Gln Pro Arg Lys Leu
     50                  55                  60 cat ttt tat aaa aat ggc atc aaa gaa aga ttt caa atc aca agg att     240
His Phe Tyr Lys Asn Gly Ile Lys Glu Arg Phe Gln Ile Thr Arg Ile
 65                  70                  75                  80 aat aaa aca aca gct cgg ctt tgg tat aaa aac ttt ctg gaa cca cat     288
Asn Lys Thr Thr Ala Arg Leu Trp Tyr Lys Asn Phe Leu Glu Pro His
                 85                  90                  95 gct tct atg tac tgc act gct gaa tgt ccc aaa cat ttt caa gag aca     336
Ala Ser Met Tyr Cys Thr Ala Glu Cys Pro Lys His Phe Gln Glu Thr
            100                 105                 110 ctg ata tgt gga aaa gac att tct tct gga tat ccg cca gat att cct     384
Leu Ile Cys Gly Lys Asp Ile Ser Ser Gly Tyr Pro Pro Asp Ile Pro
        115                 120                 125 gat gaa gta acc tgt gtc att tat gaa tat tca ggc aac atg act tgc     432
Asp Glu Val Thr Cys Val Ile Tyr Glu Tyr Ser Gly Asn Met Thr Cys
    130                 135                 140 acc tgg aat gct ggg aag ctc acc tac ata gac aca aaa tac gtg gta     480
Thr Trp Asn Ala Gly Lys Leu Thr Tyr Ile Asp Thr Lys Tyr Val Val
145                 150                 155                 160 cat gtg aag agt tta gag aca gaa gaa gag caa cag tat ctc acc tca     528
His Val Lys Ser Leu Glu Thr Glu Glu Glu Gln Gln Tyr Leu Thr Ser
                165                 170                 175 agc tat att aac atc tcc act gat tca tta caa ggt ggc aag aag tac     576
Ser Tyr Ile Asn Ile Ser Thr Asp Ser Leu Gln Gly Gly Lys Lys Tyr
            180                 185                 190 ttg gtt tgg gtc caa gca gca aac gca cta ggc atg gaa gag tca aaa     624
Leu Val Trp Val Gln Ala Ala Asn Ala Leu Gly Met Glu Glu Ser Lys
        195                 200                 205 caa ctg caa att cac ctg gat gat ata gtg ata cct tct gca gcc gtc     672
Gln Leu Gln Ile His Leu Asp Asp Ile Val Ile Pro Ser Ala Ala Val
    210                 215                 220 att tcc agg gct gag act ata aat gct aca gtg ccc aag acc ata att     720
Ile Ser Arg Ala Glu Thr Ile Asn Ala Thr Val Pro Lys Thr Ile Ile
225                 230                 235                 240 tat tgg gat agt caa aca aca att gaa aag gtt tcc tgt gaa atg aga     768
Tyr Trp Asp Ser Gln Thr Thr Ile Glu Lys Val Ser Cys Glu Met Arg
                245                 250                 255 tac aag gct aca aca aac caa act tgg aat gtt aaa gaa ttt gac acc     816
Tyr Lys Ala Thr Thr Asn Gln Thr Trp Asn Val Lys Glu Phe Asp Thr
            260                 265                 270 aat ttt aca tat gtg caa cag tca gaa ttc tac ttg gag cca aac att     864
```

```
                    Asn Phe Thr Tyr Val Gln Gln Ser Glu Phe Tyr Leu Glu Pro Asn Ile
                                    275                 280                 285 aag tac gta ttt caa gtg aga tgt caa gaa aca ggc aaa agg tac tgg            912
Lys Tyr Val Phe Gln Val Arg Cys Gln Glu Thr Gly Lys Arg Tyr Trp
290                 295                 300 cag cct tgg agt tca ctg ttt ttt cat aaa aca cct gaa aca gtt ccc            960
Gln Pro Trp Ser Ser Leu Phe Phe His Lys Thr Pro Glu Thr Val Pro
305                 310                 315                 320 cag gtc aca tca aaa gca ttc caa cat gac aca tgg aat tct ggg cta           1008
Gln Val Thr Ser Lys Ala Phe Gln His Asp Thr Trp Asn Ser Gly Leu
            325                 330                 335 aca gtt gct tcc atc tct aca ggg cac ctt act tct gac aac aga gga           1056
Thr Val Ala Ser Ile Ser Thr Gly His Leu Thr Ser Asp Asn Arg Gly
            340                 345                 350 gac att gga ctt tta ttg gga atg atc gtc ttt gct gtt atg ttg tca           1104
Asp Ile Gly Leu Leu Leu Gly Met Ile Val Phe Ala Val Met Leu Ser
            355                 360                 365 att ctt tct ttg att ggg ata ttt aac aga tca ttc cga act ggg att           1152
Ile Leu Ser Leu Ile Gly Ile Phe Asn Arg Ser Phe Arg Thr Gly Ile
370                 375                 380 aaa aga agg atc tta ttg tta ata cca aag tgg ctt tat gaa gat att           1200
Lys Arg Arg Ile Leu Leu Leu Ile Pro Lys Trp Leu Tyr Glu Asp Ile
385                 390                 395                 400 cct aat atg aaa aac agc aat gtt gtg aaa atg cta cag gaa aat agt           1248
Pro Asn Met Lys Asn Ser Asn Val Val Lys Met Leu Gln Glu Asn Ser
            405                 410                 415 gaa ctt atg aat aat aat tcc agt gag cag gtc cta tat gtt gat ccc           1296
Glu Leu Met Asn Asn Asn Ser Ser Glu Gln Val Leu Tyr Val Asp Pro
            420                 425                 430 atg att aca gag ata aaa gaa atc ttc atc cca gaa cac aag cct aca           1344
Met Ile Thr Glu Ile Lys Glu Ile Phe Ile Pro Glu His Lys Pro Thr
            435                 440                 445 gac tac aag aag gag aat aca gga ccc ctg gag aca aga gac tac ccg           1392
Asp Tyr Lys Lys Glu Asn Thr Gly Pro Leu Glu Thr Arg Asp Tyr Pro
450                 455                 460 caa aac tcg cta ttc gac aat act aca gtt gta tat att cct gat ctc           1440
Gln Asn Ser Leu Phe Asp Asn Thr Thr Val Val Tyr Ile Pro Asp Leu
465                 470                 475                 480 aac act gga tat aaa ccc caa att tca aat ttt ctg cct gag gga agc           1488
Asn Thr Gly Tyr Lys Pro Gln Ile Ser Asn Phe Leu Pro Glu Gly Ser
            485                 490                 495 cat ctc agt aat aat aat gaa att act tcc tta aca ctt aaa cca cca           1536
His Leu Ser Asn Asn Asn Glu Ile Thr Ser Leu Thr Leu Lys Pro Pro
            500                 505                 510 gtt gat tcc tta gac tca gga aat aat ccc agg tta caa aag cat cct           1584
Val Asp Ser Leu Asp Ser Gly Asn Asn Pro Arg Leu Gln Lys His Pro
            515                 520                 525 aat ttt gct ttt tct gtt tca agt gtg aat tca cta agc aac aca ata           1632
Asn Phe Ala Phe Ser Val Ser Ser Val Asn Ser Leu Ser Asn Thr Ile
            530                 535                 540 ttt ctt gga gaa tta agc ctc ata tta aat caa gga gaa tgc agt tct           1680
Phe Leu Gly Glu Leu Ser Leu Ile Leu Asn Gln Gly Glu Cys Ser Ser
545                 550                 555                 560 cct gac ata caa aac tca gta gag gag gaa acc acc atg ctt ttg gaa           1728
Pro Asp Ile Gln Asn Ser Val Glu Glu Glu Thr Thr Met Leu Leu Glu
            565                 570                 575 aat gat tca ccc agt gaa act att cca gaa cag acc ctg ctt cct gat           1776
Asn Asp Ser Pro Ser Glu Thr Ile Pro Glu Gln Thr Leu Leu Pro Asp
            580                 585                 590
```

-continued

```
gaa ttt gtc tcc tgt ttg ggg atc gtg aat gag gag ttg cca tct att      1824
Glu Phe Val Ser Cys Leu Gly Ile Val Asn Glu Glu Leu Pro Ser Ile
    595                 600                 605 aat act tat ttt cca caa aat att ttg gaa agc cac ttc aat agg att      1872
Asn Thr Tyr Phe Pro Gln Asn Ile Leu Glu Ser His Phe Asn Arg Ile
610                 615                 620 tca ctc ttg gaa aag tagagctgtg tggtcaaaat caa                        1910
Ser Leu Leu Glu Lys
625
```

<210> SEQ ID NO 10
<211> LENGTH: 629
<212> TYPE: PRT
<213> ORGANISM: Homo sapiens

<400> SEQUENCE: 10

```
Met Asn Gln Val Thr Ile Gln Trp Asp Ala Val Ile Ala Leu Tyr Ile
1               5                  10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320
```

```
Gln Val Thr Ser Lys Ala Phe Gln His Asp Thr Trp Asn Ser Gly Leu
            325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
            355                 360                 365

Ile Leu Ser Leu Ile Gly Ile Phe Asn Arg Ser Phe Arg Thr Gly Ile
            370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
            405                 410                 415

Glu Leu Met Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
            435                 440                 445

Asp Tyr Lys Lys Glu Asn Thr Gly Pro Leu Glu Thr Arg Asp Tyr Pro
            450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
            485                 490                 495

His Leu Ser Asn Asn Asn Glu Ile Thr Ser Leu Thr Leu Lys Pro Pro
            500                 505                 510

Val Asp Ser Leu Asp Ser Gly Asn Asn Pro Arg Leu Gln Lys His Pro
            515                 520                 525

Asn Phe Ala Phe Ser Val Ser Val Asn Ser Leu Ser Asn Thr Ile
            530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
            565                 570                 575

Asn Asp Ser Pro Ser Glu Thr Ile Pro Glu Gln Thr Leu Leu Pro Asp
            580                 585                 590

Glu Phe Val Ser Cys Leu Gly Ile Val Asn Glu Glu Leu Pro Ser Ile
            595                 600                 605

Asn Thr Tyr Phe Pro Gln Asn Ile Leu Glu Ser His Phe Asn Arg Ile
            610                 615                 620

Ser Leu Leu Glu Lys
625

<210> SEQ ID NO 11
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 11
gcaacagtca gaattctact tggagcc                                      27

<210> SEQ ID NO 12
<211> LENGTH: 29
<212> TYPE: DNA
<213> ORGANISM: Artificial Sequence
<220> FEATURE:
```

<223> OTHER INFORMATION: Artificially synthesized primer sequence

<400> SEQUENCE: 12
cattaagtac gtatttcaag tgagatgtc                             29

<210> SEQ ID NO 13
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 13
ggtactggca gccttggagt tcactg                                26

<210> SEQ ID NO 14
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 14
cagtgaactc caaggctgcc agtacc                                26

<210> SEQ ID NO 15
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 15
gacatctcac ttgaaatacg tacttaatg                             29

<210> SEQ ID NO 16
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 16
ggctccaagt agaattctga ctgttgc                               27

<210> SEQ ID NO 17
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 17
ccgccagata ttcctgatga agtaacc                               27

<210> SEQ ID NO 18
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 18
atgaatcagg tcactattca atgg                                  24

```
<210> SEQ ID NO 19
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 19
gcagtcctcc tacttcagct tccc                                              24

<210> SEQ ID NO 20
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 20
ttgattttga ccacacagct ctac                                              24

<210> SEQ ID NO 21
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 3
<223> OTHER INFORMATION: Xaa = any amino acid

<400> SEQUENCE: 21

Trp Ser Xaa Trp Ser
  1               5

<210> SEQ ID NO 22
<211> LENGTH: 15
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: 7, 8, 9
<223> OTHER INFORMATION: n = a,t, g, or c

<400> SEQUENCE: 22
tggagynnnt ggagy                                                        15

<210> SEQ ID NO 23
<211> LENGTH: 360
<212> TYPE: DNA
<213> ORGANISM: Homo sapiens
<220> FEATURE:
<221> NAME/KEY: CDS
<222> LOCATION: (140)...(295)

<400> SEQUENCE: 23
ttttatataa agaacacttt gttttcctag agtctagaag acagcttgga acataatagg        60
tgttccatac atttctgcta aataaaatag ttgtttttaaa agcacaccac attttattat      120
tgttacccat ccattttag gtt aaa gaa ttt gac acc aat ttt aca tat gtg       172
                    Val Lys Glu Phe Asp Thr Asn Phe Thr Tyr Val
                      1               5                  10 caa cag tca gaa ttc tac ttg gag cca aac att aag tac gta ttt caa       220
Gln Gln Ser Glu Phe Tyr Leu Glu Pro Asn Ile Lys Tyr Val Phe Gln
         15                  20                  25
```

```
gtg aga tgt caa gaa aca ggc aaa agg tac tgg cag cct tgg agt tca      268
Val Arg Cys Gln Glu Thr Gly Lys Arg Tyr Trp Gln Pro Trp Ser Ser
         30                  35                  40 ctg ttt ttt cat aaa aca cct gaa aca ggtgagtgta cttatatatt            315
Leu Phe Phe His Lys Thr Pro Glu Thr
         45                  50 ttattctgtt gggcttttct ttatatatct tttctgctga gcaca                    360
```

<210> SEQ ID NO 24
<211> LENGTH: 52
<212> TYPE: PRT
<213> ORGANISM: Homo sapiens

<400> SEQUENCE: 24

```
Val Lys Glu Phe Asp Thr Asn Phe Thr Tyr Val Gln Gln Ser Glu Phe
 1               5                  10                  15

Tyr Leu Glu Pro Asn Ile Lys Tyr Val Phe Gln Val Arg Cys Gln Glu
                20                  25                  30

Thr Gly Lys Arg Tyr Trp Gln Pro Trp Ser Ser Leu Phe Phe His Lys
            35                  40                  45

Thr Pro Glu Thr
        50
```

<210> SEQ ID NO 25
<211> LENGTH: 25
<212> TYPE: PRT
<213> ORGANISM: Homo sapiens

<400> SEQUENCE: 25

```
Leu Glu Pro Asn Ile Lys Tyr Val Phe Gln Val Arg Cys Gln Glu Thr
 1               5                  10                  15

Gly Lys Arg Tyr Trp Gln Pro Trp Ser
                20                  25
```

<210> SEQ ID NO 26
<211> LENGTH: 26
<212> TYPE: PRT
<213> ORGANISM: Homo sapiens

<400> SEQUENCE: 26

```
Tyr Leu Glu Pro Asn Ile Lys Tyr Val Phe Gln Val Arg Cys Gln Glu
 1               5                  10                  15

Thr Gly Lys Arg Tyr Trp Gln Pro Trp Ser
                20                  25
```

<210> SEQ ID NO 27
<211> LENGTH: 39
<212> TYPE: PRT
<213> ORGANISM: Homo sapiens

<400> SEQUENCE: 27

```
Gln Gln Ser Glu Phe Tyr Leu Glu Pro Asn Ile Lys Tyr Val Phe Gln
 1               5                  10                  15

Val Arg Cys Gln Glu Thr Gly Lys Arg Tyr Trp Gln Pro Trp Ser Ser
                20                  25                  30

Leu Phe Phe His Lys Thr Pro
            35
```

<210> SEQ ID NO 28
<211> LENGTH: 46
<212> TYPE: PRT

<213> ORGANISM: Homo sapiens

<400> SEQUENCE: 28

Thr Asn Phe Thr Tyr Val Gln Gln Ser Glu Phe Tyr Leu Glu Pro Asn
1               5                   10                  15

Ile Lys Tyr Val Phe Gln Val Arg Cys Gln Glu Thr Gly Lys Arg Tyr
                20                  25                  30

Trp Gln Pro Trp Ser Ser Leu Phe Phe His Lys Thr Pro Glu
            35                  40                  45

<210> SEQ ID NO 29
<211> LENGTH: 34
<212> TYPE: PRT
<213> ORGANISM: Homo sapiens

<400> SEQUENCE: 29

Leu Glu Pro Asn Ile Lys Tyr Val Phe Gln Val Arg Cys Gln Glu Thr
1               5                   10                  15

Gly Lys Arg Tyr Trp Gln Pro Trp Ser Ser Leu Phe Phe His Lys Thr
                20                  25                  30

Pro Glu

<210> SEQ ID NO 30
<211> LENGTH: 26
<212> TYPE: PRT
<213> ORGANISM: Homo sapiens

<400> SEQUENCE: 30

Leu Lys Pro Phe Thr Glu Tyr Val Phe Arg Ile Arg Cys Met Lys Glu
1               5                   10                  15

Asp Gly Lys Gly Tyr Trp Ser Asp Trp Ser
                20                  25

<210> SEQ ID NO 31
<211> LENGTH: 26
<212> TYPE: PRT
<213> ORGANISM: Homo sapiens

<400> SEQUENCE: 31

His Ile Asp Pro Asn Val Asp Tyr Gln Phe Arg Val Cys Ala Arg Gly
1               5                   10                  15

Asp Gly Arg Gln Glu Trp Ser Pro Trp Ser
                20                  25

<210> SEQ ID NO 32
<211> LENGTH: 41
<212> TYPE: PRT
<213> ORGANISM: Homo sapiens

<400> SEQUENCE: 32

Gln Gln Thr Glu Phe Lys Ile Leu Ser Leu His Pro Gly Gln Lys Tyr
1               5                   10                  15

Leu Val Gln Val Arg Cys Lys Pro Asp His Gly Tyr Trp Ser Ala Trp
                20                  25                  30

Ser Pro Ala Thr Phe Ile Gln Ile Pro
            35                  40

<210> SEQ ID NO 33
<211> LENGTH: 45
<212> TYPE: PRT
<213> ORGANISM: Homo sapiens

```
<400> SEQUENCE: 33

Thr Lys Leu Thr Leu Leu Gln Arg Lys Leu Gln Pro Ala Ala Met Tyr
1               5                   10                  15

Glu Ile Lys Val Arg Ser Ile Pro Asp His Tyr Phe Lys Gly Phe Trp
                20                  25                  30

Ser Glu Trp Ser Pro Ser Tyr Tyr Phe Arg Thr Pro Glu
            35                  40                  45

<210> SEQ ID NO 34
<211> LENGTH: 34
<212> TYPE: PRT
<213> ORGANISM: Homo sapiens

<400> SEQUENCE: 34

Leu Asn Pro Tyr Thr Leu Tyr Thr Phe Arg Ile Arg Cys Ser Thr Glu
1               5                   10                  15

Thr Phe Trp Lys Trp Ser Lys Trp Ser Asn Lys Lys Gln His Leu Thr
                20                  25                  30

Thr Glu

<210> SEQ ID NO 35
<211> LENGTH: 6
<212> TYPE: PRT
<213> ORGANISM: Homo sapiens

<400> SEQUENCE: 35

Tyr Thr Phe Arg Ile Arg
1               5

<210> SEQ ID NO 36
<211> LENGTH: 6
<212> TYPE: PRT
<213> ORGANISM: Homo sapiens

<400> SEQUENCE: 36

Tyr Val Phe Arg Ile Arg
1               5

<210> SEQ ID NO 37
<211> LENGTH: 6
<212> TYPE: PRT
<213> ORGANISM: Homo sapiens

<400> SEQUENCE: 37

Gln Glu Phe Gln Leu Arg
1               5

<210> SEQ ID NO 38
<211> LENGTH: 6
<212> TYPE: PRT
<213> ORGANISM: Homo sapiens

<400> SEQUENCE: 38

Tyr Glu Phe Gln Ile Ser
1               5

<210> SEQ ID NO 39
<211> LENGTH: 6
<212> TYPE: PRT
<213> ORGANISM: Homo sapiens

<400> SEQUENCE: 39
```

Tyr Thr Leu Gln Ile Arg
1               5

<210> SEQ ID NO 40
<211> LENGTH: 6
<212> TYPE: PRT
<213> ORGANISM: Homo sapiens

<400> SEQUENCE: 40

Tyr Thr Phe Ala Val Arg
1               5

<210> SEQ ID NO 41
<211> LENGTH: 6
<212> TYPE: PRT
<213> ORGANISM: Homo sapiens

<400> SEQUENCE: 41

Tyr Arg Leu Gln Leu Arg
1               5

<210> SEQ ID NO 42
<211> LENGTH: 6
<212> TYPE: PRT
<213> ORGANISM: Homo sapiens

<400> SEQUENCE: 42

Tyr Ala Val Gln Val Arg
1               5

<210> SEQ ID NO 43
<211> LENGTH: 6
<212> TYPE: PRT
<213> ORGANISM: Homo sapiens

<400> SEQUENCE: 43

Tyr Thr Val Gln Ile Arg
1               5

<210> SEQ ID NO 44
<211> LENGTH: 6
<212> TYPE: PRT
<213> ORGANISM: Homo sapiens

<400> SEQUENCE: 44

Tyr Arg Ala Arg Val Arg
1               5

<210> SEQ ID NO 45
<211> LENGTH: 6
<212> TYPE: PRT
<213> ORGANISM: Homo sapiens

<400> SEQUENCE: 45

Tyr Asp Val Gln Val Arg
1               5

<210> SEQ ID NO 46
<211> LENGTH: 6
<212> TYPE: PRT
<213> ORGANISM: Homo sapiens

<400> SEQUENCE: 46

His Val Val Gln Leu Arg

```
                1               5
```

<210> SEQ ID NO 47
<211> LENGTH: 6
<212> TYPE: PRT
<213> ORGANISM: Homo sapiens

<400> SEQUENCE: 47

```
Tyr Glu Ile Lys Val Arg
 1               5
```

<210> SEQ ID NO 48
<211> LENGTH: 6
<212> TYPE: PRT
<213> ORGANISM: Homo sapiens

<400> SEQUENCE: 48

```
His Ala Val Arg Val Ser
 1               5
```

<210> SEQ ID NO 49
<211> LENGTH: 6
<212> TYPE: PRT
<213> ORGANISM: Homo sapiens

<400> SEQUENCE: 49

```
Asn Thr Val Arg Ile Arg
 1               5
```

<210> SEQ ID NO 50
<211> LENGTH: 6
<212> TYPE: PRT
<213> ORGANISM: Homo sapiens

<400> SEQUENCE: 50

```
Tyr Glu Phe Gln Val Arg
 1               5
```

<210> SEQ ID NO 51
<211> LENGTH: 6
<212> TYPE: PRT
<213> ORGANISM: Homo sapiens

<400> SEQUENCE: 51

```
Tyr Thr Phe Arg Val Arg
 1               5
```

<210> SEQ ID NO 52
<211> LENGTH: 6
<212> TYPE: PRT
<213> ORGANISM: Homo sapiens

<400> SEQUENCE: 52

```
His Ser Val Lys Ile Arg
 1               5
```

<210> SEQ ID NO 53
<211> LENGTH: 6
<212> TYPE: PRT
<213> ORGANISM: Homo sapiens

<400> SEQUENCE: 53

```
Tyr Ile Ile Gln Val Ala
 1               5
```

```
<210> SEQ ID NO 54
<211> LENGTH: 6
<212> TYPE: PRT
<213> ORGANISM: Homo sapiens

<400> SEQUENCE: 54

Tyr Leu Val Gln Val Arg
1               5

<210> SEQ ID NO 55
<211> LENGTH: 6
<212> TYPE: PRT
<213> ORGANISM: Homo sapiens

<400> SEQUENCE: 55

Tyr Phe Val Gln Val Arg
1               5

<210> SEQ ID NO 56
<211> LENGTH: 6
<212> TYPE: PRT
<213> ORGANISM: Homo sapiens

<400> SEQUENCE: 56

Tyr Gln Phe Arg Val Cys
1               5

<210> SEQ ID NO 57
<211> LENGTH: 5
<212> TYPE: PRT
<213> ORGANISM: Homo sapiens

<400> SEQUENCE: 57

Trp Ser Lys Trp Ser
1               5

<210> SEQ ID NO 58
<211> LENGTH: 5
<212> TYPE: PRT
<213> ORGANISM: Homo sapiens

<400> SEQUENCE: 58

Trp Ser Asp Trp Ser
1               5

<210> SEQ ID NO 59
<211> LENGTH: 5
<212> TYPE: PRT
<213> ORGANISM: Homo sapiens

<400> SEQUENCE: 59

Trp Ser Ala Trp Ser
1               5

<210> SEQ ID NO 60
<211> LENGTH: 5
<212> TYPE: PRT
<213> ORGANISM: Homo sapiens

<400> SEQUENCE: 60

Trp Ser Ser Trp Ser
1               5

<210> SEQ ID NO 61
```

```
<211> LENGTH: 5
<212> TYPE: PRT
<213> ORGANISM: Homo sapiens

<400> SEQUENCE: 61

Trp Ser Asn Trp Ser
1               5

<210> SEQ ID NO 62
<211> LENGTH: 5
<212> TYPE: PRT
<213> ORGANISM: Homo sapiens

<400> SEQUENCE: 62

Leu Ser Ala Trp Ser
1               5

<210> SEQ ID NO 63
<211> LENGTH: 5
<212> TYPE: PRT
<213> ORGANISM: Homo sapiens

<400> SEQUENCE: 63

Trp Ser Glu Trp Ser
1               5

<210> SEQ ID NO 64
<211> LENGTH: 5
<212> TYPE: PRT
<213> ORGANISM: Homo sapiens

<400> SEQUENCE: 64

Trp Ser Thr Trp Ser
1               5

<210> SEQ ID NO 65
<211> LENGTH: 5
<212> TYPE: PRT
<213> ORGANISM: Homo sapiens

<400> SEQUENCE: 65

Trp Ser Pro Trp Ser
1               5

<210> SEQ ID NO 66
<211> LENGTH: 5
<212> TYPE: PRT
<213> ORGANISM: Homo sapiens

<400> SEQUENCE: 66

Trp Ser Gly Trp Ser
1               5

<210> SEQ ID NO 67
<211> LENGTH: 5
<212> TYPE: PRT
<213> ORGANISM: Homo sapiens

<400> SEQUENCE: 67

Trp Gly Glu Trp Ser
1               5

<210> SEQ ID NO 68
<211> LENGTH: 5
<212> TYPE: PRT
```

<213> ORGANISM: Homo sapiens

<400> SEQUENCE: 68

Trp Ser Asp Trp Ala
1               5

<210> SEQ ID NO 69
<211> LENGTH: 5
<212> TYPE: PRT
<213> ORGANISM: Homo sapiens

<400> SEQUENCE: 69

Trp Ser Asn Trp Lys
1               5

<210> SEQ ID NO 70
<211> LENGTH: 5
<212> TYPE: PRT
<213> ORGANISM: Homo sapiens

<400> SEQUENCE: 70

Trp Ser Met Trp Ser
1               5

<210> SEQ ID NO 71
<211> LENGTH: 5
<212> TYPE: PRT
<213> ORGANISM: Homo sapiens

<400> SEQUENCE: 71

Trp Ser Gln Trp Ser
1               5

<210> SEQ ID NO 72
<211> LENGTH: 5
<212> TYPE: PRT
<213> ORGANISM: Homo sapiens

<400> SEQUENCE: 72

Trp Gln Pro Trp Ser
1               5

<210> SEQ ID NO 73
<211> LENGTH: 5
<212> TYPE: PRT
<213> ORGANISM: Homo sapiens

<400> SEQUENCE: 73

Trp Ser Glu Trp Gly
1               5

<210> SEQ ID NO 74
<211> LENGTH: 5
<212> TYPE: PRT
<213> ORGANISM: Homo sapiens

<400> SEQUENCE: 74

Thr Ser Gly Trp Ser
1               5

<210> SEQ ID NO 75
<211> LENGTH: 5
<212> TYPE: PRT
<213> ORGANISM: Homo sapiens

-continued

```
<400> SEQUENCE: 75

Trp Ser Arg Trp Ser
1               5

<210> SEQ ID NO 76
<211> LENGTH: 5
<212> TYPE: PRT
<213> ORGANISM: Homo sapiens

<400> SEQUENCE: 76

Trp Ser Glu Gly Ser
1               5

<210> SEQ ID NO 77
<211> LENGTH: 6
<212> TYPE: PRT
<213> ORGANISM: Homo sapiens

<400> SEQUENCE: 77

Tyr Val Phe Gln Val Arg
1               5
```

HEMOPOIETIN RECEPTOR PROTEIN, NR12

This application is a continuation-in-part of International Patent Application No. PCT/JP00/06654, filed Sep. 27, 2000, which claims priority to Japanese Patent Application Nos. 11/273358, filed Sep. 27, 1999, and 2000-240397, filed Aug. 3, 2000.

TECHNICAL FIELD

The present invention relates to novel hemopoietin receptor proteins, and genes encoding them, as well as methods for producing and using the same.

BACKGROUND

A large number of cytokines are known as humoral factors that regulate proliferation/differentiation of various cells, or that regulate the maintenance, activation, and death of differentiated mature cells. There are specific receptors for these cytokines, which are categorized into several families based on their structural similarities (Hilton D. J., in "Guidebook to Cytokines and Their Receptors" edited by Nicola N. A. (A Sambrook & Tooze Publication at Oxford University Press), 1994, p 8–16).

On the other hand, as compared to the similarities of their receptors, the homology of the primary-structure among cytokines is quite low. No significant amino acid homology has be observed, even among cytokine members that belong to the same receptor family. This explains the functional specificity of respective cytokines, as well as similarities among cellular reactions induced by each cytokine.

Representative examples of the above-mentioned receptor families are the tyrosine kinase receptor family, hemopoietin receptor family, tumor necrosis factor (TNF) receptor family, and transforming growth factor (TGF) receptor family. Different signal transduction pathways have been reported to be involved with each of these families. Among these receptor families, many receptors of the hemopoietin receptor family in particular are expressed in blood cells and immunocytes, and their ligands, cytokines, are often termed as hemopoietic factors or interleukins. Some of these hemopoietic factors or interleukins exist within blood and are thought to be involved in systemic humoral regulation of hemopoietic or immune functions.

This contrasts with the belief that cytokines belonging to other families are often involved in only topical regulation. Some of these hemopoietins can be taken as hormone-like factors, and representative peptide hormones, such as the growth hormone, prolactin, or leptin receptors, also belong to the hemopoietin receptor family. Because of these hormone-like systemic regulatory features, it is anticipated that administration of these hemopoietins can be applied to the treatment of various diseases. Among the large number of cytokines known, those that are presently being clinically applied include erythropoietin, G-CSF, GM-CSF, and IL-2. Combined with IL-11, LIF, and IL-12 that are currently under consideration for clinical trials, and the above-mentioned peptide hormones, such as the growth hormone and prolactin, it can be envisaged that by searching novel cytokines that bind to hemopoietin receptors among the above-mentioned various receptor superfamilies, it is possible to find a cytokine that can be clinically applied with a higher efficiency.

As mentioned above, cytokine receptors have structural similarities among the family members. Using these similarities, many investigations are aimed at finding novel receptors. In particular, many receptors of the tyrosine kinase receptor family have already been cloned, using its highly conserved sequence at the catalytic site (Matthews et al., Cell 65(7):143–52, 1991). In comparison, hemopoietin receptors do not have a tyrosine kinase-like enzyme activity domain in their cytoplasmic regions, and their signal transductions are known to be mediated through associations with other tyrosine kinase proteins existing freely in the cytoplasm. Though the sites on receptors binding with these cytoplasmic tyrosine kinases, called JAK kinases group, are conserved among family members, the homology is not very high (Murakami et al., Proc. Natl. Acad. Sci. USA 88:11349–11353, 1991). Actually, the sequence that best characterizes these hemopoietin receptors exists in the extracellular region. In particular, a five amino acid motif, Trp-Ser-Xaa-Trp-Ser (wherein "Xaa" is an arbitrary amino acid; SEQ ID NO:21), is conserved in almost all of the hemopoietin receptors. Therefore, novel receptors may be obtained by searching for novel family members using this motif sequence. In fact, these approaches have already led to the identification of the IL-11 receptor (Robb et al., J. Biol. Chem. 271(23):13754–13761, 1996), the leptin receptor (Gainsford et al., Proc. Natl. Acad. Sci. USA 93(25):14564–8, 1996), and the IL-13 receptor (Hilton et al., Proc. Natl. Acad. Sci. USA 93(1):497–501, 1996).

SUMMARY

The present invention provides novel hemopoietin receptor proteins, and DNA encoding these proteins. The present invention also provides a vector into which the DNA has been inserted, a transformant harboring the DNA, and a method for producing recombinant proteins using the transformant. The present invention also provides methods of screening for compounds that bind to the protein.

Initially, the inventors attempted to find a novel receptor using oligonucleotides encoding the Trp-Ser-Xaa-Trp-Ser motif (WS motif; SEQ ID NO:21) as the probe by the plaque hybridization method, RT-PCR method, and so on. However, it was extremely difficult to strictly select only those to which all 15 nucleotides that encode the motif would completely hybridize under the usual hybridization conditions, because the oligonucleotide "tggag(t/c)nnntggag(t/c)" (wherein "n" is an arbitrary nucleotide; SEQ ID NO:22) encoding the motif was short, having just 15 base pairs. Further, because the g/c content of the oligonucleotide was high, higher than usual annealing temperature conditions were required to strictly select those sequences in which all the 15 nucleotides hybridized completely to the oligonucleotide. Therefore, performing screening under normal hybridization experiment conditions was extremely difficult.

To solve these problems, the inventors searched for additional motifs, other than the site of the above-mentioned WS motif that is conserved in the hemopoietin receptor family. The inventors found that a residue, either tyrosine or histidine, located 13 to 27 amino acids upstream of the WS motif in the extracellular region was highly conserved in the receptor family. Furthermore, additional search for consensus sequences that are frequently found in the 6 amino acids from the above Tyr/His residue toward the C-terminus led to the identification of the following consensus sequence: (Tyr/His)-Xaa-(Hydrophobic/Ala)-(Gln/Arg)-Hydrophobic-Arg (hereinafter, abbreviated as the YR motif). However, this YR motif is not exactly a perfect consensus sequence, and the combination of the nucleotide sequences that encode the motif is very complicated. Therefore, it is practically impossible to synthesize and provide oligonucleotides that encode all of the amino acid sequences as probes for hybridization, which is a practical method for screening, or as primers aimed for RT-PCR.

Accordingly, the inventors looked for other approaches to practically search for novel members of the hemopietin receptor family using the above two motifs as probes, and determined that it would be appropriate to perform a database search on the computer using partial amino acid sequences of known hemopoietin receptors, including both motifs as the query. The inventors repeated TblastN searches on the gss and htgs database in GenBank, using partial amino acid sequences from multiple known hemopoietin receptors as the query. As a result, many positive clones, including known hemopoietin receptors, were obtained in all cases. Next, the nucleotide sequence around those sequences which seemed to be positive at a high rate was converted to the amino acid sequence. Genes considered to encode members of the receptor family were selected by BlastX search, in which the amino acid sequences (converted from the nucleotide sequences of the clones) were compared to those of known hemopoietin receptors. According to the two-step Blast search above, human genome sequences encoding two clones of known hemopoietin receptor genes and one clone of novel hemopoietin receptor gene were identified. Subsequently, specific oligonucleotide primers were designed based on the exon sequences predicted from the obtained nucleotide sequence. Clones corresponding to the N-terminal region and C-terminal region of NR12 were obtained by conducting 5'-RACE and 3'-RACE methods using the primers, and cDNA libraries of human fetal liver, adult thymus, and adult testis as the templates. The complete nucleotide sequence of the full-length cDNA was revealed by determining the nucleotide sequences of both clones, and connecting the sequence at the duplicated center region.

From structural analyses, at least three kinds of transcription products derived from splice variants were recognized. A cDNA clone of these splice variants comprising 337 amino acids and potentially encoding a secretory form soluble receptor protein was named NR12.1; the other two clones, comprising 428 amino acids and 629 amino acids respectively and each encoding transmembrane form receptor proteins, were named NR12.2 and NR12.3. Because repeated structure of cysteine residues, YR motif, WS motif, and so on, that are conserved in the extracellular region of other family members were well conserved in the primary structure of all the isolated cDNA clones of NR12, it was considered that these clones encode typical hemopoietin receptors.

Subsequently, RT-PCR was performed using primer sets specific to NR12.1, NR12.2, and NR12.3, respectively, against mRNA derived from various human tissue. Then, tissues expressing these genes were searched, and the distribution and the expression pattern of the genes in each human tissue were analyzed. Finally, in order to discard the possibility of non-specific amplification and to quantify the amount of the RT-PCR products, the products of RT-PCR were subjected to Southern blotting using cDNA fragments specific to the respective clones. The result indicated that these clones are mainly expressed in hematopoietic cell line tissue and immune cell line tissue.

Furthermore, the present inventors succeeded in obtaining two clones (NR12.4 and NR12.5) encoding complete proteins that were 3 amino acids different from NR12.2 and NR12.3, respectively, by conducting PCR cloning against the cDNA library of human thymus (wherein five clones generically named "NR12" were isolated).

Based on the above features of NR12, NR12 is presumed to be a novel hemopoietin receptor molecule related to the regulation of the immune system or hematopoiesis. The gene encoding NR12 will be extremely useful in the screening for novel hematopoietic factors that can functionally bind to the receptor.

Moreover, the present inventors succeeded in isolating genomic fragments of mouse receptor homologues by conducting xenogenic cross hybridization cloning using cDNA of human NR12 as the probe. It is expected that further elucidation of the in vivo function of the receptor protein is possible by constructing mutant mouse lacking NR12 gene using the mouse gene fragments.

Consequently, the present invention relates to novel hemopoietin receptors and genes encoding the receptors, as well as use of the same. More specifically, the present invention provides the following:

(1) a DNA selected from the group consisting of:
(a) a DNA encoding a protein comprising the amino acid sequence of any one of SEQ ID NOs:2, 4, 6, 8, and 10;
(b) a DNA comprising the coding region of the nucleotide sequence of any one of SEQ ID NOs:1, 3, 5, 7, and 9;
(c) a DNA encoding a protein comprising the amino acid sequence of any one of SEQ ID NOs:2, 4, 6, 8, and 10, in which one or more amino acids are modified by substitution, deletion, insertion, and/or addition, wherein said protein is functionally equivalent to the protein consisting of the amino acid sequence of any of SEQ ID NOs:2, 4, 6, 8, and 10; and,
(d) a DNA hybridizing under stringent conditions with a DNA consisting of the nucleotide sequence of any one of SEQ ID NOs:1, 3, 5, 7, and 9, and encoding a protein that is functionally equivalent to the protein consisting of the amino acid sequence of any one of SEQ ID NOs:2, 4, 6, 8, and 10;

(2) a DNA encoding a partial peptide of a protein consisting of the amino acid sequence of any one of SEQ ID NOs:2, 4, 6, 8, and 10;

(3) a protein or peptide that is encoded by the DNA described in (1) or (2);

(4) a vector into which the DNA described in (1) or (2) is inserted;

(5) a transformant harboring the DNA described in (1) or (2), or the vector described in (4);

(6) a method for producing the protein or peptide of (3), comprising the steps of: culturing said transformant of (5), and recovering the expressed protein from said transformant or the culture supernatant;

(7) an antibody binding to the protein of (3);

(8) a polynucleotide complementary to either a DNA that comprises the nucleotide sequence of any one of SEQ ID NOs:1, 3, 5, 7, and 9 or its complementary strand, wherein the polynucleotide comprises at least 15 nucleotides; and, (9) a method of screening for a compound that binds to the protein of (3), comprising the steps of:
(a) contacting a test sample with said protein or partial peptide thereof;
(b) detecting the binding activity of the test sample with the protein or partial peptide thereof; and,
(c) selecting the compound that binds to the protein or partial peptide thereof.

The present invention provides a novel hemopoietin receptor "NR12". According to the results of the database searches on GenBank as well as 5'-RACE and 3'-RACE analysis, the present inventors finally succeeded in identifying and isolating a novel hemopoietin receptor gene NR12. It was found that at least three splice variants are transcribed from NR12. One of these variants, the cDNA clone NR12.1, encodes a soluble receptor-like protein. The other two predicted to encode transmembrane receptor proteins, cDNA clone NR12.2 and NR12.3, encode a protein presumed to have an intracellular region as short as 51 amino acids and as long as 252 amino acids, respectively.

Furthermore, the present inventors conducted PCR cloning against a cDNA library of human thymus to isolate the continuous full-length coding sequences (CDS). A clone having almost the same full-length ORF as NR12.2 was named NR12.4, and that having almost the same full-length ORF as NR12.3 was named NR12.5.

The nucleotide sequence of NR12.1 cDNA is shown in SEQ ID NO:1, and the corresponding amino acid sequence of the protein encoded by the cDNA is shown in SEQ ID NO:2. The nucleotide sequence of NR12.2 cDNA is shown in SEQ ID NO:3, and the corresponding amino acid sequence of the protein encoded by the cDNA is shown in SEQ ID NO:4. The nucleotide sequence of NR12.3 cDNA is shown in SEQ ID NO:5, and the corresponding amino acid sequence of the protein encoded by the cDNA is shown in SEQ ID NO:6. The nucleotide sequence of NR12.4 cDNA is shown in SEQ ID NO:7, and the corresponding amino acid sequence of the protein encoded by the cDNA is shown in SEQ ID NO:8. The nucleotide sequence of NR12.5 cDNA is shown in SEQ ID NO:9, and the corresponding amino acid sequence of the protein encoded by the cDNA is shown in SEQ ID NO:10.

Because the extracellular regions of NR12.1, NR12.2, NR12.3, NR12.4, and NR12.5 are almost identical, these regions are thought to have the same tertiary structure and thereby recognize the same specific ligand.

Analyses of the gene expression in various human organs using RT-PCR revealed: strong expression of NR12 in hematopoietic cell line tissues and immune cell line tissues such as adult spleen, thymus, lymph node, bone marrow, and peripheral leukocyte; and expression in testis, liver, lung, kidney, pancreas, and gastrointestinal tract, such as small intestine and colon. Additionally, expression of NR12 was also observed in all the analyzed mRNA derived from human fetal organs. From the revealed distribution pattern of NR12 gene expression, it was presumed that NR12 encodes a novel hematopoietic factor receptor, primarily because localization of strong expression in tissues thought to include immune cell lines and hematopoietic cells was detected. Furthermore, the fact that NR12 expression was observed in tissues other than those described above suggests that NR12 can regulate not only physiological functions of the immune system and hematopoietic system in vivo but also various other physiological functions in vivo.

The above NR12 proteins are potentially useful for medical application. Since NR12.1 is expressed in thymus, peripheral leukocytes, and spleen, it is predicted to be a receptor for an unknown hemopoietic factor. Therefore, NR12 proteins are useful tools in the identification of the unknown hemopoietic factor. They may also be used to screen a peptide library or synthetic chemical compounds to isolate or identify agonists and antagonists that can functionally bind to the NR12 molecule. Moreover, clinical application is expected of novel molecules binding to the NR12 molecule and specific antibodies that can limit the function of the NR12 molecule to regulate the immune response or hematopoiesis in vivo, by searching such molecules and antibodies.

NR12 is expected to be expressed in a restricted population of cells in the hemopoietic tissues, and thus, anti-NR12 antibodies are useful for the isolation of such cell populations. The isolated cell populations may be used in cell transplantation. Furthermore, it is expected that the anti-NR12 antibody may be used for the diagnosis or treatment of diseases, such as leukemia.

On the other hand, the soluble proteins comprising the extracellular domain of NR12 protein and the splice variant of NR12, NR12.1, may be used as a decoy-type receptor to inhibit the NR12 ligand. They may be useful for the treatment of diseases in which NR12 is implicated, such as leukemia.

The present invention includes proteins that are functionally equivalent to the NR12 protein. For example, homologues of human NR12 protein are included. Herein, the term "functionally equivalent" refers to proteins having an equivalent biological activity as compared to that of an NR12 protein. Such biological activity may include the protein activity as a membrane bound or soluble form hematopoietic factor receptor.

Methods of introducing mutations for preparing proteins that are functionally equivalent to another protein are well known to a person skilled in the art. For example, one skilled in the art may use site-directed mutagenesis (Hashimoto-Gotoh et al., Gene 152:271–275, 1995; Zoller et al., Methods Enzymol. 100:468–500, 1983; Kramer et al., Nucleic Acids Res. 12:9441–9456, 1984; Kramer et al., Methods. Enzymol. 154:350–367, 1987; Kunkel, Proc. Natl. Acad. Sci. USA 82:488–492, 1985; Kunkel, Methods Enzymol. 85:2763–2766, 1988) and such in order to introduce an appropriate mutation into the amino acid sequence of the human NR12 protein and prepare a protein that is functionally equivalent to the protein. Mutation of amino acids may occur in nature as well. The proteins of the present invention includes proteins having the amino acid sequence of human NR12 protein in which one or more amino acids are mutated, so long as the resulting proteins are functionally equivalent to human NR12 protein.

As a protein functionally equivalent to the NR12 protein of the invention, the following can be specifically mentioned: one in which one or two, preferably, two to 30, more preferably, two to 10 amino acids are deleted in any one of the amino acid sequences of SEQ ID NOs:2, 4, 6, 8, or 10; one in which one or two, preferably, two to 30, more preferably, two to 10 amino acids have been added into any one of the amino acid sequences of SEQ ID NOs:2, 4, 6, 8, or 10; one in which one or two, preferably, two to 30, more preferably, two to 10 amino acids have been substituted with other amino acids in any one of the amino acid sequences of SEQ ID NOs:2, 4, 6, 8, or 10.

As for the amino acid residue to be mutated, it is preferable that it be mutated into a different amino acid that allows the properties of the amino acid side-chain to be conserved. Examples of properties of amino acid side chains are the following: hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W) (The parenthetic letters indicate the one-letter codes of amino acids).

It is known that a protein may have an amino acid sequence modified by deletion, addition, and/or substitution of other amino acids for one or more amino acid residues, yet still retain its biological activity (Mark et al., Proc. Natl. Acad. Sci. USA 81:5662–5666, 1984; Zoller et al., Nucleic Acids Res. 10:6487–6500, 1982; Wang et al., Science 224: 1431–1433; Dalbadie-McFarland et al., Proc. Natl. Acad. Sci. USA 79:6409–6413, 1982).

A fusion protein comprising human NR12 protein is an example of a protein in which one or more amino acids residues have been added to the amino acid sequence of a human NR12 protein (e.g., SEQ ID NO:2, 4 6, 8 or 10). A fusion protein is made by fusing the human NR12 protein with another peptide(s) or protein(s) and is included in the present invention. A fusion protein can be prepared by ligating a DNA encoding the human NR12 protein of the present invention with a DNA encoding another peptide(s) or protein(s) in frame, introducing the ligated DNA into an expression vector, and expressing the fusion gene in a host. Methods known by one skilled in the art can be used for preparing such a fusion gene. There is no restriction as to the other peptide(s) or protein(s) that is (are) fused to the protein of the present invention.

Other peptide(s) to be fused with a protein of the present invention include known peptides, for example, FLAG (Hopp et al., Biotechnology 6:1204–1210, 1988), 6× His consisting of six His (histidine) residues, 10× His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and so on. Other examples of proteins to be fused with the protein of the present invention are the GST (glutathione-S-transferase), Influenza agglutinin (HA), immunoglobulin constant region, β-galactosidase, MBP (maltose-binding protein), and such.

Fusion proteins can be prepared by fusing commercially available DNA encoding these peptides or proteins with DNA encoding a protein of the present invention and expressing the fused DNA prepared.

The hybridization technique (Sambrook et al., Molecular Cloning 2nd ed., 9.47–9.58, Cold Spring Harbor Lab. Press, 1989) is well known to those skilled in the art as an alternative method for preparing a protein functionally equivalent to a certain protein. More specifically, one skilled in the art can utilize the general procedure to obtain a protein functionally equivalent to a human NR12 protein by isolating DNA having a high homology with the whole or part of a DNA sequence encoding the human NR12 protein (e.g., SEQ ID NO:1, 3, 5, 7 or 9). Thus, the proteins of the present invention include such proteins, that are encoded by DNAs that hybridizes with a DNA encoding a human NR12 protein or part thereof and that are functionally equivalent to a human NR12 protein. Examples include homologues of human NR12 in other mammals (for example, those of monkey, rat, mouse, rabbit, and bovine gene). In order to isolate a cDNA with high homology to a DNA encoding a human NR12 protein from animals, it is preferable to use a hematopoietic cell line tissue such as spleen, thymus, lymph node, bone marrow, and peripheral leukocyte; however, the invention is not limited thereto.

Stringent hybridization conditions for isolating DNA encoding proteins functionally equivalent to a human NR12 protein can be suitably selected by one skilled in the art, and for example, low-stringent conditions can be given. Low-stringent conditions are, for example, 42° C., 2×SSC, and 0.1% SDS, and preferably, 50° C., 2×SSC, and 0.1% SDS. High stringent conditions are more preferable and include, for example, 65° C., 2×SSC, and 0.1% SDS. Under these conditions, at lower temperatures, the DNA obtained will have a lower homology. Conversely, it is expected that the homology of the obtained DNA will be higher at higher temperatures. However, several factors other than temperature, such as salt concentration, can also influence the stringency of hybridization and one skilled in the art can routinely select the factors to accomplish a similar stringency.

In place of hybridization, the gene amplification method, for example, the polymerase chain reaction (PCR) method can be utilized to isolate the object DNA, using primers synthesized based on the sequence information of a DNA (e.g., SEQ ID NO:1, 3, 5, 7 or 9) encoding human NR12 protein.

Proteins that are functionally equivalent to human NR12 protein, encoded by DNA isolated through the above hybridization technique or by the gene amplification techniques, usually have a high homology to the amino acid sequence of the human NR12 protein. The proteins of the present invention also include proteins that are functionally equivalent to the human NR12 protein, which also have a high homology with the protein comprising any one of the amino acid sequences of SEQ ID NO:2, 4, 6, 8, and 10. High homology is normally defined as a homology of 70% or higher, preferably 80% or higher, more preferably 90% or higher, and most preferably 95% or higher. The homology of a protein can be determined by the algorithm in "Wilbur, W. J. and Lipman, D. J. Proc. Natl. Acad. Sci. USA (1983) 80, 726–730".

The amino acid sequence, molecular weight, isoelectric point, the presence or absence of sugar chains, and the form of a protein of the present invention may differ according to the producing cells, host, or purification method described below. However, so long as the obtained protein has an equivalent function to human NR12 protein (SEQ ID NO:2, 4, 6, 8 or 10), it is included in the present invention. For example, if a protein of the present invention is expressed in prokaryotic cells, such as *E. coli*, a methionine residue is added at the N-terminus of the amino acid sequence of the expressed protein. If a protein of the present invention is expressed in eukaryotic cells, such as mammalian cells, the N-terminal signal sequence is removed. Such proteins are also included as proteins of the present invention.

For example, as a result of analysis of the protein of the invention based on the method in "Von Heijne, G., Nucleic Acids Research, (1986), 14, 4683–4690", it was presumed that the signal sequence extends from the $1^{st}$ Met to the $23^{rd}$ Gly in the amino acid sequences of SEQ ID NO:2, 4, 6, 8 and 10. Therefore, the present invention encompasses a protein comprising the sequence from the $24^{th}$ Gly to $337^{th}$ Cys in the amino acid sequence of SEQ ID NO:2. Similarly, the present invention encompasses a protein comprising the sequence from the $24^{th}$ Gly to $428^{th}$ Ser in the amino acid sequence of SEQ ID NO:4. Similarly, the present invention encompasses a protein comprising the sequence from the $24^{th}$ Gly to $629^{th}$ Lys in the amino acid sequence of SEQ ID NO:6. Similarly, the present invention encompasses a protein comprising the sequence from the $24^{th}$ Gly to $428^{th}$ Ser in the amino acid sequence of SEQ ID NO:8. Similarly, the present invention encompasses a protein comprising the sequence from the $24^{th}$ Gly to $629^{th}$ Lys in the amino acid sequence of SEQ ID NO:10.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:2, 4, 6, 8 or 10. The invention also includes a polypeptide, or fragment thereof, that differs from the corresponding sequence shown as SEQ ID NO:2, 4, 6, 8 or 10. The differences are, preferably, differences or changes at a non-essential residue or a conservative substitution. In one embodiment, the polypeptide includes an amino acid sequence at least about 60% identical to a sequence shown as SEQ ID NO:2, 4, 6, 8 or 10, or a fragment thereof. Preferably, the polypeptide is at least 65%, 70%, 75%, 80%, 85%, 90%, 95%, 98%, 99% or more identical to SEQ ID NO:2, 4, 6, 8 or 10 and has at least one receptor activity described herein, e.g., a hemopoietin receptor activity. Preferred polypeptide fragments of the invention are at least 10%, preferably at least 20%, 30%, 40%, 50%, 60%, 70%, or more, of the length of the sequence shown as SEQ ID NO:2, 4, 6, 8 or 10 and have at least one receptor activity described herein, e.g., a hemopoietin receptor activity. Or alternatively, the fragment can be merely an immunogenic fragment.

A protein of the present invention can be prepared by methods known to one skilled in the art, as a recombinant protein, and also as a natural protein. A recombinant DNA can be prepared by inserting a DNA encoding the protein of the present invention (for example, the DNA comprising the nucleotide sequence of SEQ ID NO:1, 3, 5, 7 or 9) into a suitable expression vector, introducing the vector into a suitable host cell, and collecting the extract from the resulting transformant. After obtaining the extract, recombinant protein can be purified and prepared by subjecting to chromatography, such as ion exchange chromatography, reverse phase chromatography, gel filtration, and such, or affinity chromatography, wherein antibodies against the protein of the present invention are immobilized, or using one or more of these columns in combination.

Further, when a protein of the present invention is expressed within host cells (for example, animal cells and *E. coli*), as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin, factor-Xa, and such, as required.

A natural protein may be isolated by methods known to one skilled in the art. For example, extracts of tissue or cells expressing a protein of the invention may be reacted with an affinity column described below, to which antibodies binding to the human NR12 protein are attached, to isolate the natural protein. Polyclonal or monoclonal antibodies may be used.

The present invention also includes partial peptides of the proteins of the present invention. A partial peptide consists of an amino acid sequence specific to a protein of the present invention and is composed of at least 7 amino acids, preferably more than 8 amino acids, and more preferably more than 9 amino acids. The partial peptides may be useful, for example, for preparing antibodies against a protein of the present invention; for screening compounds binding to a protein of the present invention, or for screening accelerators or inhibitors of a protein of the present invention. Alternatively, they may be used as antagonists for the ligand of a protein of the present invention. A partial peptide of a protein of the present invention is, for example, a partial peptide having the active center of the protein consisting of the amino acid sequences of SEQ ID NO:2, 4, 6, 8, or 10. Additionally, the partial peptides may comprise one or more regions of the hydrophilic region and hydrophobic region determined by hydrophobicity plot analysis. These partial peptides may contain the whole hydrophilic region or a part of a hydrophilic region, or may contain the whole or a part of the hydrophobic region. Moreover, for example, soluble proteins and proteins comprising extracellular regions of a protein of the invention are also encompassed in the invention.

The partial peptides of the invention may be produced by genetic engineering techniques, well-known peptide synthesizing methods, or by excising a protein of the invention with a suitable peptidase. For example, the solid phase synthesizing method or liquid phase synthesizing method may be used as peptide synthesizing method.

Another object of the present invention is to provide a DNA encoding a protein of the present invention. The DNA may be useful for producing the above proteins of the present invention in vivo or in vitro. Furthermore, for example, it is also possible to use the DNA for application to gene therapy and such of diseases arising from abnormalities of the gene encoding the protein of the present invention. The DNA may be provided in any form, so long as it encodes a protein of the present invention. Thus, the DNA may be a cDNA synthesized from mRNA, genomic DNA, or chemically synthesized DNA. Furthermore, a DNA comprising any nucleotide sequence based on the degeneracy of genetic code may be included so long as it encodes a protein of the present invention.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1, 3, 5, 7 or 9. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1, 3, 5, 7 or 9. In the case of an isolated nucleic acid molecule which is longer than or equivalent in length to the reference sequence, e.g., SEQ ID NO:1, 3, 5, 7 or 9, the comparison is made with the full length of the reference sequence. Where the isolated nucleic acid molecule is shorter that the reference sequence, e.g., shorter than SEQ ID NO:1, 3, 5, 7 or 9, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (Proc. Natl. Acad. Sci. USA 87:2264–2268, 1990), modified as in Karlin and Altschul, Proc. Natl. Acad. Sci. USA 90:5873–5877, 1993). Such an algorithm is incorporated into the NBLAST and XBLAST programs of Altschul et al. (J. Mol. Biol. 215: 403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389–3402, 1997). When utilizing BLAST and Gapped-BLAST programs the default parameters of the respective programs (e.g., XBLAST and NBLAST) are used to obtain nucleotide sequences homologous to a nucleic acid molecule of the invention.

The DNA of the present invention can be prepared by any method known to a person skilled in the art. For example, the DNA of the present invention may be prepared by constructing a cDNA library from cells expressing the protein of the present invention, and conducting hybridization using as a probe a partial sequence of a DNA of the present invention (for example, SEQ ID NO:1, 3, 5, 7 or 9). A cDNA library may be constructed, for example, according to the method described in the literature (Sambrook et al., Molecular Cloning, Cold Spring Harbor Laboratory Press, 1989), or a commercial cDNA library may be used. Alternatively, the DNA may be prepared by obtaining RNA from a cell expressing a protein of the present invention, synthesizing oligo DNA based on the sequence of a DNA of the present invention (for example, SEQ ID NO:1, 3, 5, 7 or 9), conducting PCR using the synthesized DNA as primers, and amplifying the cDNA encoding a protein of the present invention.

By determining the nucleotide sequence of the obtained cDNA, the translation region encoded by the cDNA can be determined, and the amino acid sequence of the protein of the present invention can be obtained. Furthermore, genomic DNA can be isolated by screening genomic DNA libraries using the obtained cDNA as a probe.

Specifically, this can be done as follows: first, mRNA is isolated from cells, tissues, or organs expressing a protein of the invention (for example, hematopoietic-competent cell line tissue such as spleen, thymus, lymph node, bone marrow, peripheral leukocyte and immunocompetent cell line tissue, and such). To isolate the mRNA, at first, whole RNA is prepared using well-known methods, for example, the guanidine ultracentrifugation method (Chirgwin et al., Biochemistry 18:5294–5299, 1979), the AGPC method (Chomczynski et al., Anal. Biochem. 162:156–159,1987), and such. Next, mRNA from whole mRNA can be purified using the mRNA Purification Kit (Pharmacia), and such. Alternatively, mRNA may be directly prepared by QuickPrep mRNA Purification Kit (Pharmacia).

cDNA can then be synthesized using reverse transcriptase from the obtained mRNA. cDNA can be synthesized by using the AMV Reverse Transcriptase First-strand cDNA Synthesis Kit (Seikagaku Kogyo), etc. Additionally, cDNA synthesis and amplification may be also performed using the primer and such described herein, following the 5'-RACE method (Frohman et al. Proc. Natl. Acad. Sci. USA 85:8998–9002, 1988; Belyavsky et al., Nucleic Acids Res. 17:2919–2932, 1989) utilizing the polymerase chain reaction (PCR) and the 5'-Ampli FINDER RACE Kit (Clontech).

The objective DNA fragment is prepared from the obtained PCR product and ligated with a vector DNA. Thus, a recombinant vector is created and introduced into $E.\ coli$, and such, and colonies are selected to prepare the desired recombinant vector. The nucleotide sequence of the objective DNA can be verified by conventional methods, for example, dideoxynucleotide chain termination.

With regards to the DNA of the invention, a sequence with higher expression efficiency can be designed by considering the codon usage frequency in the host used for the expression (Grantham et al., Nucleic Acids Res. 9:43–74, 1981). The DNA of the present invention may also be modified using commercially available kits and conventional methods. Illustrative modifications include, for instance, digestion by restriction enzymes, insertion of synthetic oligonucleotides and suitable DNA fragments, addition of linkers, insertion of a initiation codon (ATG) and/or stop codon (TAA, TGA, or TAG), and such.

Specifically, the DNA of the present invention includes DNA comprising the nucleotide sequence from the $98^{th}$ "A" to the $1108^{th}$ "C" of SEQ ID NO:1; the $98^{th}$ "A" to $1381^{st}$ "C" of SEQ ID NO:3; the $98^{th}$ "A" to $1984^{th}$ "G" of SEQ ID NO:5; the $1^{st}$ "A" to $1284^{th}$ "C" of SEQ ID NO:7; and the $1^{st}$ "A" to $1887^{th}$ "G" of SEQ ID NO:9.

Furthermore, the present invention includes DNA that hybridize under stringent conditions to the DNA consisting of any one of the nucleotide sequence of SEQ ID NO:1, 3, 5, 7 or 9, so long as the resulting DNA encodes a protein functionally equivalent to the above-mentioned protein of the invention.

One skilled in the art can suitably select stringent conditions, and for example, low-stringent conditions can be given. Low-stringent conditions are, for example, 42° C., 2×SSC, and 0.1% SDS, and preferably 50° C., 2×SSC, and 0.1% SDS. More preferable are highly stringent conditions which are, for example, 65° C., 2×SSC, and 0.1% SDS. Under these conditions, the higher the temperature, the higher the homology of the obtained DNA will be. The above hybridizing DNA is preferably a natural DNA, such as cDNA and chromosomal DNA.

Moreover, the present invention provides a vector containing a DNA of the present invention as an insert. The vector of the present invention may be useful for maintaining the DNA of the present invention in host cells or producing the protein of the present invention.

If the host cell is $E.\ coli$ (such as JM109, DH5α, HB 101, and XL1Blue), any vector may be used as long as it contains the "ori" for amplification in $E.\ coli$ that enables large-scale preparation, and a selection marker for transformants (for example, a drug-resistance gene that enables selection by a drug such as ampicillin, tetracycline, kanamycin, and chloramphenicol). For example, M13-series vectors, pUC-series vectors, pBR322, pBluescript, pCR-Script, and so on can be used. For the purpose of subcloning or excision of a cDNA, pGEM-T, pDIRECT, pT7, and such may be used as well. For producing the protein of the present invention, an expression vector is especially useful. For example, if the protein is to be expressed in $E.\ coli$, the expression vector must have characteristics such as those mentioned above to be amplified in $E.\ coli$. Additionally, when $E.\ coli$, such as JM109, DH5α, HB101, or XL1 Blue, is used as the host cell, the vector must have a promoter, for example, the lacZ promoter (Ward et al., Nature 341:544–546, 1989; FASEB J. 6:2422–2427, 1992), the araB promoter (Better et al., Science 240:1041–1043, 1988), the T7 promoter, and such, that can efficiently express the desired gene in *E. coli*. Such vectors include pGFX-5X-1 (Pharmacia), "QIAexpress system" (Qiagen), pET (in this case, a host is preferably BL21 which expresses T7 RNA polymerase), and so on, except those mentioned above.

Vectors may be introduced into host cells, for example, by the calcium chloride method or electroporation. The vector may also contain a signal sequence for polypeptide secretion. The pelB signal sequence (Lei et al., J. Bacteriol. 169:4379, 1987) may be used to produce the proteins in the periplasm in *E. coli*.

For example, an expression vector for the preparation of a protein of the present invention may be a mammal-derived expression vector (for example, pcDNA3 (Invitrogen), pEGF-BOS (Nucleic Acids. Res. 18(17):5322, 1990), pEF, and pCDM8); an insect cell-derived expression vector (for example, "Bac-to-BAC baculovirus expression system" (GIBCO BRL), pBacPAK8); a plant-derived expression vector (for example, pMH1 and pMH2); an animal virus-derived expression vector (for example, pHSV, pMV, and pAdexLcw); a retrovirus-derived expression vector (for example, pZIpneo); an yeast-derived expression vector (for example, "Pichia Expression Kit" (Invitrogen), pNV11, and SP-QO1); or a *Bacillus subtilis*-derived expression vectors (for example, pPL608 and pKTH50), other than *E. coli*.

For the expression in animal cells, such as CHO, COS, and NIH3T3 cells, the expression vector must have a promoter such as the SV40 promoter (Mulligan et al., Nature 277:108, 1979), MMLV-LTR promoter, the EF1α promoter (Mizushima et al., Nucleic Acids Res. 18:5322, 1990), and the CMV promoter. More preferably, the vector may contain a marker gene for the selection of transformants (for example, a drug resistance gene for selection by a drug such as neomycin and G418). Such vectors include pMAM, pDR2, pBK-RSV, pBK-CMV, pOPRSV, pOp13, and so on.

Furthermore, in order to achieve stable gene expression and amplification of the copy number of genes in cell, CHO cells deficient in the metabolic pathway for nucleotide synthesis may be used. The CHO cell is transfected with an expression vector comprising the DHFR gene that complements the deficiency (for example, pCHO I), then the vector may be amplified by methotrexate (MTX) treatment. For transient gene expression, COS cells containing a gene expressing the SV40 T-antigen on its chromosome may be used to transform with a vector containing the SV40 replication origin (e.g., pcD). Examples of replication origins to be used in the present invention include those derived from polyomavirus, adenovirus, bovine papilomavirus (BPV), and such. Moreover, to amplify the gene copies in host cell lines, the expression vector may include an aminoglycoside transferase (APH) gene, thymidine kinase (TK) gene, *E. coli* xanthine guanine phosphoribosyl transferase (Ecogpt) gene, dihydrofolate reductase (dhfr) gene, and such as a selective marker.

On the other hand, in vivo expression of a DNA of the present invention in animals may be performed by, for example, by inserting a DNA of the present invention into an appropriate vector and introducing the vector into the body using retrovirus, liposome, cationic liposome, adenovirus, and so on. It is possible to use these methods to perform gene therapy for diseases that arise from mutations in the NR12 gene of the present invention. Examples of vectors used for this purpose include, for example, adenovirus vectors (for example pAdexlcw), retrovirus vectors (for example, pZIP-neo), and such, but are not limited thereto. General gene manipulations, for example, insertion of the DNA of the present invention into a vector, may be performed by using standard methods (Molecular Cloning, 5.61–5.63). The vector may be administered to a living body through ex vivo or in vivo methods.

Another object of the present invention is to provide a transformant that contains a DNA or vector of the present invention. The host cell to insert a vector of the invention is not limited in any way, and for example, *E. coli*, a variety of animal cells, and so on may be used. The host cells of the present invention may be, for example, used as a production system for preparing or expressing a protein of the present invention. In vitro and in vivo production systems are known as production system for producing proteins. Production systems using eukaryotic cells and prokaryotic cells may be used as the in vitro production systems.

When using eukaryotic cells, production system using, for example, animal cells, plant cells, and fungal cells are available as hosts. Exemplary animal cells to be used include mammalian cells such as CHO (J. Exp. Med. 108:945, 1995), COS, 3T3, myeloma, baby hamster kidney (BHK), HeLa, Vero cells; amphibian cells such as *Xenopus* oocytes (Valle et al. Nature 291:338–340, 1981); and insect cells such as Sf9, Sf21, or Tn5. As CHO cells, especially DHFR gene-deficient CHO cell, dhfr-CHO (Proc. Natl. Acad. Sci. USA 77:4216–4220, 1980), and CHO K-1 (Proc. Natl. Acad. Sci. USA 60:1275, 1968) can be suitably used. For large-scale preparation in animal cells, CHO cells may be preferably used. The vector may be introduced into host cells, for example, by the calcium phosphate method, the DEAE dextran method, methods using cationic liposome DOTAP (Boehringer Mannheim), the electroporation method, the lipofection method, and so on.

*Nicotiana tabacum*-derived cells are well known as protein production systems in plant cells, and these can be callus cultured. As fungal cells, yeasts such as the *Saccharomyces* genus, for example, *Saccharomyces cerevisiae*; filamentous fungi, such as *Aspergillus* genus, for example, *Aspergillus niger* are known.

Bacterial cells may be used as prokaryotic production system. As bacterial cells, *E. coli*, for example, JM109, DH5α, HB10, and such, as well as others like *Bacillus subtilis* are known.

Proteins can be obtained by transforming these cells with the objective DNA, and culturing the transformed cells in vitro. Transformants can be cultured according to known methods. For example, DMEM, MEM, RPMI1640, and IMDM can be used as culture media of animal cells. Occasionally, fetal calf serum (FCS) and such serum supplements may be added in the above media; alternatively, a serum-free culture medium may be used. The pH of the culture medium is preferably from about pH 6 to 8. The culturing is usually performed at about 30 to 40° C., for about 15 to 200 hr, and the culture medium changes, aeration, and stirring are done as necessary.

On the other hand, for example, production systems using animals and plants may be given as in vivo protein production systems. The objective DNA is introduced into the animal or plant, and the protein is produced within the plant or animal, and then, the protein is recovered. The term "host" as used in the present invention encompasses such animals and plants as well.

When using animals, mammalian and insect production systems can be used. As mammals, goats, pigs, sheep, mice, and bovines may be used (Vicki Glaser, SPECTRUM Biotechnology Applications, 1993). Alternatively, transgenic animals may also be used when using mammals.

For instance, the objective DNA may be prepared as a fusion gene with a gene encoding a protein intrinsically produced into milk, such as goat β casein. Next, the DNA fragment comprising the fusion gene is injected into goat's embryo, and this embryo is implanted in female goat. The objective protein can be recovered from the milk of the transgenic goats produced from the goat that received the embryo and offspring thereof. To increase the amount of protein-containing milk produced from the transgenic goat, a suitable hormone(s) may be administered to the transgenic goats (Ebert et al., Bio/Technology 12:699–702, 1994).

Silk worms may be used as insects. When using silk worms, they are infected with baculoviruses to which the DNA encoding objective protein has been inserted, and the desired protein can be recovered from body fluids of the silk worm (Susumu et al., Nature 315:592–594, 1985).

When using plants, for example, tobacco can be used. In the case of tobacco, the DNA encoding the objective protein is inserted into a plant expression vector, for example, pMON530, and this is inserted into a bacteria, such as *Agrobacterium tumefaciens*. This bacterium is infected to tobacco, for example, *Nicotiana tabacum*, and it is able to obtain the desired polypeptide from the tobacco leaves (Julian et al., Eur. J. Immunol. 24:131–138, 1994).

Thus-obtained proteins of the present invention are isolated from inside or outside (e.g., medium) of the host cell, and may be purified as a substantially pure homogeneous protein. The separation and purification of the protein can be done using conventional separation and purification methods used to purify proteins and are not limited to any specific method. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, recrystallization, and such may be suitably selected, or combined to separate and purify the protein.

For example, affinity chromatography, ion-exchange chromatography, hydrophobic chromatography, gel filtration, reverse phase chromatography, adsorption chromatography, and such can be exemplified as chromatographies (Strategies for Protein Purification and Characterization: A Laboratory Course Manual. Ed. Daniel R. Marshak et al., Cold Spring Harbor Laboratory Press, 1996). These chromatographies can be performed by liquid chromatography, such as HPLC, FPLC, and such. The present invention encompasses proteins highly purified by using such purification methods.

Proteins can be arbitrarily modified, or peptides can be partially excised by treating the proteins with appropriate protein modification enzymes prior to or after the purification. Trypsin, chymotrypsin, lysyl-endopeptidase, protein kinase, glucosidase, and such are used as protein modification enzymes.

The present invention also provides antibodies that bind to the protein of the invention. There is no particular restriction as to the form of the antibody of the invention and the present invention includes polyclonal antibodies, as well as monoclonal antibodies. The antiserum obtained by immunizing animals such as rabbits with a protein of the invention, as well polyclonal and monoclonal antibodies of all classes, human antibodies, and humanized antibodies produced by genetic recombination, are also included.

A protein of the invention that is used as a sensitizing antigen for obtaining antibodies is not restricted by the animal species from which it is derived, but is preferably a protein derived from mammals, for example, humans, mice, or rats, especially preferably from humans. Protein of human origin can be obtained by using the nucleotide sequence or amino acid sequences disclosed herein.

Herein, an intact protein or its partial peptide may be used as the antigen for immunization. As partial peptides of the proteins, for example, the amino (N)-terminal fragment of the protein, and the carboxy (C)-terminal fragment can be given. "Antibody" as used herein means an antibody that specifically reacts with the full-length or fragments of the protein.

A gene encoding a protein of the invention or a fragment thereof is inserted into a known expression vector, and, by transforming the host cells with the vector described herein, the desired protein or a fragment thereof is recovered from outside or inside the host cells using standard methods. This protein can be used as the sensitizing antigen. Also, cells expressing the protein, cell lysates, or a chemically synthesized protein of the invention may be also used as a sensitizing antigen.

The mammal that is immunized by the sensitizing antigen is not restricted; however, it is preferable to select animals by considering the compatibility with the parent cells used in cell fusion. Generally, animals belonging to the rodentia, lagomorpha, and Primates are used.

Examples of animals belonging to rodentia that may be used include, for example, mice, rats, hamsters, and such. Examples of animals belonging to lagomorpha that may be used include, for example, rabbits. Examples of animals of Primates that may be used include, for example, monkeys. Examples of monkeys to be used include the infraorder catarrhini (old world monkeys), for example, *Macaca fascicularis*, rhesus monkeys, sacred baboons, chimpanzees, and such.

Well-known methods may be used to immunize animals with the sensitizing antigen. For example, the sensitizing antigen is injected intraperitoneally or subcutaneously into mammals. Specifically, the sensitizing antigen is suitably diluted and suspended in physiological saline, phosphate-buffered saline (PBS), and so on, and mixed with a suitable amount of general adjuvant if desired, for example, with Freund's complete adjuvant. Then, the solution is emulsified and injected into the mammal. Thereafter, the sensitizing antigen suitably mixed with Freund's incomplete adjuvant is preferably given several times every 4 to 21 days. A suitable carrier can also be used when immunizing and animal with the sensitizing antigen. After the immunization, the elevation in the level of serum antibody is detected by usual methods.

Polyclonal antibodies against the proteins of the present invention can be prepared as follows. After verifying that the desired serum antibody level has been reached, blood is withdrawn from the mammal sensitized with antigen. Serum is isolated from this blood using conventional methods. The serum containing the polyclonal antibody may be used as the polyclonal antibody, or according to needs, the polyclonal antibody-containing fraction may be further isolated from the serum. For instance, a fraction of antibodies that specifically recognize the protein of the invention may be prepared by using an affinity column to which the protein is coupled. Then, the fraction may be further purified by using a Protein A or Protein G column in order to prepare immunoglobulin G or M.

To obtain monoclonal antibodies, after verifying that the desired serum antibody level has been reached in the mammal sensitized with the above-described antigen, immunocytes are taken from the mammal and used for cell fusion. For this purpose, splenocytes can be mentioned as preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method by Milstein et al. (Galfre et al., Methods Enzymol. 73:3–46,1981).

The hybridoma obtained from cell fusion is selected by culturing the cells in a standard selection medium, for example, HAT culture medium (medium containing hypoxanthine, aminopterin, and thymidine). The culture in this HAT medium is continued for a period sufficient enough for cells (non-fusion cells) other than the objective hybridoma to perish, usually from a few days to a few weeks. Then, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro and fusing the sensitized lymphocytes with myeloma cells derived from human, for example, U266, having a permanent cell division ability (Unexamined Published Japanese Patent Application (JP-A) No. Sho 63-17688).

The monoclonal antibodies obtained by transplanting the obtained hybridomas into the abdominal cavity of a mouse and extracting ascites can be purified by, for example, ammonium sulfate precipitation, protein A or protein G column, DEAE ion exchange chromatography, an affinity column to which the protein of the present invention is coupled, and so on. An antibody of the present invention may be used for the purification or detection of a protein of the present invention. It may also be a candidate as an agonist or antagonist of a protein of the present invention. Furthermore, it is possible to use it in antibody treatment for diseases in which the protein is implicated. For the administration to human body (antibody treatment), human antibodies or humanized antibodies are preferably used because of their reduced immunogenicity.

For example, a human antibody against a protein can be obtained using hybridomas made by fusing myeloma cells with antibody-producing cells obtained by immunizing a transgenic animal comprising a repertoire of human antibody genes with an antigen such as protein, protein-expressing cells, or lysates thereof (see WO92-03918, WO93-2227, WO94-02602, WO94-25585, WO96-33735, and WO96-34096).

Other than producing antibodies using hybridoma, antibody producing immunocytes, such as sensitized lymphocytes that are immortalized by oncogenes, may also be used.

Such monoclonal antibodies can be also obtained as recombinant antibodies produced by using the genetic engineering technique (see, for example, Borrebaeck C. A. K. and Larrick, J. W., THERAPEUTIC MONOCLONAL ANTIBODIES, Published in the United Kingdom by MACMILLAN PUBLISHERS LTD (1990)). Recombinant antibodies are produced by cloning the encoding DNA from immunocytes, such as hybridoma or antibody-producing sensitized lymphocytes, incorporating into a suitable vector, and introducing this vector into a host to produce the antibody. The present invention encompasses such recombinant antibodies as well.

Moreover, the antibody of the present invention may be an antibody fragment or modified-antibody, so long as it binds to a protein of the invention. For instance, Fab, F(ab')$_2$, Fv, or single chain Fv (scFv) in which the H chain Fv and the L chain Fv are suitably linked by a linker (Huston et al., Proc. Natl. Acad. Sci. USA 85:5879–5883, 1988) can be given as antibody fragments. Specifically, antibody fragments are generated by treating antibodies with enzymes, for example, papain or pepsin. Alternatively, they may be generated by constructing a gene encoding an antibody fragment, introducing this into an expression vector, and expressing this vector in suitable host cells (see, for example, Co et al., J. Immunol. 152:2968–2976, 1994; Better et al., Methods Enzymol. 178:476–496, 1989; Pluckthun et al., Methods Enzymol. 178:497–515, 1989; Lamoyi, Methods Enzymol. 121:652–663, 1986; Rousseaux et al., Methods Enzymol. 121:663–669, 1986; Bird et al., Trends Biotechnol. 9:132–137, 1991).

As modified antibodies, antibodies bound to various molecules, such as polyethylene glycol (PEG), can be used. The antibodies of the present invention encompass such modified antibodies as well. To obtain such a modified antibody, chemical modifications are done to the obtained antibody. These methods are already established and conventional in the field.

An antibody of the present invention may be obtained as a chimeric antibody, comprising non-human antibody-derived variable region and human antibody-derived constant region, or as a humanized antibody comprising non-human antibody-derived complementarily determining region (CDR), human antibody-derived framework region (FR), and human antibody-derived constant region by using conventional methods.

Antibodies thus obtained can be purified to uniformity. The separation and purification methods used in the present invention for separating and purifying the antibody may be any method usually used for proteins. For example, column chromatography, such as affinity chromatography, filter, ultrafiltration, salting-out, dialysis, SDS polyacrylamide gel electrophoresis, isoelectric focusing, and others, may be appropriately selected and combined to isolate and purify the antibodies (Antibodies: A Laboratory Manual. Ed Harlow and David Lane, Cold Spring Harbor Laboratory, 1988); however, the invention is not limited thereto. Antibody concentration of the above mentioned antibody can be assayed by measuring the absorbance, or by the enzyme-linked immunosorbent assay (ELISA), etc.

Protein A or Protein G column can be used for the affinity chromatography. Protein A column may be, for example, Hyper D, POROS, Sepharose F. F. (Pharmacia), etc.

Other chromatography may also be used, for example, such as ion-exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). These may be performed on liquid-phase chromatography such as HPLC, FPLC, and so on.

Examples of methods that assay the antigen-binding activity of the antibodies of the invention include, for example, measurement of absorbance, enzyme-linked immunosorbent assay (ELISA), enzyme immunoassay (EIA), radioimmunoassay (RIA), and/or immunofluorescence. For example, when using ELISA, a protein of the invention is added to a plate coated with the antibodies of the present invention, and then, the objective antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (Pharmacia) may be used.

By using these methods, the antibody of the invention and a sample presumed to contain a protein of the invention are contacted, and the protein of the invention is detected or assayed by detecting or assaying the immune complex formed between the above-mentioned antibody and the protein.

A method of detecting or assaying a protein of the invention is useful in various experiments using proteins as it can specifically detect or assay the proteins.

Another object of this invention is to provide a polynucleotide of at least 15 nucleotides that is complementary to the DNA encoding human NR12 protein (SEQ ID NO:1, 3, 5, 7 or 9) or its complementary strand.

Herein, the term "complementary strand" is defined as one strand of a double strand polynucleotide composed of A:T and G:C base pairs to the other strand. Also, "complementary" is defined as not only those completely matching within a continuous region of at least 15 nucleotides, but also having a homology of at least 70%, preferably 80%, more preferably 90%, and most preferably 95% or higher within that region. The homology may be determined using the algorithm described herein.

Probes and primers for detection or amplification of the DNA encoding a protein of the invention, or a nucleotide or nucleotide derivative for the suppression of the protein expression (such as, antisense oligonucleotide and ribozyme) are included in these polynucleotides. Such polynucleotides may be also used for preparing DNA chips.

The antisense oligonucleotides that hybridize with a portion of the nucleotide sequence of any of SEQ ID NO:1, 3, 5, 7, and 9 are also included in the antisense oligonucleotides of the present invention. These antisense oligonucleotides are preferably directed against a sequence which contains at least 15 continuous nucleotides comprised in any one of the nucleotide sequence of SEQ ID NO:1, 3, 5, 7, and 9. More preferably, it is the antisense oligonucleotide against at least 15 continuous nucleotides containing a translation start codon.

Derivatives or modified products of antisense oligonucleotides can be used as antisense oligonucleotides. Examples of such modified products include, for example, lower alkyl phosphonate modifications such as methyl-phosphonate-type or ethyl-phosphonate-type; phosphorothioate modifications; phosphoroamidate modifications, and such.

The term "antisense oligonucleotides" as used herein means, not only those in which the nucleotides corresponding to those constituting a specified region of a DNA or mRNA are entirely complementary, but also those having a mismatch of one or more nucleotides, so long as the DNA or mRNA and the oligonucleotide can specifically hybridize with the nucleotide sequence of SEQ ID NO:1, 3, 5, 7 or 9.

The antisense oligonucleotide derivatives of the present invention act upon cells producing a protein of the invention by binding to the DNA or RNA encoding the protein to inhibit its transcription or translation, and to promote the degradation of the mRNA, and have an effect of suppressing the function of the protein of the invention by suppressing the expression of the protein.

An antisense oligonucleotide derivative of the present invention can be made into an external preparation, such as a liniment or a poultice, by mixing with a suitable base material, which is inactive against the derivatives.

Also, as needed, the derivatives can be formulated into tablets, powders, granules, capsules, liposome capsules, injections, solutions, nose-drops, freeze-dried agents, and such by adding excipients, isotonic agents, solubilizing agents, stabilizers, preservative substance, pain-killers, and such. These can be prepared using conventional methods.

An antisense oligonucleotide derivative is given to the patient by directly applying it onto the ailing site, by injecting it into the blood vessel and such, so that it will reach the ailing site. An antisense-mounting medium can also be used to increase durability and membrane-permeability. Examples are, liposome, poly-L-lysine, lipid, cholesterol, lipofectin or derivatives of them.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide of the present invention is useful in inhibiting the expression of the protein of the invention, and therefore is useful in suppressing the biological activity of the proteins of the invention. Also, expression-inhibitors comprising the antisense oligonucleotide of the invention are useful, because of their capability to suppress the biological activity of the proteins of the invention.

Proteins of this invention are useful in screening for compounds that bind to the protein. That is, the proteins are used in a method of screening for compounds that bind to the proteins of this invention, in which the method comprises bringing proteins of this invention into contact with a test sample that is expected to contain a compound that may bind to the proteins and selecting the compound with the activity of binding to the proteins of the invention.

Proteins of this invention to be used in the screening of the invention may be any of recombinant, natural, or partial peptides. Also, they may be in the form of proteins expressed on the cell surface or membrane fractions. Test samples to be used in the screening method of the present invention are not limited, but may be, for example, cell extracts, cell culture supernatants, microbial fermentation products, extracts of marine organisms, plant extracts, purified or partly purified proteins, peptides, non-peptide compounds, synthetic low molecular compounds, or natural compounds. The proteins of this invention may be exposed to the sample as purified protein or soluble proteins, in a form bound to a carrier, as fusion proteins with another protein, in a form expressed on the cell surface, or as membrane fractions.

A protein of the present invention may be used to screen for other proteins that bind to the target protein (such as ligands) using a variety of methods known to one skilled in the art. These screening processes can be carried out, for example, by the immunoprecipitation method. Specifically, the method can be carried out as follows. The gene encoding a protein of the present invention is expressed by inserting the gene into an expression vector for foreign gene expression like pSV2neo, pcDNA I, pCD8, and such, and expressing the gene in animal cells, etc. Any generally used promoters may be employed for the expression, including the SV40 early promoter (Rigby in Williamson (ed.), Genetic engineering, Vol. 3. Academic Press, London, p. 83–141, 1982), the EF-1α promoter (Kim et al., Gene 91:217–223, 1990), the CAG promoter (Niwa et al., Gene 108:193–200, 1991), the RSV LTR promoter (Cullen, Methods in Enzymology 152:684–704, 1987), the SRα promoter (Takebe et al., Mol. Cell. Biol. 8:466, 1988), the CMV immediate early promoter (Seed et al., Proc. Natl. Acad. Sci. USA 84:3365-3369, 1987), the SV40 late promoter (Gheysen et al., J. Mol. Appl. Genet. 1:385–394, 1982), the Adenovirus late promoter (Kaufman et al., Mol. Cell. Biol. 9:946, 1989), the HSV TK promoter, and so on.

Transfer of a foreign gene into animal cells for its expression can be performed by any of the following methods, including the electroporation method (Chu et al., Nucl. Acid Res. 15:1311–1326, 1987), the calcium phosphate method (Chen et al., Mol. Cell. Biol. 7:2745–2752, 1987), the DEAE dextran method (Lopata et al., Nucl. Acids Res. 12:5707–5717, 1984; Sussman et al., Mol. Cell. Biol. 4:1642–1643, 1985), the lipofectin method (Derijard, Cell 7:1025–1037, 1994; Lamb et al., Nature Genetics 5:22–30, 1993; Rabindran et al., Science 259:230–234, 1993), and such. A protein of the present invention can be expressed as a fusion protein having the recognition site (epitope) for a monoclonal antibody by introducing a recognition site (epitope) for a monoclonal antibody, the specificity of which has been established, into the N- or C-terminus of the protein of the present invention. For this purpose, a commercial epitope-antibody system can be utilized (Exp. Med. 13:85–90, 1995). Vectors are commercially available which are capable of expressing fusion proteins with P-galactosidase, maltose binding protein, glutathione S-transferase, green florescence protein (GFP), and such, via the multicloning site.

To minimize the alteration of the properties of a protein of this invention arising from the formation into a fusion protein, a the fusion protein may be prepared by introducing only a small epitope portion comprising several to ten amino acids as reported in the literature. For example, the epitopes of polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (epitope on the monoclonal phage), and such, and monoclonal antibodies to recognize these epitopes can be utilized as the epitope-antibody system for screening proteins binding to the protein of the present invention (Exp. Med. 13:85–90, 1995).

In immunoprecipitation, immune complexes are formed by adding these antibodies to cell lysate prepared using suitable detergents. This immune complex consists of a protein of the present invention, a protein capable of binding to the protein, and an antibody. The immunoprecipitation can also be conducted using an antibody against a protein of the present invention besides antibodies against the above epitopes. An antibody against the protein of the present invention can be prepared, for example, by inserting a gene encoding a protein of the present invention into an appropriate E. coli expression vector to express the gene in E. coli, purifying the expressed protein, and immunizing rabbits, mice, rats, goats, chickens, and such, with the purified protein. The antibody can also be prepared by immunizing the above-described animals with partial peptides of the protein of the present invention.

Immune complexes can be precipitated using, for example, Protein A Sepharose or Protein G Sepharose in case where the antibody is a mouse IgG antibody. In addition, in the case where the protein of the present invention is prepared as a fusion protein with the epitope of, for example, GST, and such, the immune complex can be formed using a substance that specifically binds to these epitopes, such as glutathione-Sepharose 4B, and such, giving the same result as in the case where the antibody for the protein of the present invention is used.

Immunoprecipitation, in general, may be performed following, or according to, for example, the method described in the literature (Harlow, E. and Lane, D.: Antibodies pp. 511–552, Cold Spring Harbor Laboratory publications, New York, 1988).

SDS-PAGE is generally used for the analysis of immunoprecipitated proteins, and bound proteins can be analyzed based on the molecular weight of proteins using a gel of an appropriate concentration. In this case, although proteins bound to a protein of the present invention, in general, are hardly detectable by the usual protein staining methods, such as Coomassie staining and silver staining, the detection sensitivity can be improved by culturing cells in a culture medium containing radio isotope-labeled $^{35}$S-methionine and $^{35}$S-cystein to label proteins inside the cells, and detecting the labeled proteins. Once the molecular weight of the protein is determined, the desired protein can be purified directly from SDS-polyacrylamide gel and sequenced.

In addition, isolation of proteins binding to a protein of the present invention can be also performed using, for example, the West-Western blotting analysis (Skolnik et al., Cell 65:83–90, 1991). Specifically, a cDNA library is constructed from cells, tissues, and organs in which protein binding to the protein of this invention is expected to be expressed by using phage vectors (such as, λgt11 and ZAP), proteins expressed on LB-agarose are fixed on a filter, which is then reacted with a purified and labeled protein of the present invention, and plaques expressing proteins binding to the protein of the present invention are detected by the label. Methods for labeling a protein of the invention include methods utilizing the binding of biotin and avidin, methods utilizing antibodies specifically binding to the protein of the present invention, or peptides or polypeptides (for example, GST, etc.) fused with the protein of the present invention, methods utilizing radioisotope and fluorescence, and such.

Further, another embodiment of the screening method of the present invention is exemplified by a method utilizing the two-hybrid system using cells (Fields et al., Trends Genet. 10:286–292, 1994; Dalton et al., Cell 68:597–612, 1992; "MATCHMAKER Two-Hybrid System", "Mammalian MATCHMAKER Two-Hybrid Assay Kit", "MATCHMAKER One-Hybrid System" (all from Clontech); "HybriZAP Two-Hybrid Vector System" (Stratagene)). In the two-hybrid system, a protein of this invention may be fused to the DNA binding domain of SRF or GAL4, and expressed in yeast cells. A cDNA library is constructed from cells predicted to express proteins that bind to the protein of this invention, wherein the cDNA library is constructed in such a way that the proteins are expressed as fusion proteins with transcription activation regions of VP 16 or GAL4. The cDNA library is transfected into the aforementioned yeast cells, and then positive clones are detected so as to isolate the cDNA-derived from the library (i.e., expression of a protein that binds to the protein of the invention in yeast cell leads to the binding of the two proteins, and results in the activation of the reporter gene, which allows for the detection positive clones). The protein encoded by the isolated cDNA may be obtained by introducing the cDNA into E. coli and expressing it therein. Thus, it is possible to prepare proteins that bind to a protein of this invention and genes encoding them. The reporter gene to be used in the two-hybrid system may be any suitable gene, such as HIS3 gene, Ade2 gene, LacZ gene, CAT gene, luciferase gene, or plasminogen activator inhibitor type1 (PAI-1) gene, but is not limited thereto.

Screening for compounds which bind to a protein of the present invention can be also carried out using affinity chromatography. For example, a protein of the invention is immobilized on a carrier in the affinity chromatography column, to which a test sample, which is expected to express a protein binding to the protein of the invention, is applied. Samples may be, for example, cell extracts, cell lysates, etc. After loading the test sample, the column is washed, and proteins which binds to the protein of the invention can be obtained.

The obtained protein may be analyzed for its amino acid sequence to synthesize oligonucleotide probes, which may then be used to screen a cDNA library to obtain a DNA encoding the protein.

A biosensor that utilizes surface plasmon resonance phenomenon may be used to detect or measure the bound compound. Such biosensors (for example, BIAcore (Pharmacia)) may enable the observation of the interaction at real-time using a small amount of protein without the need for labeling. Thus, it is possible to assess the interaction between the protein of the invention and test compounds using biosensors such as BIAcore.

Moreover, compounds that bind to a protein of the invention (including agonists and antagonists), which compounds are not always proteins, may be isolated using a variety of methods known to one skilled in the art. For instance, the protein of the invention may be fixed and exposed to synthetic compounds, a bank of natural substances, or a random phage peptide display library to screen for molecules that bind to the protein. Alternatively, high-throughput screening using combinatorial chemistry techniques may be performed (Wrighton et al., Science 273:458–64, 1996; Verdine, Nature 384:11–13, 1996; Hogan, Jr., Nature 384: 17–9, 1996).

Screening of a ligand that binds to a protein of the invention may be performed as follows. The extracellular domain of a protein of the invention is fused to the intracellular domain including the transmembrane domain of a hemopoietin receptor protein that has a known signal transducing ability to prepare a chimeric receptor. The chimeric receptor may be expressed on the cell surface of a suitable cell line, preferably a cell line that can survive and proliferate only in the presence of a suitable growth proliferative factor (growth factor-dependent cell line). Then, the cell line may be cultured in medium supplemented with a sample material in which a variety of growth factors, cytokines, or hemopoietic factors might be expressed. According to this method, the growth factor-dependent cell line can only survive and proliferate when the sample contains an appropriate ligand that specifically binds to the extracellular domain of the protein of the invention. The known hemopoietin receptors, such as the thrombopoietin receptor, erythropoietin receptor, G-CSF receptor, gp130, and so on may be used. The partner for constructing a chimeric receptor for the screening system of the invention is not limited to the above receptors so long as its intracellular domain provides a structure necessary for the signal transduction activity. The growth factor-dependent cell line may be, for example, IL-3-dependent cell lines such as BaF3 or FDC-P1.

In a rare case, the ligand that specifically binds to a protein of the invention may not be a soluble protein but a membrane-bound protein. In this case, screening can be done using a protein comprising only the extracellular domain of the protein of the invention, or a fusion protein in which the extracellular domain is attached to a part of other soluble proteins. Such proteins are labeled before they are used for measuring the binding with the cells that are expected to express the ligand. The former protein, comprising only the extracellular domain, may be a soluble receptor protein artificially constructed through introducing a stop codon into the N-terminal side of the transmembrane domain, or a soluble protein such as NR12-1. The latter fusion protein may be a protein in which the Fc region of immunoglobulin, or FLAG peptide is attached to the C-terminus of the extracellular domain. These labeled soluble proteins can also be useful in detection by the above-described West-western blotting method.

A chimeric protein of the extracellular domain of a protein of this invention and the Fc region of an antibody (such as human IgG antibody) may be purified using Protein A column, etc. Such an antibody-like chimeric protein retains its ligand binding activity. Thus, the protein may be appropriately labeled with an isotope and so on, and used for the screening of a ligand (Suda et al., Cell 175:1169–1178, 1993). Some cytokines, such as molecules of the TNF family, primarily exist in a membrane-bound form, so such ligands may be isolated by exposing the antibody-like chimeric protein to a variety of cells and selecting cells based on the binding activity to the protein. Alternatively, ligands may be isolated according to the same method by using cells to which a cDNA library is introduced. Furthermore, the antibody-like chimeric protein may also be used as an antagonist.

The compound isolated by the above screening may be a candidate for drugs that activate or inhibit the activity of a protein of this invention. It is possible to apply such compounds for the treatment of the disease arising from aberrant expression or functional disorder of a protein of the present invention. The compound obtained using the screening method of the invention includes compounds resulting from the modification of the compound having the activity to bind to the protein of the invention by adding, deleting, and/or replacing a part of the structure.

When using the isolated compound or a protein of the present invention (decoy type (soluble form)) as a pharmaceutical for humans and other mammals, for example, mice, rats, guinea pigs, rabbits, chicken, cats, dogs, sheep, pigs, bovines, monkeys, sacred baboons, chimpanzees, the isolated compound can be directly administered or can be formulated into a dosage form using known pharmaceutical preparation methods. For example, according to the need, the pharmaceuticals can be taken orally, as sugar-coated tablets, capsules, elixirs and microcapsules, or parenterally, in the form of injections of sterile solutions, suspensions with water, or any other pharmaceutically acceptable liquid. For example, the compounds can be mixed with a pharmacologically acceptable carrier or medium, specifically, sterilized water, physiological saline, plant-oil, emulsifiers, suspending agent, surfactants, stabilizers, flavoring agents, excipients, vehicles, preservatives and binders, in a unit dosage form required for generally accepted drug implementation. The amount of active ingredient in these preparations makes a suitable dosage acquirable within the indicated range.

Examples of additives which can be mixed to tablets and capsules include: binders, such as gelatin, corn starch, tragacanth gum and gum acacia; excipients, such as crystalline cellulose; swelling agents, such as corn starch, gelatin and alginic acid; lubricants, such as magnesium stearate; and sweeteners, such as sucrose, lactose or saccharin; flavoring agents, such as peppermint, *Gaultheria adenothrix* oil and cherry. When the unit dosage form is a capsule, a liquid carrier, such as oil, can also be included in the above ingredients. Sterile composites for injections can be formulated following normal drug implementations, using vehicles such as distilled water used for injections.

For example, physiological saline, glucose, and other isotonic liquids, including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, and non-ionic surfactants, such as Polysorbate 80 (TM) and HCO-50.

Sesame oil or soy-bean oil can be used as an oleaginous liquid and may be used in conjunction with benzyl benzoate or benzyl alcohol as solubilizers; may be formulated with a buffer such as phosphate buffer and sodium acetate buffer; and may be used in conjunction with a pain-killer such as procaine hydrochloride, a stabilizer such as benzyl alcohol and phenol, and an anti-oxidant. The prepared injection is filled into a suitable ampule.

Methods well known to those skilled in the art may be used to administer the pharmaceutical compound to patients, for example as intraarterial, intravenous, percutaneous injections and also as intranasal, transbronchial, intramuscular or oral administrations. The dosage varies according to the body-weight and age of the patient, the administration method, and such, but one skilled in the art can suitably select them. If said compound is encodable by a DNA, said DNA can be inserted into a vector for gene therapy to perform the therapy. The dosage and method of administration vary according to the body-weight, age, and symptoms of a patient, but one skilled in the art can select them suitably.

For example, the dosage of the protein of this invention (decoy form (soluble form)) may vary depending on the subject of administration, target organ, symptom, and method for administration. However, it may be injected to a normal adult (body weight, 60 kg) at a dose of about 100 μg to 10–20 mg per day.

For example, although there are some differences according to the symptoms, the dose of a compound that binds with a protein of the present invention, or a compound that inhibits the activity of a protein of this invention is typically about 0.1 mg to about 100 mg per day, preferably about 1.0 mg to about 50 mg per day, and more preferably about 1.0 mg to about 20 mg per day, when administered orally to a normal adult (weight 60 kg).

When the protein is administered parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals, it is possible to administer an amount converted to 60 kg of body-weight or surface area.

All publications and patents cited herein are incorporated by reference in their entirety.

DESCRIPTION OF DRAWINGS

FIG. 1 shows the partial nucleotide sequence of AL109843 identified in the htgs database (SEQ ID NO:23). The deduced amino acid sequence is shown under the predicted exon sequence (SEQ ID NO:24). The YR motif sequence and WS motif that were used as the target are boxed.

FIG. 2 shows partial amino acid sequences of NR12 found in the sequence of AL109843 (from the top SEQ ID NOs: 25–29), and those of known hemopoietin receptors having homology thereto. Identical amino acid sequences are boxed and similar amino acid sequences are shadowed. Gap spaces are underlined. Known hemopoietin receptors are, from top, human gp130 (SEQ ID NO:30), human NR9 (SEQ ID NO:31), human prolactin receptor (SEQ ID NO:32), human IL-7 receptor (SEQ ID NO:33), and human LIF receptor (SEQ ID NO:34).

FIG. 4 shows the nucleotide sequence of the full-length NR12.1 cDNA that was obtained by combining the 5'-RACE and 3'-RACE products (SEQ ID NO:1). The deduced amino acid sequence encoded by NR12.1 is also shown (SEQ ID NO:2). The amino acid sequence predicted to be the secretion signal is underlined. Conserved cysteine residues, and the amino acid sequences of YR motif and WS motif are boxed.

FIG. 5 shows the nucleotide sequence of the full-length NR12.2 cDNA that was obtained by combining the 5'-RACE and 3'-RACE products (SEQ ID NO:3). The amino acid sequence encoded by NR12.2 is also shown (SEQ ID NO:4). The predicted secretion signal sequence is underlined. The predicted transmembrane region is shadowed. Conserved cysteine residues in the extracellular region, and amino acid sequences of YR motif and WS motif are boxed.

FIG. 6 shows the nucleotide sequence of full-length NR12.3 cDNA that was obtained by combining the 5'-RACE and 3'-RACE products (SEQ ID NO:5). The amino acid sequence encoded by NR12.3 is also shown (SEQ ID NO:6). The predicted secretion signal is underlined. Conserved cysteine residues, and the amino acid sequences of YR motif and WS motif are boxed.

FIG. 7 is a continuation of FIG. 6.

FIG. 10 is a schematic illustration of the structure of the NR12 fusion protein to be expressed from the expression vector construct in the mammalian cell.

FIG. 11 shows the nucleotide sequence of full-length NR12.4 cDNA that was obtained by combining the 5'-RACE and 3'-RACE products (SEQ ID NO:7). The amino acid sequence encoded by NR12.4 is also shown (SEQ ID NO:8). The predicted secretion signal is underlined. Conserved cysteine residue, and amino acid sequences of YR motif and WS motif are boxed.

FIG. 12 is a continuation of FIG. 11.

FIG. 13 shows the nucleotide sequence of full-length NR12.5 cDNA (SEQ ID NO:9). The amino acid sequence encoded by NR12.5 is also shown (SEQ ID NO:10). The predicted secretion signal is underlined. The predicted transmembrane sequence is shaded. Conserved cysteine residue in the extracellular region, and amino acid sequences of YR motif and WS motif are boxed.

FIG. 14 is a continuation of FIG. 13.

DETAILED DESCRIPTION

Figure 3:
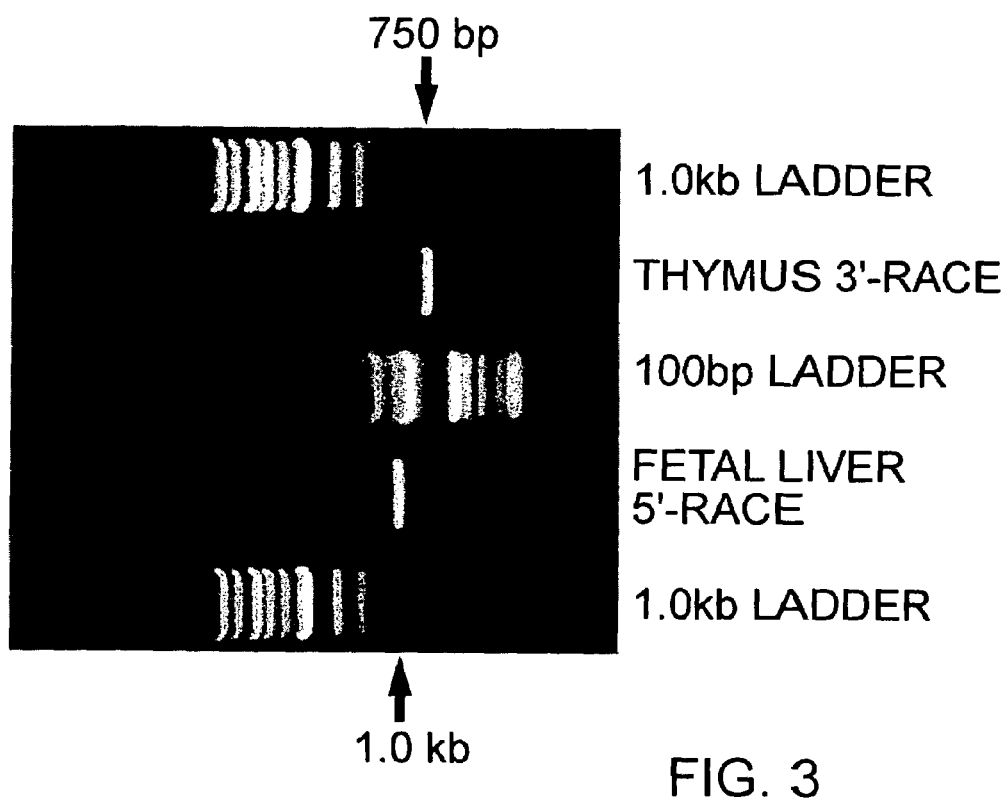
FIG. 3 shows a photograph demonstrating the results of PCR analysis, showing expressed products amplified by 5'-RACE and 3'-RACE using the oligonucleotide primers designed against the predicted WS exon within the AL109843 sequence. Specific products by PCR are shown with arrows.

The present invention will be explained below with reference to examples, but it is not construed as being limited thereto.

EXAMPLE 1

Isolation of NR12 Gene (1) Primary Screening by TblastN Search

Although sequencing of human genome is promoted extensively by human genome projects of institutes, the proportion of completely finished sequences to the whole human genome has not reached even 10%. However, information provided by above projects until today is counted as a good means for searching target genes, determining nucleotide sequences, and mapping genes. The informational basis of the above sequences consists of large information provided by the assembly of bacterial artificial chromosome (BAC) and yeast artificial chromosome (YAC), which aims to form a complete database in the future. The present inventors identified a human gene encoding a part of a novel hemopoietin receptor protein from a BAC clone sequence in one of public databases, "High Throughput Genomic Sequence (htgs)" of GenBank.

As mentioned above, the present inventors found motif sequences conserved in the hemopoietin receptor family, namely (Tyr/His)-Xaa-(Hydrophobic/Ala)-(Gln/Arg)-Hydrophobic-Arg motif (YR motif) in the extracellular region, and Trp-Ser-Xaa-Trp-Ser (SEQ ID NO:21) motif (WS motif) located around the C-terminus. However, it is extremely difficult to design oligonucleotide probe that includes both motif sequences comprehensively. Therefore, the inventors conducted in silico database search using partial amino acid sequences from the fragment of known hemopoietin receptor proteins including both motifs as the query. Fragmentation of partial amino acid sequences that may be used as a query was examined using the human receptors shown in table 1 as the sequence of known hemopoietin receptors. According to the genomic structure of the known hemopoietin receptor sequences, the exons encoding these YR motif and WS motif were about 50 to 70 amino acids long, and the exon proximal to it to the N-terminus (PP exon) was also about 50 to 70 amino acids long. Thus, a sequence containing both exons consisting of about 120 amino acids were cut to prepare a query sequence for convenience' sake. Although the length of the partial amino acid sequence used as the query sequence varied depending on each known hemopoietin receptor, the feature of the structure was conserved. A sequence that ranges from one or more proline residues located near the initiation site in the PP exon to the amino acid residue located about 10 amino acids to the C-terminus of the WS motif termination in the WS exon was extracted as the query sequences from all known hematopoietic receptor sequences.

The known hemopoietin receptors used as query sequences for the database search is shown in the table. The amino acid residues conserved among motif sequences are shown in bold with underline.

TABLE 1

| Human Receptors | GenBank Accession # | YR-motif Sequence | WS-motif Sequence |
|---|---|---|---|
| LIF-R | NM_002310 | YTFRIR (SEQ ID NO:35) | WSKWS (SEQ ID NO:57) |
| gp130 | NM_002184 | YVFRIR (SEQ ID NO:36) | WSDWS (SEQ ID NO:58) |
| IL-1.2Rβ1 | NP_005526 | QEFQLR (SEQ ID NO:37) | WSKWS (SEQ ID NO:57) |
| IL-1.2Rβ2 | NM_001559 | YEFQIS (SEQ ID NO:38) | WSDWS (SEQ ID NO:58) |
| G-CSFR | NM_000760 | YTLQIR (SEQ ID NO:39) | WSDWS (SEQ ID NO:58) |
| EPO-R | M34986 | YTFAVR (SEQ ID NO:40) | WSAWS (SEQ ID NO:59) |
| TPO-R | M90103 | YRLQLR (SEQ ID NO:41) | WSSWS (SEQ ID NO:60) |
| Leptin-R | U50748 | YAVQVR (SEQ ID NO:42) | WSNWS (SEQ ID NO:61) |
| IL-3Rα | M74782 | YTVQIR (SEQ ID NO:43) | LSAWS (SEQ ID NO:62) |
| IL-4R | NM_000418 | YRARVR (SEQ ID NO:44) | WSEWS (SEQ ID NO:63) |
| IL-5Rα | M96651 | YDVQVR (SEQ ID NO:45) | WSEWS (SEQ ID NO:63) |
| IL-6R | NM_000565 | HVVQLR (SEQ ID NO:46) | WSEWS (SEQ ID NO:63) |
| IL-7R | NM_002185 | YEIKVR (SEQ ID NO:47) | WSEWS (SEQ ID NO:63) |
| IL-11Rα | U32324 | HAVRVS (SEQ ID NO:48) | WSTWS (SEQ ID NO:64) |
| IL-13Rα | NM_001560 | NTVRIR (SEQ ID NO:49) | WSNWS (SEQ ID NO:61) |
| IL-2Rβ | A28052 | YEFQVR (SEQ ID NO:50) | WSPWS (SEQ ID NO:65) |
| IL-2Rγ | NM_000206 | YTFRVR (SEQ ID NO:51) | WSEWS (SEQ ID NO:63) |
| GM-CSFR | M64445 | HSVKIR (SEQ ID NO:52) | WSSWS (SEQ ID NO:60) |
| CNTF-R | NM_001842 | YIIQVA (SEQ ID NO:53) | WSDWS (SEQ ID NO:58) |
| PRL-R | NM_000949 | YLVQVR (SEQ ID NO:54) | WSAWS (SEQ ID NO:59) |
| NR6(CRLF1) | NM_004750 | YFVQVR (SEQ ID NO:55) | WSEWS (SEQ ID NO:63) |
| NR9(CREME9) | AF120151 | YQFRVC (SEQ ID NO:56) | WSPWS (SEQ ID NO:65) |

The above queries were used to search on the htgs database in GenBank using TblastN (Advanced TblastN 2.0.9) program. The default values (Expect=100, Descriptions=250, and Alignments=250) were used as parameters for the search. As a result, the search resulted in many false positive clones, and those clones which both of the YR motif and WS motif were not encoded in the same reading frame, or that contained a stop codon between the two motifs were excluded. Also those clones containing only the YR motif but not the WS motif were also excluded, because, as mentioned above, the YR motif is not a completely established consensus sequence. Therefore, the conservation of the WS motif was considered predominant. As a result of the above selection, positive clones of primary search shown in table 2 were chosen from about 1000 pseudo-positive clones obtained by the TblastN search.

Positive clones obtained by the primary search against htgs database having the target motif sequence with high probability were selected, and are shown in the table. Conserved amino acid residues are shown in bold with underline in the motif sequences.

TABLE 2

| GenBank Accession # | Motif Sequence | Note |
|---|---|---|
| AC008048 | WSPWS (SEQ ID NO:65) | IL-2Rbeta |
| AC007174 | WSEWS (SEQ ID NO:63) | IL-5R |
| AL031406 | WSTWS (SEQ ID NO:64) | CH.22 |
| AC003656 | WSGWS (SEQ ID NO:66) | CH.21 |
| AC008663 | WSKWS (SEQ ID NO:57) | CH.5 |
| AC008614 | WSGWS (SEQ ID NO:66) | CH.5 |
| AC008532 | WSGWS (SEQ ID NO:66) | CH.19 |
| AC009267 | WSTWS (SEQ ID NO:64) | CH.18 |
| AC007596 | WSSWS (SEQ ID NO:60) | CH.16 |
| AC007227 | WGEWS (SEQ ID NO:67) | CH.16 |
| AL031123 | WSDWA (SEQ ID NO:68) | CH.6 |
| AC005911 | WGEWS (SEQ ID NO:67) | CH.12 |
| AL096870 | WSNWK (SEQ ID NO:69) | CH.14 |
| Z97201 | WSNWK (SEQ ID NO:69) | CH.12 |
| AC007902 | WSGWS (SEQ ID NO:66) | CH.18 |
| AC008536 | WSMWS (SEQ ID NO:70) | CH.5 |
| AC006176 | WSGWS (SEQ ID NO:66) | CH.10 |
| AC004846 | WSQWS (SEQ ID NO:71) | none |
| AL109843 | WQPWS (SEQ ID NO:72) | CH.1(NR12) |
| AC003656 | WSFWG (SEQ ID NO:73) | CH.21 |
| AC005143 | TSGWS (SEQ ID NO:74) | CH.15 |
| AL109743 | WSGWS (SEQ ID NO:66) | CH.1 |
| AC008403 | WSAWS (SEQ ID NO:59) | CH.19 |
| AL032818 | WSGWS (SEQ ID NO:66) | CH.22 |
| Z93017 | WSGWS (SEQ ID NO:66) | CH.6 |
| AC009456 | WSRWS (SEQ ID NO:75) | CH.18 |
| AC008427 | WSEGS (SEQ ID NO:76) | CH.5 |
| AL096791 | WSQWS (SEQ ID NO:71) | CH.X |

(2) Secondary Screening by BlastX Search

First, nucleotide sequences around the sequence which were positive to the query sequence in the primary search were cut from each of the 28 positive clones of TblastN primary search shown in table 2. Using these sequences as the query, the nr database in GenBank was searched again using the BlastX (Advanced BlastX 2.0.9) program. The query sequence consisted of a nucleotide sequence of 240 bp in total, which contains the sequence approximately 200 bp upstream of the sequence that may encode the WS motif, for convenience sake. Because, as mentioned above, the exon encoding the WS motif was as short as approximately 50 to 70 amino acids in the genome structure of known hemopoietin receptors, the prepared query sequence of 240 bp long is expected to cover the exon sufficiently. The value of "Expect=100, Descriptions=100, Alignments=100, Filter=default" was used for the BlastX search. It was expected that positive clones showing at least homology with multiple different known hemopoietin receptors would be selected as positive clones of secondary search encoding hematopoietin receptor family members from the positive clones of the secondary search according to the search.

As a result of the above two-step Blast search, three clones (AC008048, AC007174, and AL109843) among the human genome clones shown in table 2 were successfully identified as positive clones of the secondary search. However, AC008048 and AC007174 were revealed to be genome sequences that encode the human IL-2 receptor beta strand and human IL-5 receptor, respectively. AL109843 alone was inferred to encode the target novel hemopoietin receptor. Therefore, this clone was named NR12, and was determined to isolate the full-length cDNA.

AL109843 is a genome draft sequence derived from human chromosome 1 submitted to htgs database at 16$^{th}$ Aug. 1999, and has a length of 149104 bp. However, nucleotide sequences at 10 positions, approximately 8000 bp in total, remains undetermined at this time. The existence of a WS exon could be predicted in the sequence of AL109843 which were positive in the TblastN primary search as shown in FIG. 1. The YR motif, [YVFQVR; SEQ ID NO:77] sequence, and WS motif, [WQPWS; SEQ ID NO:72] sequence, was recognized in the sequence. The comparison of the amino acid sequence of NR12 to that of the known hematopoietin receptor, which were detected to have homology in BlastX secondary search, are shown in FIG. 2. Based on the above result, specific oligonucleotide primers were designed on the exon sequence that were predicted in the AL109843 sequence, and these primers were used in the 5'-RACE method and the 3'-RACE method described later on.

(3) Design of Oligonucleotide Primers

As described above, exon sites were predicted on AL109843 sequences, and these were used to design the following oligonucleotide primers specific for NR12. Three sense primers (NR12-S1, NR12-S2, and NR12-S3; oriented downstream) and three antisense primers (NR12-A1, NR12-A2, and NR12-A3; oriented upstream) were synthesized using the ABI 394 DNA/RNA synthesizer under a condition to attach a trityl group to the 5'-terminus. Then, the products were purified using an OPC column (ABI #400771) to obtain full-length primers.

NR12-S1; 5'-GCA ACA GTC AGA ATT CTA CTT GGA GCC-3'(SEQ ID NO:11)
NR12-S2; 5'-CAT TAA GTA CGT ATT TCA AGT GAG ATG TC-3'(SEQ ID NO:12)
NR12-S3; 5'-GGT ACT GGC AGC CTT GGA GTT CAC TG-3'(SEQ ID NO:13)
NR12-A1; 5'-CAG TGA ACT CCA AGG CTG CCA GTA CC-3'(SEQ ID NO:14)
NR12-A2; 5'-GAC ATC TCA CTT GAA ATA CGT ACT TAA TG-3'(SEQ ID NO:15)
NR12-A3; 5'-GGC TCC AAG TAG AAT TCT GAC TGT TGC-3'(SEQ ID NO:16)

Above oligonucleotide primers, NR12-S1 and NR12-A3, NR12-S2 and NR12-A2, and NR12-S3 and NR12-A1 were designed to have completely complementary sequence to each other.

(4) Cloning of N-Terminal cDNA by 5'-RACE Method

In order to isolate full-length cDNA of NR12, 5'-RACE PCR was performed using NR12-A1 of (3) for primary PCR, and NR12-A2 of (3) for secondary PCR, respectively. PCR experiment was performed using Human Fetal Liver Marathon-Ready cDNA Library (Clontech #7403-1) as the template, and Advantage cDNA Polymerase Mix (Clontech #8417-1) on the thermal cycler (Perkin Elmer Gene Amp PCR System 2400). Under the following conditions, as a result, PCR products of two different sizes were obtained as shown in FIG. 3.

Condition of the primary PCR was as follows: 94° C. for 4 min, 5 cycles of "94° C. for 20 sec, 72° C. for 90 sec", 5 cycles of "94° C. for 20 sec, 70° C. for 90 sec", 28 cycles of "94° C. for 20 sec, 68° C. for 90 sec", 72° C. for 3 min, and termination at 4° C.

Condition of the secondary PCR was as follows: 94° C. for 4 min, 5 cycles of "94° C. for 20 sec, 70° C. for 90 sec", 25 cycles of "94° C. for 20 sec, 68° C. for 90 sec", 72° C. for 3 min, and termination at 4° C.

Two amplification products were obtained by the PCR and both of them were subcloned into pGEM-T Easy vector (Promega #A1360), and the nucleotide sequences were determined. The transformation of the PCR product into the pGEM-T Easy vector was performed using T4 DNA ligase (Promega #1360) in a reaction at 4° C. of 12 hours. Recombinants of the PCR products and pGEM-T Easy vector were obtained by the transformation of E. coli DH5α strain (Toyobo #DNA-903). Recombinants were selected by using Insert Check Ready Blue (Toyobo #PIK-201). The nucleotide sequences were determined using the BigDye Terminator Cycle Sequencing Ready Reaction Kit (ABI/Perkin Elmer #4303154) and by analyzing with the ABI PRISM 377 DNA Sequencer. Nucleotide sequences of the whole insert fragment of 10 independent clones were determined. As a result, they were divided into two groups, one consisting of 4 clones with a size of 1.3 kb, and the other consisting of 6 clones with a size of 1.0 kb, based on the length of the base pairs and the differences in sequence. However, the former 5'-RACE PCR products of 1.3 kb were revealed to be non-specific PCR amplification products. This sequence is derived from the minor band shown in FIG. 3. On the other hand, the latter 5'-RACE PCR products of 1.0 kb were recognized as partial nucleotide sequences of NR12 that resulted from a correct PCR amplification reaction.

(5) Cloning of C-Terminal cDNA by 3'-RACE Method

To isolate the C-terminal sequence of a cDNA clone corresponding to the full-length NR12, 3'-RACE PCR was performed using NR12-S1 primer of (3) for the primary PCR, and NR12-A2 of (3) for secondary PCR, respectively. The PCR was performed under the same condition as in the 5'-RACE above except the Human Thymus Marathon-Ready cDNA Library (Clontech #7415-1) was used as the template. More specifically, Advantage cDNA Polymerase Mix and the Perkin Elmer Gene Amp PCR System 2400 thermalcycler was used in the PCR experiment. Under the same PCR condition to those described in (4), 3'-RACE amplification product showing an identical size of 750 bp was obtained as shown in FIG. 3. The obtained PCR product was subcloned into the pGEM-T Easy vector as above to determine the nucleotide sequence. The recombination of the PCR product into the pGEM-T Easy vector was performed using T4 DNA ligase in a reaction at 4° C. for 12 hours. The recombinant of the PCR product and pGEM-T Easy vector was obtained by transformation of E. coli DH5αstrain, and selection of the recombinant was done using Insert Check Ready Blue as described above. The nucleotide sequence was determined using the BigDye Terminator Cycle Sequencing Ready Reaction Kit and the ABI PRISM 377 DNA Sequencer for analysis. The nucleotide sequences of the whole insert fragment from 2 independent clones of genetic recombinants revealed that the clones contain the C-terminal sequence of the full-length NR12 cDNA clone having a poly A sequence.

Then, the nucleotide sequence determined by the 3'-RACE-PCR and those determined by 5'-RACE-PCR in (4) were combined to finally determine the whole nucleotide sequence of the cDNA clone encoding the secretory form soluble receptor-like protein named NR12.1. The determined nucleotide sequence of NR12.1 cDNA (SEQ ID NO:1) and the amino acid sequence encoded by the sequence (SEQ ID NO:2) are shown in FIG. 4.

(6) Cloning of a C-Terminal Splicing Variant by 3'-RACE Method

Although the NR12.1 clone isolated above had sufficient feature of known hemopoietin receptors according to the result of structural analysis, it did not possess a transmembrane region. Therefore, it was inferred to encode a soluble receptor-like protein as above-mentioned. Further, the present inventors predicted the existence of splicing variants that have a transmembrane region especially in the C-terminal region of the transcription product of the present gene, and tried to isolate NR12 cDNA clones by successive 3'-RACE method.

Thus, 3'-RACE PCR was performed using the above-mentioned NR12-S2 primer of (3) for primary PCR, and NR12-S3 primer for secondary PCR. Under the same PCR condition to those described in (4) for 5'-RACE method except using Human Testis Marathon-Ready cDNA Library (Clontech #7414-1) as the template. As a result, multiple 3'-RACE PCR products with different sizes were obtained. All of the obtained PCR products were subcloned into the pGEM-T Easy vector as described above to determine the nucleotide sequences. Nucleotide sequences of the whole insert fragments of 6 independent clones of genetic recombinants were determined. As a result, one of these clones was found to be identical to NR12.1 determined above. The other 5 clones were possible to encode the target transmembrane protein having transmembrane regions. That is, the present inventors were able to confirm the existence of splicing variants of NR12 as expected. Furthermore, the 5 cDNA clones above showed differences in the C-terminal extracellular region due to alternative splicing. Namely, two of these clones had only a short intracellular region and were named NR12.2. On the other hand, the other 3 clones had a long intracellular region. These cDNA clones with a long ORF were named NR12.3, and were distinguished from the above sequence, NR12.2.

Then, the nucleotide sequence determined by the 3'-RACE PCR and those from the 5'-RACE PCR products in (4) were combined to finally determine the whole nucleotide sequence of the cDNA clone that encodes the transmembrane receptor protein. The nucleotide sequence determined for NR12.2 cDNA (SEQ ID NO:3) and its amino acid sequence (SEQ ID NO:4) are shown in FIG. 5. The nucleotide sequence of NR12.3 cDNA (SEQ ID NO:5) and its amino acid sequence (SEQ ID NO:6) are shown in FIGS. 6 and 7.

The exon site sequence was predicted in above (2) from the splicing consensus sequence in RNA transcription (Hames, B. D. and Glover, D. M., Transcription and Splicing (Oxford, IRL Press), 1988, p 131–206) and not by using program such as genome analysis software. According to the determination of the whole nucleotide sequence of isolated cDNA clones, it was revealed that the exon site predicted within the partial sequence of AL109843 shown in FIG. 1 correspond completely to that observed in the actual transcription of the NR12 gene. However, it was revealed that only the transcription product of NR12.1 cDNA clone was one which elongates to the 3'-untranslated region read through the identical sequence as that of the genome structure without splicing after the termination of WS exon.

(7) Structural Feature of NR12 and Prediction of its Function

As a result of the determination of the whole nucleotide sequences of NR12.1, NR12.2 and NR12.3, it was revealed that they are the transcription products having structural variety in the C-terminus due to alternative splicing. The NR12.1 may encode a secretory form soluble hemopoietin receptor-like protein consisting of 337 amino acids according to its primary structure, while the NR12.2 and NR12.3 may encode transmembrane hemopoietin receptor proteins consisting of 428 and 629 amino acids, respectively. The characteristics of each NR12 were as follows.

First, it is predicted that the sequence from the $1^{st}$ Met to the $23^{rd}$ Gly in the common extracellular domain of these clones is the typical secretion signal sequence. Herein, the first Met is presumed to be the translation initiation site because there exists an in-frame termination codon at the minus 32 position from the $1^{st}$ Met. Next, an Ig-like region exists in the region from the $24^{th}$ Gly to the $124^{th}$ Pro residue. In addition, it is predicted that the region from the $133^{rd}$ Cys to the $144^{th}$ Cys residue forms one of the loop structures which is a ligand-binding site. Furthermore, the region from the $290^{th}$ Tyr to the $295^{th}$ Arg residue corresponds to the highly conserved YR motif, and a typical WS motif is also found at residues from the $304^{th}$ Trp to $308^{th}$ Ser.

Herein, the NR12.1 encodes 29 amino acids after the WS motif and the translation frame terminates at the next stop codon. Therefore, the NR12.1 encodes a soluble hemopoietin receptor protein that does not have a transmembrane domain. On the other hand, the 26 amino acids following the conserved motif above from the $352^{nd}$ Gly to the $377^{th}$ Asn residue in NR12.2 and NR12.3 correspond to a typical transmembrane domain. The NR12.2 and NR12.3 encode identical amino acid sequences to the $413^{th}$ Gln residue in the extracellular region. However, structural differences exist in the C-terminal region following the $413^{th}$ Gln residue due to alternative splicing which connects them to different exons. Namely, NR12.2 encodes 428 amino acids and the translation frame is terminated at the next stop codon. Thus, it has only a short intracellular region consisting of 51 amino acids. On the other hand, NR12.3 encodes 629 amino acids and has an intracellular region consisting of 252 amino acids. According to the structural characteristics above, NR12 gene was recognized to possess sufficient characteristics as novel hemopoietin receptor proteins.

EXAMPLE 2

Tissue Distribution Determination and Expression Pattern Analysis of NR12 Gene by RT-PCR mRNA was detected using the RT-PCR method to analyze the expression distribution and the expression pattern of NR12.1 gene in different human organs. NR12-PPD primer with the sequence below was synthesized as a sense primer (downstream orientation) for the RT-PCR analysis. NR12-A1 primer synthesized in Example 1 (3) was used as the antisense primer (upstream orientation). The NR12-PPD primer was synthesized and purified as in Example 1 (3). It was expected that the common N-terminal region in all splice variants, NR12.1, NR12.2 and NR12.3, are amplified and detected using these primer sets (NR12-PPD and NR12-A1).

hNR12-PPD; 5'-CCG CCA GAT ATT CCT GAT GAA GTA ACC-3' (SEQ ID NO:17)

The templates used were Human Multiple Tissue cDNA (MTC) Panel I (Clontech #K1420-1), Human MTC Panel II (Clontech #K1421-1), Human Immune System MTC Panel (Clontech #K1426-1), and Human Fetal MTC Panel (Clontech #K1425-1). PCR was performed using Advantage cDNA Polymerase Mix (Clontech #8417-1) on a thermal cycler (Perkin Elmer Gene Amp PCR System 2400). PCR was performed by following condition to amplify the target gene: 94° C. for 4 min, 5 cycles of "94° C. for 20 sec, 72° C. for 1 min", 5 cycles of "94° C. for 20 sec, 70° C. for 1 min", 25 cycles of "94° C. for 20 sec, 68° C. for 1 min", 72° C. for 3 min, and termination at 4° C.

Figure 8:
FIG. 8 shows photographs demonstrating the results of RT-PCR analysis of the genetic-expression distribution of the NR12 in human organs. The arrow indicates the size of the specific PCR amplification product of NR12.

As shown in FIG. 8, strong expression of NR12 was observed in the hematopoietic cell line tissue and immune system cell line tissue such as adult spleen, thymus, lymph node, bone marrow, and peripheral leukocyte. Expression was also detected in testis, liver, lung, kidney, pancreas, and gastrointestinal tract such as small intestine and colon. Moreover, NR12 gene expression was also observed in all analyzed mRNA derived from human fatal tissues. Performing PCR using human G3PDH primers under the above condition and detecting the expression of the housekeeping gene G3PDH, it was confirmed that the number of mRNA copies among the template mRNA had been normalized.

The size of the RT-PCR amplification product was 561 bp, which was consistent with the size calculated from the determined nucleotide sequence of NR12 cDNA. Thus, the product was considered to be the product of specific PCR amplification reaction. This was further confirmed by Southern blotting as in the following, and the possibility that the product was a non-specific PCR amplification product was denied.

The analyses of expression distribution and expression pattern of NR12 gene by RT-PCR revealed that the expression is restricted to specific organs and tissues, and also that the amount of expression varies greatly among organs. Taking all the result of NR12 gene expression distribution together, the fact that especially strong expression was detected in tissue considered mainly to include immunocyte tissues and hematopoietic cells suggest strongly the possibility that NR12 functions as a novel hemopoietin receptor. Furthermore, the fact that the expression of NR12 was also observed in other tissues suggests that NR12 can regulate various physiological functions in vivo not only those in the immune system and hematopoietic system.

Moreover, existence of splicing variants was recognized. This strongly suggests that transcriptional regulation of the NR12 gene expression is strictly controlled by the transcriptional regulation determining functional specificity, transcriptional induction by exogenous stimulating factor, and regulation of alternative splicing in specific cell types.

EXAMPLE 3

Verification of the Specificity of RT-PCR Product by Southern Blotting

In order to verify the specificity of amplification, the RT-PCR amplified target gene product in Example 2 was subjected to Southern blotting using NR12 specific cDNA fragment as a probe. At the same time, the amount of RT-PCR product was quantitatively detected by the strength of labeled signal to assess relative gene expression levels among different human organs. The RT-PCR product was electrophoresed on an agarose gel, blotted onto a charged nylon membrane, Hybond N (+) (Amersham, cat #RPN303B), and was subjected to hybridization. The 5'-RACE PCR product cDNA fragment corresponding to the N-terminus of the NR12 obtained in Example 1 (4) was used as a probe specific to NR12. Probes were prepared using the Mega Prime Kit (Amersham, cat #RPN1607), and labeled with radioisotope, [$\alpha$-$^{32}$P] dCTP (Amersham, cat #AA0005). Hybridization was performed using Express Hyb Hybridization Solution (Clontech #8015-2), and after the prehybridization at 68° C. for 30 min, heat-denatured labeled probe was added to conduct hybridization at 68° C. for 120 min. After subsequent wash in (1) 1×SSC/0.1% SDS at room temperature for 5 min; (2) 1×SSC/0.1% SDS at 50° C. for 30 min; and (3) 0.1×SSC/0.1% SDS at 50° C. for 30 min, the membrane was exposed to Imaging Plate (FUJI #BAS-III), and NR12 specific signal was detected by the Image Analyzer (FUJIX, BAS-2000 II).

Figure 9:
FIG. 9 shows a photograph demonstrating the results of quantification of the NR12 gene expression in human organs by Southern blotting. The arrow indicates the size of the specific signal of detected NR12.

As shown in FIG. 9, all the amplified PCR products by the RT-PCR above were verified as specific amplification products. Furthermore, the result of quantification of relative expression level among each tissue also supported above-mentioned assessment. The detection method for target gene expression using RT-PCR and Southern blotting in combination is known to have extremely high sensitivity as compared to other methods for expression analysis. Nevertheless, NR12 gene expression was not detected in adult heart, skeletal muscle, adult brain, prostate, ovary, or placenta at all.

EXAMPLE 4

Northern Blot Analysis of NR12 Gene Expression

Northern blot analysis of NR12 gene expression was performed to examine the expression pattern of NR12 gene in human organs and human cancer cell lines, and to determine the size of NR12 transcripts. Human Multiple Tissue Northern (MTN) Blot (Clontech #7760-1), Human MTN Blot II (Clontech #7759-1), Human MTN Blot III (Clontech #7767-1), and Human Cancer Cell Line MTN Blot (Clontech #7757-1) were used.

The cDNA fragment obtained by 5'-RACE in Example 1 (4) was used as the probe. The probe was prepared using Mega Prime Kit and radio-labeled with [$\alpha$-$^{32}$P]dCTP as in Example 3. Hybridization was performed using Express Hybridization Solution, and after prehybridization at 65° C. for 30 min heat-denatured labeled probe was added to conduct hybridization at 65° C. for 16 hr. After subsequent wash in (1) 1×SSC/0.1% SDS at room temperature for 5 min; (2) 1×SSC/0.1% SDS at 48° C. for 30 min; and (3) 0.5×SSC/0.1% SDS at 48° C. for 30 min, the membrane was exposed to an Imaging Plate as above, and an attempt to detect NR12 specific signal was made using an Image Analyzer.

The method failed to detect any signal in any of the examined human organs. This could be because Northern blotting has a significant lower sensitivity than RT-PCR and thus failed to detect mRNA with low expression level.

EXAMPLE 5

Construction of an NR12 Ligand Screening System Using Growth Factor-dependent Cell Lines Ligands that bind specifically to the protein of this invention can be screened by the following step: (1) preparing a chimeric receptor by ligating the extracellular domain of the protein of this invention with the intracellular domain containing the transmembrane domain of a hemopoietin receptor protein comprising a known signal transduction ability; (2) expressing this chimeric receptor on the cell surface of a suitable cell line, preferably, a cell line that can survive and proliferate only under the presence of a suitable factor (a growth factor-dependent cell line); and (3) culturing the cell line by adding a material that is expected to contain various growth factors, cytokines, or hemopoietic factors. This method utilizes the fact that the above-mentioned growth factor-dependent cell line only survives and proliferates when a ligand specifically binding to the extracellular domain of the protein of the invention exists within the test material and is killed rapidly without the existence of the growth factor. Known hemopoietic receptors are, for example, the thrombopoietin receptor, erythropoietin receptor, G-CSF receptor, gp130, etc. However, the partner of the chimeric receptor used in the screening of the invention is not limited to these known hemopoietic receptors, and any receptor may be used so long as it contains the structure necessary for the signal transducing activity in the cytoplasmic domain. IL-3-dependent cell lines, such as Ba/F3 and FDC-PL, can be exemplified as growth factor-dependent cell lines.

First, the cDNA sequence encoding the extracellular region of NR12 (the amino acid sequence from the $1^{st}$ Met to the $319^{th}$ Gly) was amplified by PCR, and this DNA fragment was bound in frame to the DNA fragments encoding the transmembrane region and the intracellular region of a known hemopoietin receptor to prepare a fusion sequence encoding a chimeric receptor. The TPO receptor (Human MPL-P) was selected from the candidates described above as the known partner hemopoietin receptor. The constructed chimeric receptor sequence above was inserted into the plasmid vector, pME18S/neo, which can be expressed in mammalian cells. A schematic diagram of the structure of the constructed pME18S/NR12-TPOR chimeric receptor is shown in FIG. 10. The chimeric receptor-expressing vector was introduced into the growth factor-dependent cell line Ba/F3, and was forced to express. Then, stable gene-introduced cells were selected. The selection can be done by utilizing the fact that the expression vector contains a drug (neomycin) resistant gene, and thus, only gene-introduced cells that obtained drug tolerance can be proliferated in the culture containing the drug. Novel hematopoietin may be screened by constructing a screening system that utilizes the ability of the chimeric receptor-expressing cell lines to survive and proliferate only under the existence of a ligand functionally binding specifically to the NR12. In this case, the culture of the chimeric receptor-expressing cell line is conducted in medium supplemented with a material expected to include a target ligand in place of the growth factor (IL-3, in this case) free medium described above.

EXAMPLE 6

Construction of an Expression System of Secretary and Soluble Recombinant NR12 Protein Though rare, cell membrane-binding proteins except soluble proteins can be envisaged as a ligand specifically binding to the protein of the invention. In such cases, screening can be done by labeling the protein containing only the extracellular domain of the protein of the invention, or a fusion protein in which a partial sequence of another soluble protein is added to the extracellular domain of the present protein, and then, measuring the binding with cells expected to express the ligand.

Examples of the former proteins containing only the extracellular domain of the protein of the invention are, for example, soluble receptor proteins artificially prepared by inserting a stop codon to the N-terminal side of the transmembrane domain, or NR12.1 that encodes the soluble type protein of NR12. On the other hand, the latter proteins may be prepared by adding labeling peptide sequences such as Fc site of immunogloblins, and FLAG peptide to the C-terminus of the extracellular domain of the protein of the invention. These soluble labeled proteins can be also used for the detection in the West-western blotting method.

The present inventors selected a construction method as follows: (1) cDNA sequence encoding the extracellular region of NR12 (amino acid sequence from the $1^{st}$ Met to the $319^{th}$ Gly) was amplified by PCR; and (2) FLAG peptide sequence was added in frame to the C-terminus of the amplified DNA fragment to obtain a sequence encoding the soluble targeted protein. The constructed sequence was inserted into the plasmid vector, pCHO, which can be expressed in mammalian cells. A schematic diagram of the structure of the constructed pCHO/NR12-TPOR chimeric receptor is shown in FIG. 10. This expression vector was introduced into mammalian cells, CHO cells, and was forced to express. Then, stable gene-introduced cells were selected. After confirming expression of the soluble protein, the expression cells were cultured in large scale. The recombinant protein secreted into the culture supernatant can be immunoprecipitated using anti-FLAG peptide antibody, and may be purified by affinity columns, etc.

The obtained recombinant protein can be applied not only for the assay mentioned above, but also, for example, for detection of specific biding activity within a material expected to contain a target ligand by BIA-CORE system (Pharmacia). Thus, it is extremely important for searching novel hemopoietins that can bind to NR12.

EXAMPLE 7

Reisolation of Human Full-length NR12 CDS (1) Design of Oligonucleotide Primers

The present inventors already had succeeded in isolating the full-length cDNA of NR12 gene. However, the N-terminal sequence and C-terminal sequence of the isolated target gene were isolated separately due to the use of 5'-RACE and 3'-RACE method for the cDNA isolation. Thus, the present inventors attempted to reisolate NR12.2 and NR12.3 genes that contain continuous full-length coding sequences.

First, a sense primer (NR12.2-MET) described below that contains the start codon, Met sequence, with a common nucleotide sequence to each cDNA clone of NR12 was designed. As the antisense primers, NR12.2-STP and NR12.3-STP that contain a stop codon specific to NR12.2 and NR12.3, respectively, were designed. The primers were synthesis as in Example 1 (3). More specifically, ABI's 394 DNA/RNA Synthesizer was used for the primer synthesis under the condition where a trityl group is attached to the 5'-terminus. Then, the product was purified using and OPC column (ABI #400771) to obtain full-length primers.

NR12.1-MET; 5'-ATG AAT CAG GTC ACT ATT CAA TGG-3'(SEQ ID NO:18)

NR12.2-STP; 5'-GCA GTC CTC CTA CTT CAG CTT CCC-3'(SEQ ID NO:19)

NR12.3-STP; 5'-TTG ATT TTG ACC ACA CAG CTC TAC-3'(SEQ ID NO:20)

(2) PCR Cloning

In order to isolate the full-length CDS of NR12, PCR cloning was performed using NR12.1-MET primer of (1) as sense primer and NR12.2-STP and NR12.3-STP primer as antisense primers, respectively. Human Thymus Marathon-Ready cDNA Library (Clontech #7415-1) was used as the template, and Advantage cDNA Polymerase Mix (Clontech #8417-1) for the PCR experiment on a thermal cycler (Perkin Elmer Gene Amp PCR System 2400) under the condition described below. The PCR product of 1301 bp named NR12.4 was obtained using the primer set "NR12.1-MET and NR12.2-STP", and that of 1910 bp named NR12.5 was obtained using the primer set "NR12.1-MET and NR12.3-STP".

PCR was performed by a single cycle of "94° C. for 4 min", 5 cycles of "94° C. for 20 sec, 72° C. for 90 sec", 5 cycles of "94° C. for 20 sec, 70° C. for 90 sec", 28 cycles of "94° C. for 20 sec, 68° C. for 90 sec", a single cycle of "72° C. for 3 min", and was terminated at 4° C.

The obtained PCR products were subcloned into pGEM-T Easy vectors (Promega #A1360) as in Example 1 (4), and the nucleotide sequences were determined. Recombination of the PCR products into the pGEM-T Easy vectors were performed using T4 DNA ligase (Promega #1360) in a reaction at 4° C. for 12 hours. The recombinant of the PCR product and the pGEM-T Easy vector was obtained by transformation of E. coli strain DH5α (Toyobo #DNA-903), and Insert Check Ready Blue (Toyobo #PIK-201) was used for the selection of the genetic recombinant. The nucleotide sequence was determined using the BigDye Terminator Cycle Sequencing SF Ready Reaction Kit (ABI/Perkin Elmer #4303150) and was analyzed by the ABI PRISM 377 DNA Sequencer. The nucleotide sequence of the insert fragments in respective recombinants of NR12.4 and NR12.5 were analyzed, and the sequences of cDNA clones that may encode the full-length CDS were determined.

As a result, it was revealed that NR12.4 contains the full-length ORF of NR12.2 but not the 5'-untranslated region or 3'-untranslated region except the sequence derived from primers due to the design of the used primers in the PCR. NR12.5 also contained the full-length ORF of NR12.3 but not the 5'-untranslated region or 3'-untranslated region except the sequence derived from the primers. The determined nucleotide sequence of NR12.4 and its amino acid sequence are shown in FIGS. 11 and 12, and the determined nucleotide sequence of NR12.5 and its amino acid sequence are shown in FIGS. 13 and 14.

E. coli strain DH5α transfected with pGEM-T Easy vector (pGEM/NR12.5CDS) that contains the NR12.5 cDNA of this invention was deposited internationally on Jul. 31, 2000 as follows.

Name and Address of the depositary institution

Depositary institution: National Institute of Bioscience and Human-Technology, Agency of Industrial Science and Technology, Ministry of International Trade and Industry.

Address: 1-1-3 Higashi, Tsukuba, Ibaraki 305-8566, Japan.

Deposition date: 31$^{st}$ Jul. 2000

Accession No.: FERM BP-7259

EXAMPLE 8

Cloning of Mouse NR12 Homologous Genomic Gene (1) Preparation of a Probe Fragment of Human NR12

Aiming to analyze the genomic structure of mouse NR12 gene, the present inventors performed plaque hybridization against the mouse genomic DNA library. To perform heterologous cross hybridization cloning against mouse genomic DNA library, probe fragment of human NR12 cDNA was prepared. The insert fragment cut out with Not I from the 5'-RACE product of human NR12 obtained in Example 1 (4) was purified, and used as the probe fragment. QIAquick Gel Extraction Kit (QIAGEN #28704) was used to extract and purify the insert fragment from the agarose gel. The probe was radiolabeled with [α-$^{32}$P] dCTP using Mega Prime Kit as in Example 3, and was used for plaque hybridization.

(2) Plaque Hybridization

Mouse 129SVJ strain Genomic DNA (Stratagene #946313) constructed in Lambda FIX II was used as the library. A genomic library of approximately 320 thousand plagues was developed in NZY agar medium, and the plaques were blotted onto a Hybond N (+) (Amersham #RPN303B) charged nylon membrane to conduct primary screening. Perfect-Hyb Solution (Toyobo #HYB-101) was used for hybridization, and after prehybridization at 60° C. for 30 min, heat-denatured labeled probe was added, and hybridization was conducted at 60° C. for 16 hr. After subsequent wash in: (1) 1×SSC/0.1% SDS at room temperature for 5 min; (2) 1×SSC/0.1% SDS at 50° C. for 30 min; and (3) 0.5×SSC/0.1% SDS at 50° C. 30 min, the membrane was exposed to an X-ray film (Hyperfilm MP: Amersham, #RPN8H) to detect mouse NR21 positive plaques.

As a result, 6 independent positive or pseudo-positive clones were obtained. The inventors succeeded in isolating plaques of 2 independent NR12 positive clones by performing secondary screening in a similar way to the primary screening against these 6 clones obtained by the primary screening. Lambda DNA of the isolated plaque was prepared in large scale by plate-lysing method. The insert fragments were cut out with restriction enzyme Sal I. Analysis of their size revealed that the fragments were approximately 18.5 kb and 16.0 kb, respectively.

INDUSTRIAL APPLICABILITY

The present invention provides novel hemopoietin receptor proteins and DNA encoding same. The present invention also provides: a vector into which the DNA has been inserted, a transformant harboring the DNA, and a method for producing recombinant proteins using the transformant. It further provides a method of screening for a compound or a natural ligand that binds to the protein. The protein of this invention is predicted to be associated with the regulation of immune system and hematopoiesis. Therefore, the proteins of this invention are expected to be useful in understanding immune responses and fundamental features of hematopoiesis in vivo. It is also expected that the proteins of the present invention can be used in the diagnosis and treatment of diseases related to immunity and hematopoiesis.

It is important to isolate unknown hematopoietic factors that can bind to the NR12 molecule of this invention. The gene of this invention is thought to be extremely useful in the screening of such unknown factors. Furthermore, peptide libraries and synthetic chemical materials may be searched to isolate and identify agonists and antagonists that can functionally bind to the NR12.

As described above, the NR12 gene is expected to provide a useful source for obtaining unknown hematopoietic factors or agonists that are capable of functionally binding to the receptor protein encoded by the NR12 gene. It is expected that cellular immunity and hematopoietic function in vivo will be enhanced by the administration of such functionally binding substances or specific antibodies that can activate the function of NR12 molecule to the organism. Thus, the NR12 gene facilitates the development of drugs for clinical application that promote proliferation or differentiation of the immune cells or hematopoietic cells, or that activates the function of immune cells. Such drugs may be used to enhance cytotoxic immunity against specific types of tumor. It is possible that NR12 is expressed in a restricted population of cells in the hematopoietic tissues. Accordingly, anti-NR12 antibodies would be useful in the isolation of such cell populations, which may then be used in cell transplantation treatments.

On the other hand, NR12.1, a splice variant of NRI2, may be used as an inhibitor for the NR12 ligand, as a decoy type receptor. Further, it is expected that by administering antagonists that can bind functionally to the NR12 molecule, or other inhibitors, as well as specific antibodies that can inhibit the molecular function of NR12 to the organism, one can potentially suppress cellular immunity or inhibit the proliferation of hematopoietic cells in vivo. Thus, such inhibitors may be applied as drugs for clinical application for use as, for example, proliferation inhibitors of immune cell and hematopoietic cell, differentiation inhibitors, immunosuppressive drugs, and anti-inflammatory drugs. Specifically, such inhibitors may be used to suppress the onset of autoimmune diseases arising from autoimmunity, or tissue rejection by the immune system of the living body, the primary problem in transplantation. Furthermore, the inhibitors may be effectively used to treat diseases caused by such aberrant promotion of immune response. Thus, the inhibitors may be used to treat a variety of allergies that are specific to particular antigens, such as metal and pollen.

What is claimed is:

1. A substantially purified polypeptide comprising the amino acid sequence of SEQ ID NO:2.

2. A substantially purified polypeptide consisting of the amino acid sequence of SEQ ID NO:2.

3. A recombinant polypeptide comprising the amino acid sequence of SEQ ID NO:2, wherein the polypeptide was produced by expression of a transformed host cell in vitro.

4. The polypeptide of claim 3, wherein the host cell is selected from the group consisting of a CHO cell, COS cell, 3T3 cell, myeloma cell, baby hamster kidney cell, HeLa cell, Vero cell, *Xenopus oocyte,* Sf9, Sf21, Tn5, *Nicotiana tabacum, Saccharomyces cerevisiae, Aspergillus niger, E. coli,* JM109, DH5α, HB101, and *Bacillus subtilis* cell.

5. A substantially purified polypeptide comprising amino acid residues Gly24 to Cys337 of SEQ ID NO:2.

6. A substantially purified polypeptide consisting of amino acid residues Gly24 to Cys337 of SEQ ID NO:2.

* * * * *